US010825177B2

(12) United States Patent
Isaacs et al.

(10) Patent No.: US 10,825,177 B2
(45) Date of Patent: Nov. 3, 2020

(54) IMAGING SYSTEM AND METHOD FOR IMAGE LOCALIZATION OF EFFECTERS DURING A MEDICAL PROCEDURE

(71) Applicant: TrackX Technology, LLC, Durham, NC (US)

(72) Inventors: Robert E. Isaacs, Chapel Hill, NC (US); Samuel Morris Johnston, Durham, NC (US); David Alexander Skwerer, Raleigh, NC (US); Randall Campbell, Hillsborough, NC (US)

(73) Assignee: TrackX Technology, LLC, Durham, NC (US)

( * ) Notice: Subject to any disclaimer, the term of this patent is extended or adjusted under 35 U.S.C. 154(b) by 0 days.

(21) Appl. No.: 16/556,737

(22) Filed: Aug. 30, 2019

(65) Prior Publication Data

US 2020/0034969 A1 Jan. 30, 2020

Related U.S. Application Data

(63) Continuation-in-part of application No. 15/596,547, filed on May 16, 2017, now Pat. No. 10,433,915.
(Continued)

(51) Int. Cl.
*A61B 5/05* (2006.01)
*G06K 9/00* (2006.01)
(Continued)

(52) U.S. Cl.
CPC .......... *G06T 7/0014* (2013.01); *A61B 90/36* (2016.02); *G06T 7/74* (2017.01);
(Continued)

(58) Field of Classification Search
USPC ....... 600/133, 302, 325, 339, 414, 424, 425, 600/462; 72/31.04; 382/128, 129,
(Continued)

(56) References Cited

U.S. PATENT DOCUMENTS

2008/0046062 A1* 2/2008 Camps ................ A61N 1/0587
607/133
2011/0060214 A1* 3/2011 Makower .............. A61B 34/20
600/424
(Continued)

*Primary Examiner* — Seyed H Azarian
(74) *Attorney, Agent, or Firm* — Maginot, Moore & Beck, LLP

(57) ABSTRACT

A computer-assisted imaging and localization system assists the physician in positioning implants and instruments into a patient's body. The system displays overlapping images—one image of the surgical site with the patient's anatomy and another image showing the implant(s) or instrument(s). The overlapping image of the implant/instrument is moved over the static image of the anatomy as the implant/instrument is moved. The moving image of the implant/instrument can be an unaltered image or an image altered to intensify or mitigate the anatomical or non-anatomical aspects of the moving image. Sliding these images over one another helps the surgeon in positioning devices or instruments with a high degree of accuracy and with a limited number of additional x-rays.

13 Claims, 76 Drawing Sheets

Related U.S. Application Data

(60) Provisional application No. 62/336,999, filed on May 16, 2016, provisional application No. 62/374,187, filed on Aug. 12, 2016, provisional application No. 62/337,010, filed on May 16, 2016.

(51) Int. Cl.
*G06T 7/00* (2017.01)
*A61B 90/00* (2016.01)
*G06T 7/73* (2017.01)

(52) U.S. Cl.
CPC ............... *G06T 2207/30008* (2013.01); *G06T 2207/30021* (2013.01); *G06T 2210/41* (2013.01)

(58) Field of Classification Search
USPC ......... 382/130.131, 130, 132, 133, 134, 321
See application file for complete search history.

(56) References Cited

U.S. PATENT DOCUMENTS

| | | | |
|---|---|---|---|
| 2014/0137618 A1* | 5/2014 | Isaacs | A61B 17/8863 72/31.04 |
| 2016/0270780 A1* | 9/2016 | Hall | A61B 34/74 |
| 2017/0105786 A1* | 4/2017 | Scheib | A61B 18/1442 |
| 2018/0214138 A9* | 8/2018 | Prisco | A61B 34/71 |

* cited by examiner

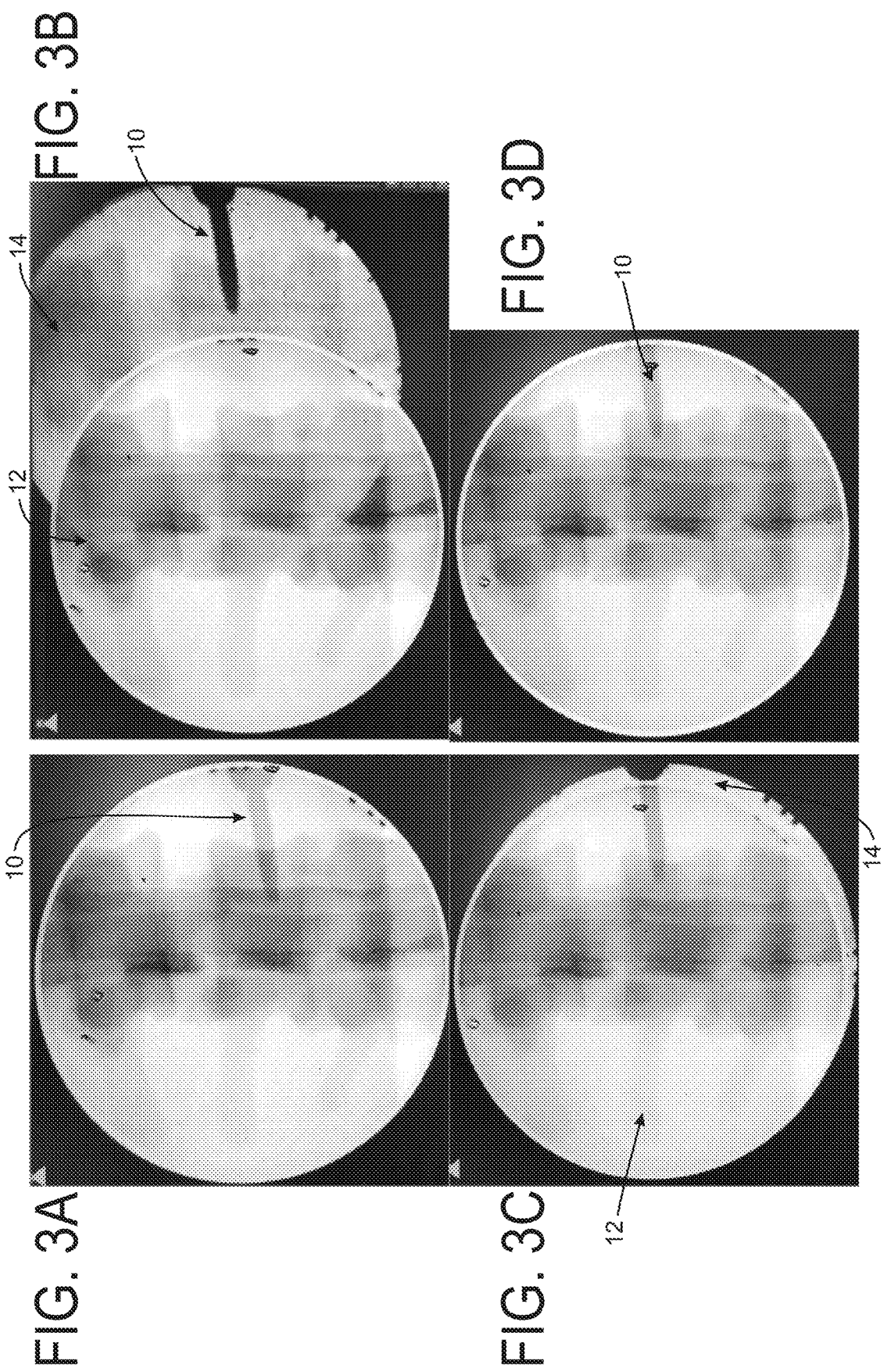

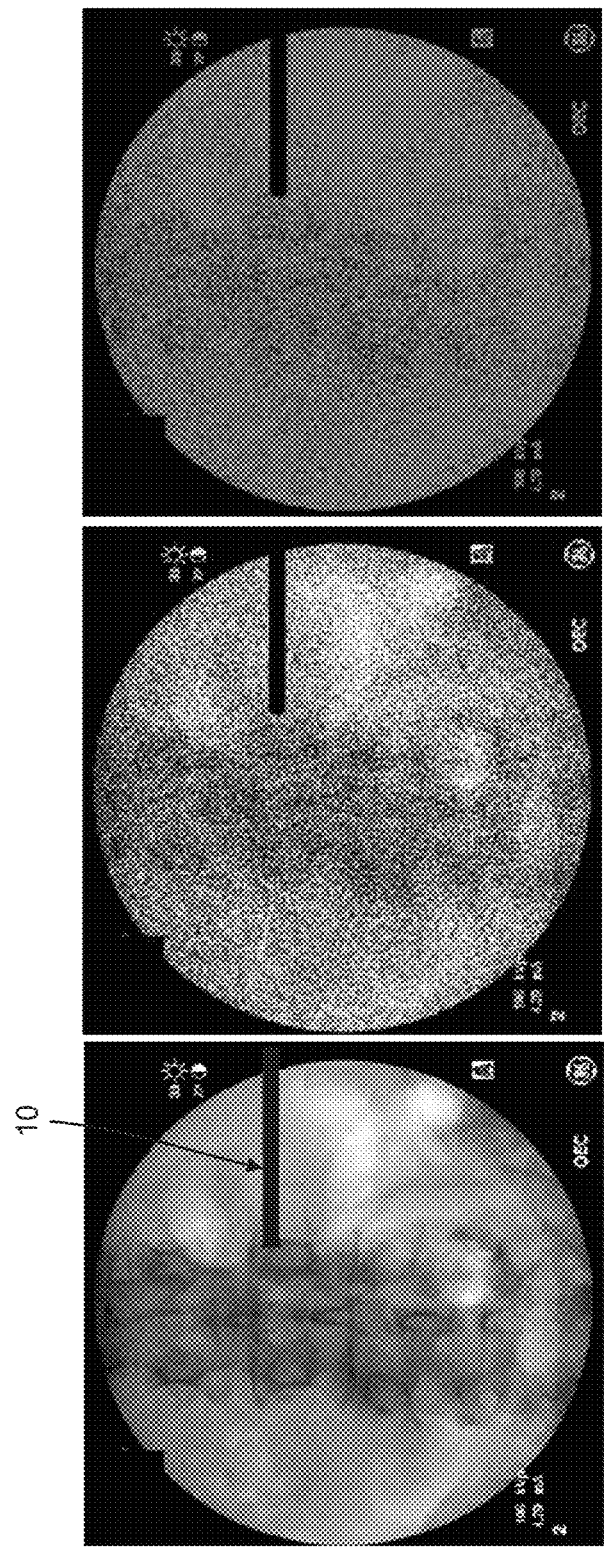

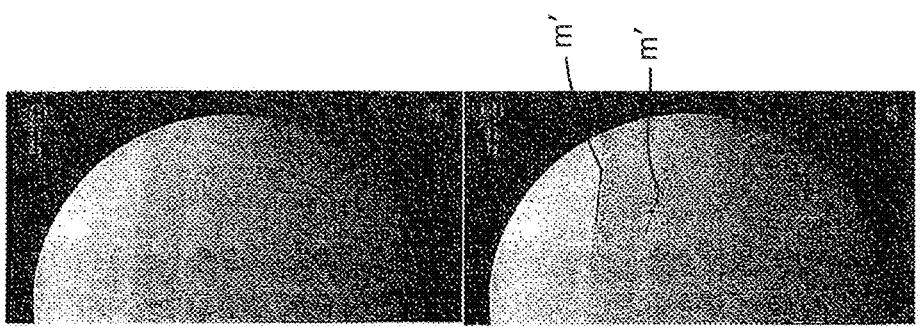
FIG. 12B / FIG. 12C
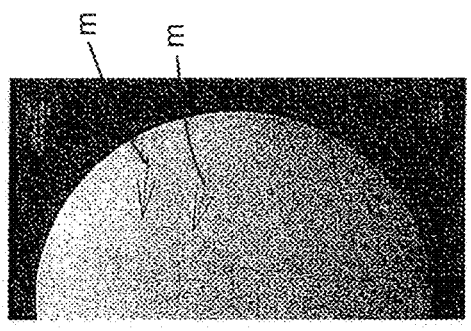
FIG. 12A

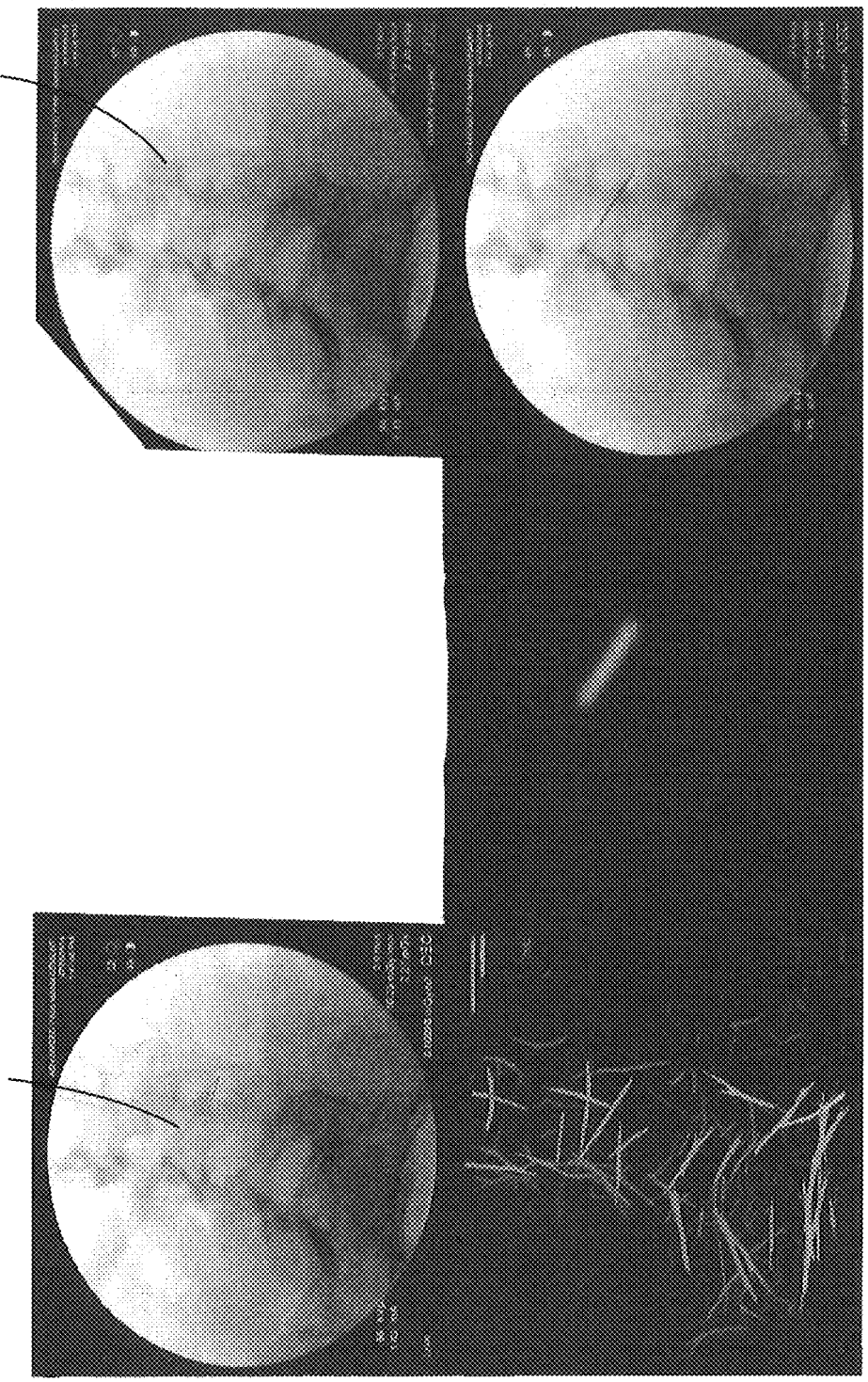
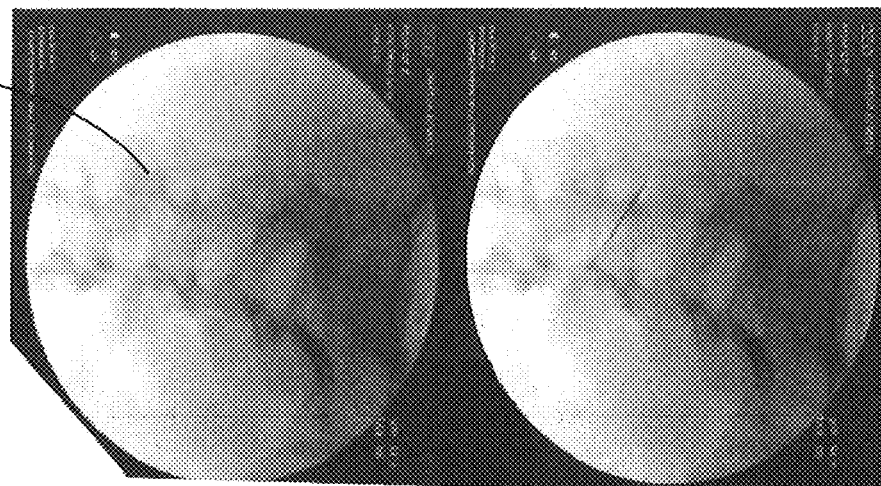

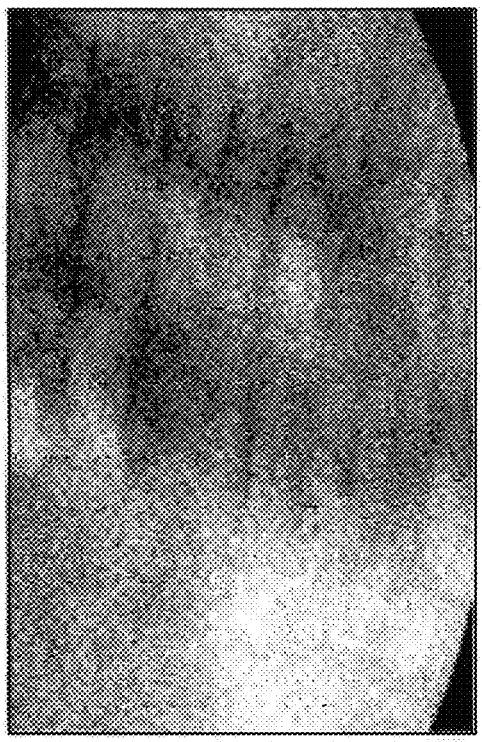
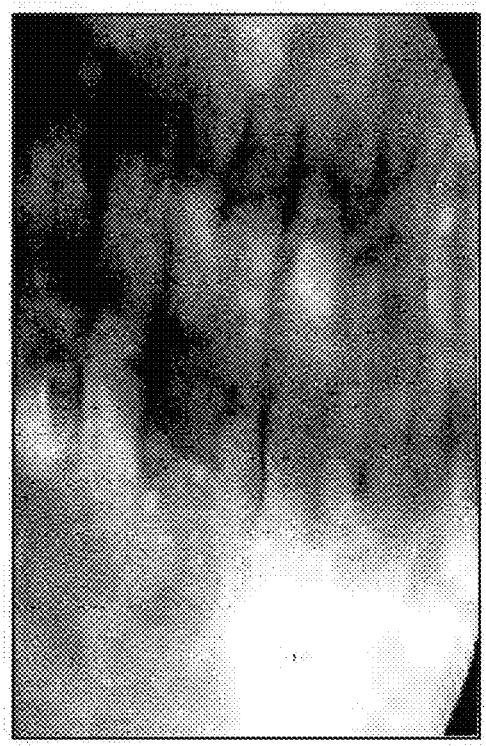
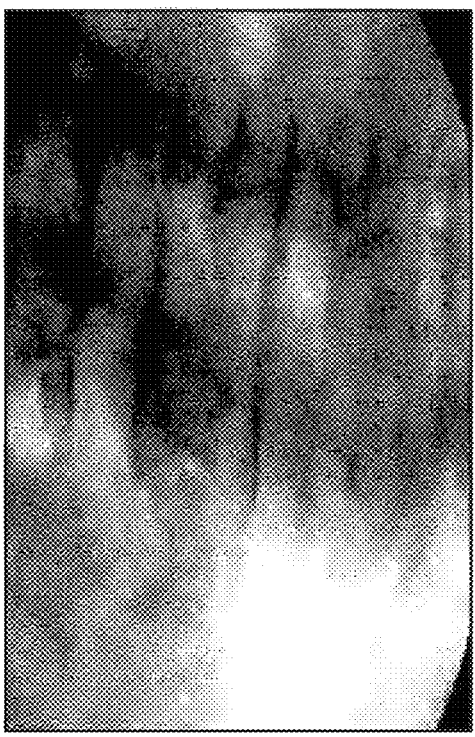
FIG. 29A
FIG. 29B
FIG. 29C local standard deviation of gradient local standard deviation of local standard deviation gradient of gradient gradient of local standard deviation Image Statistics

FIG. 32A
FIG. 32B

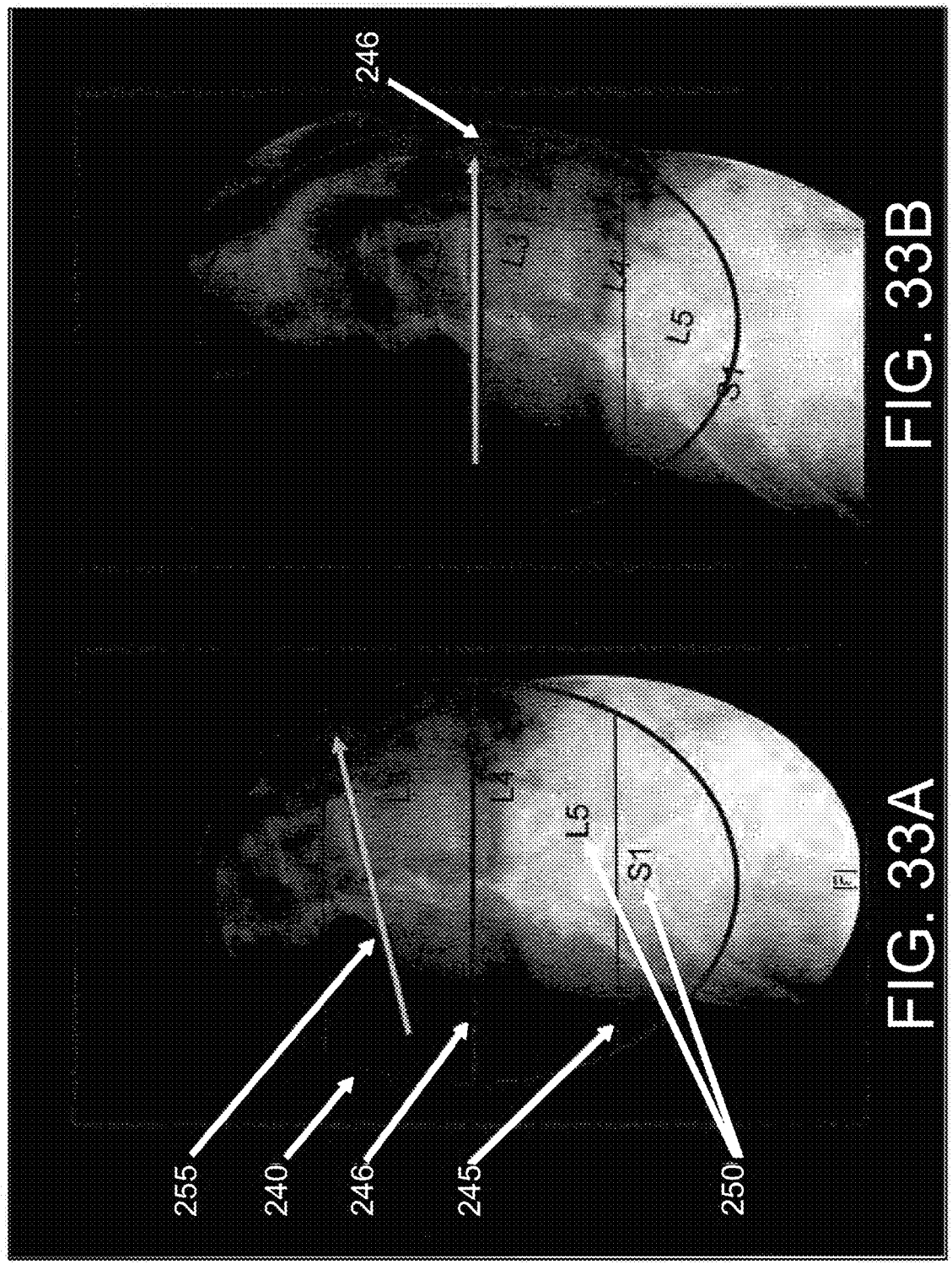

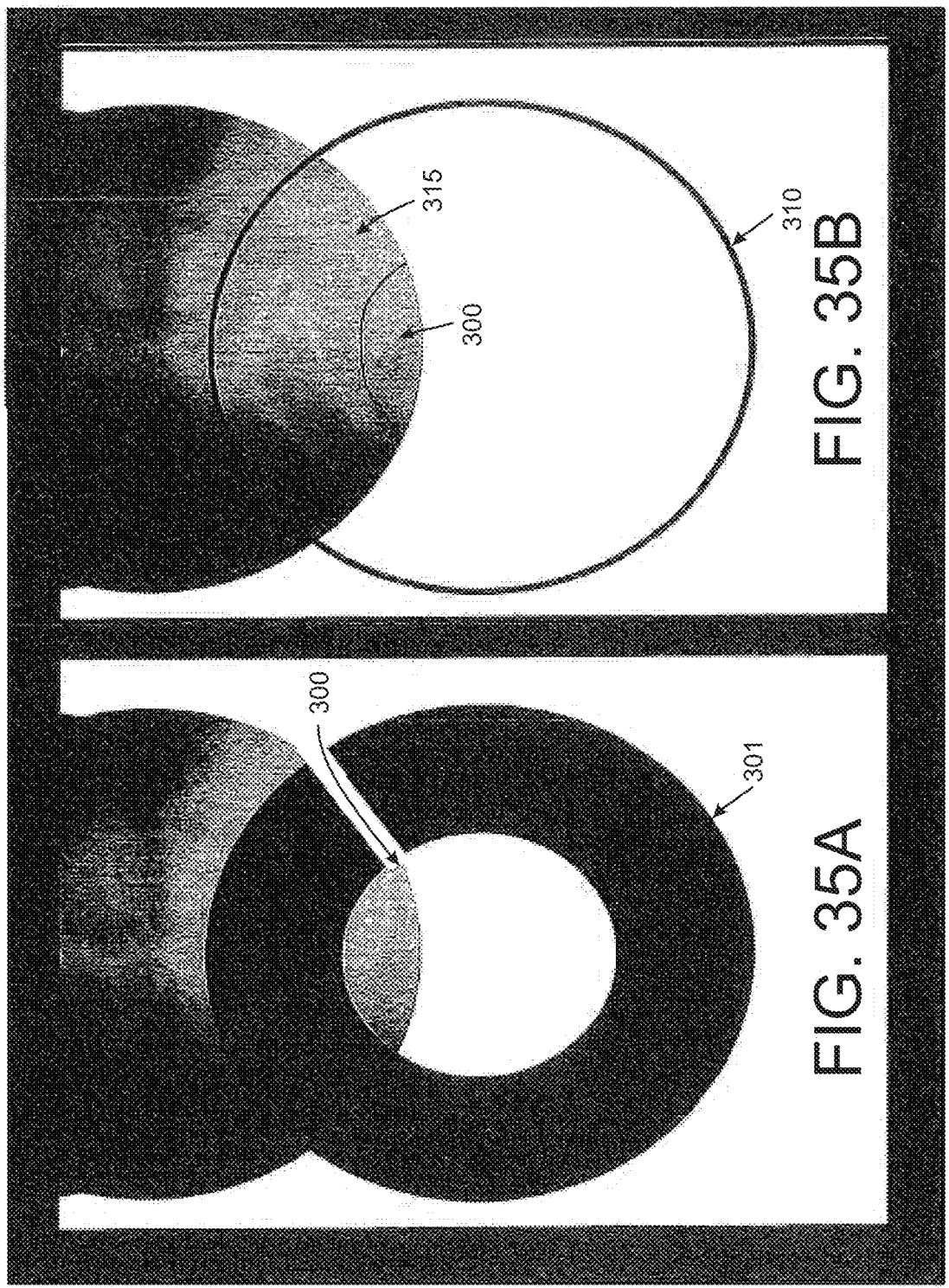

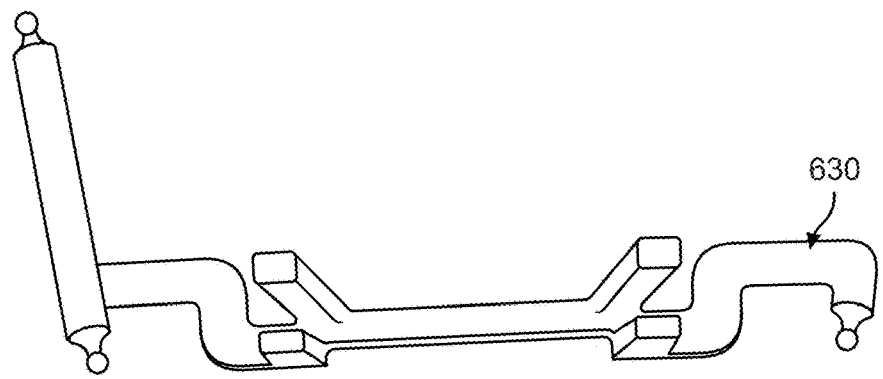
FIG. 54A
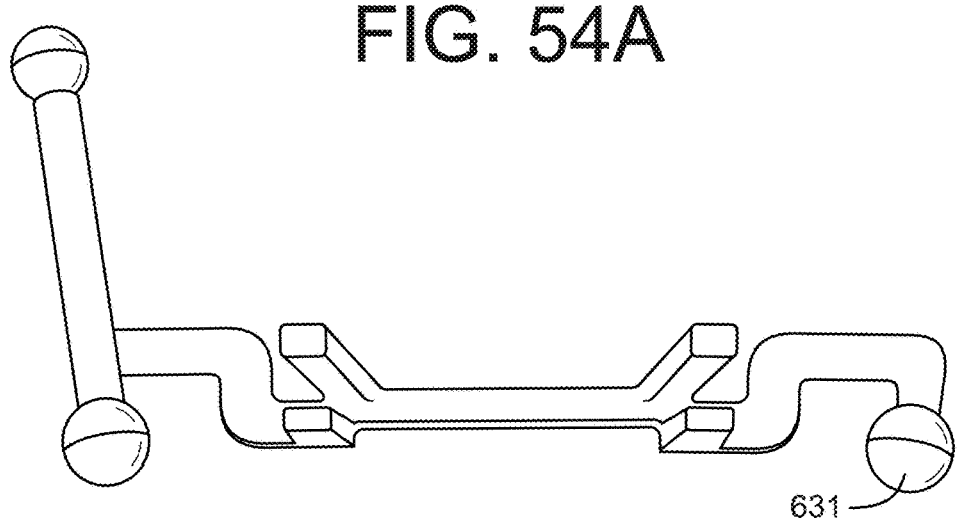
FIG. 54B
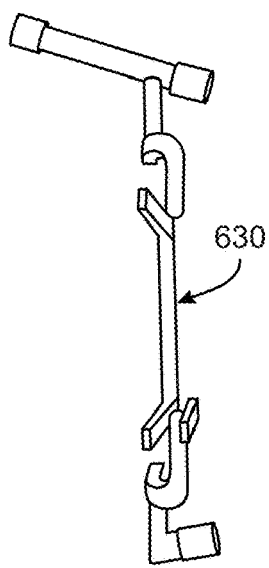 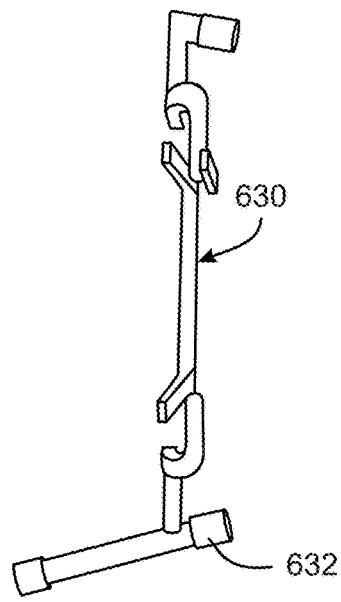
FIG. 54C FIG. 54D

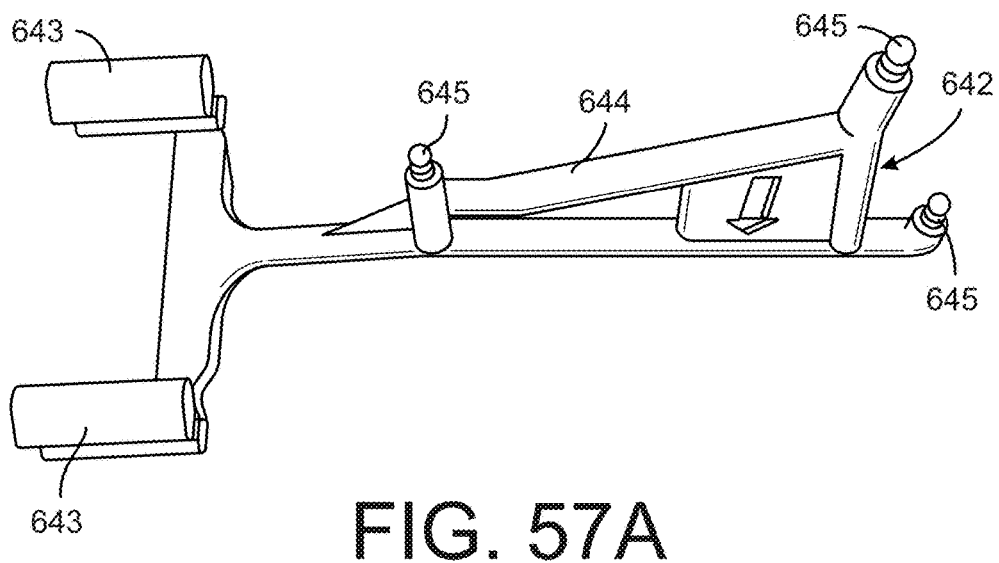
FIG. 57A
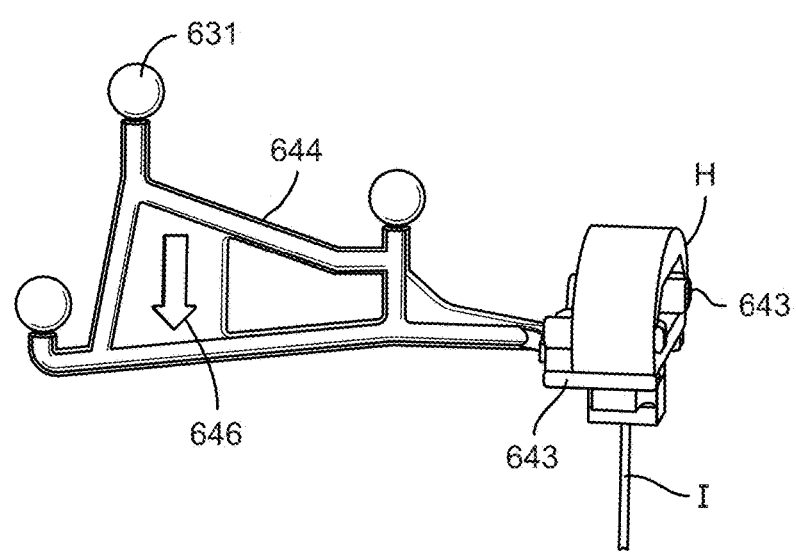 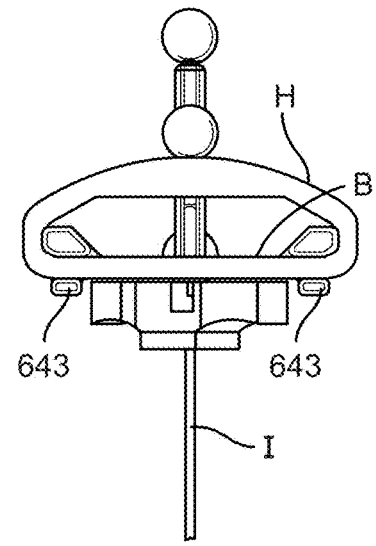
FIG. 57B    FIG. 57C

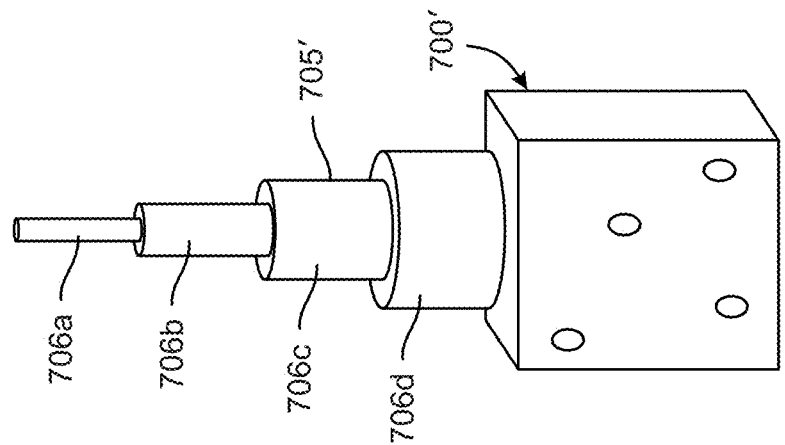
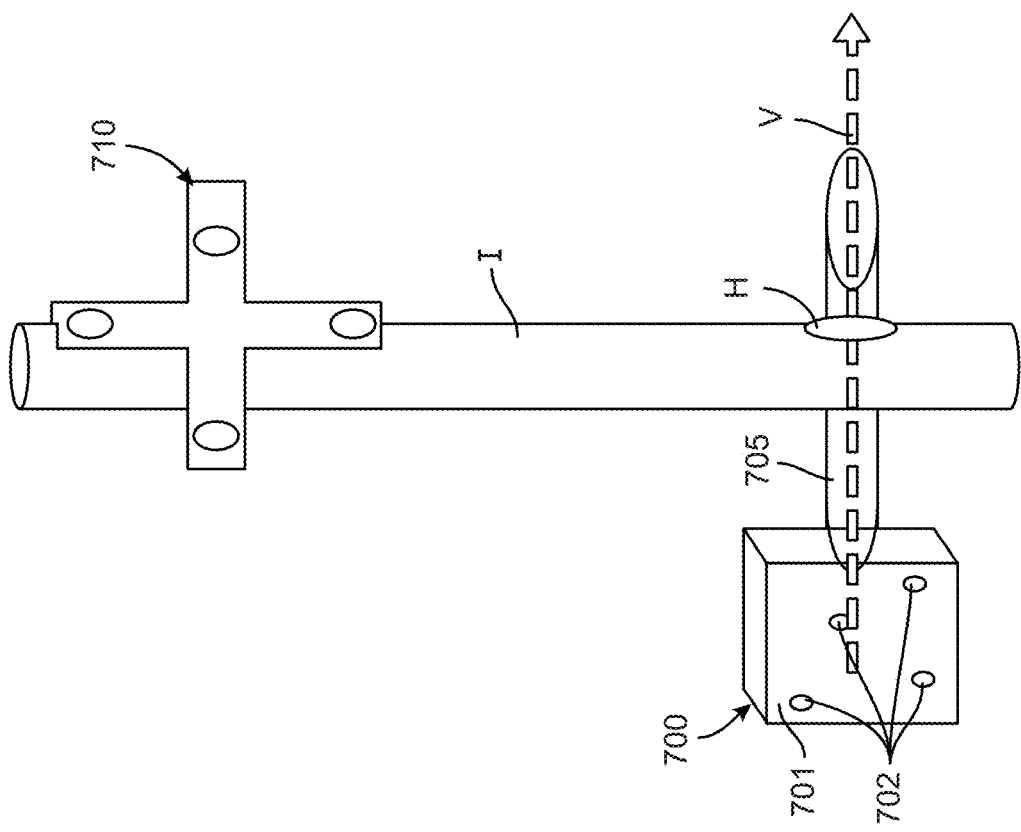

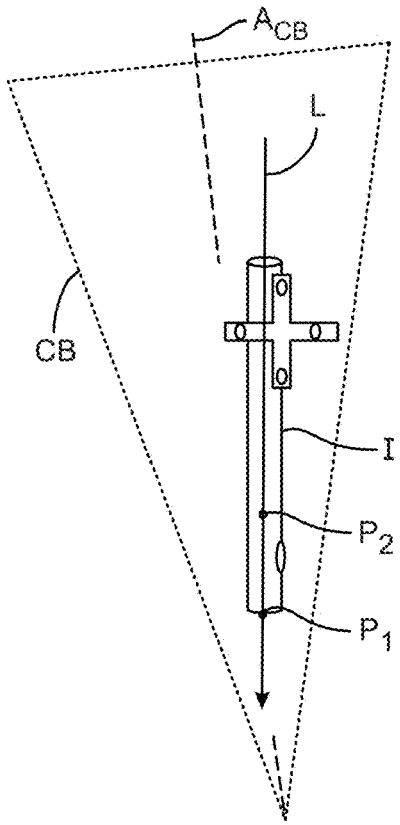
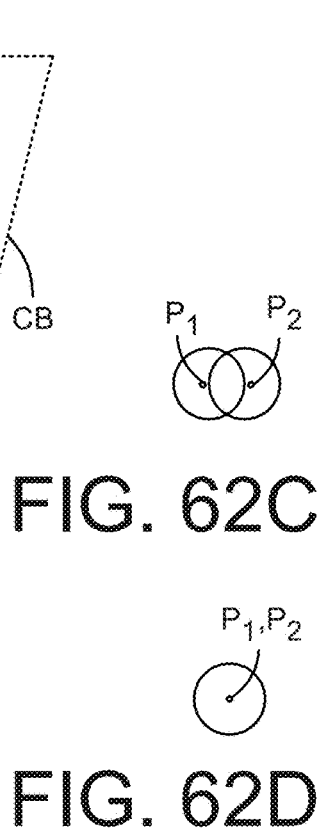
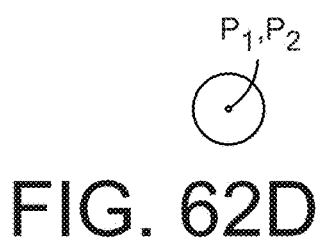
FIG. 62A  FIG. 62B  FIG. 62C  FIG. 62D
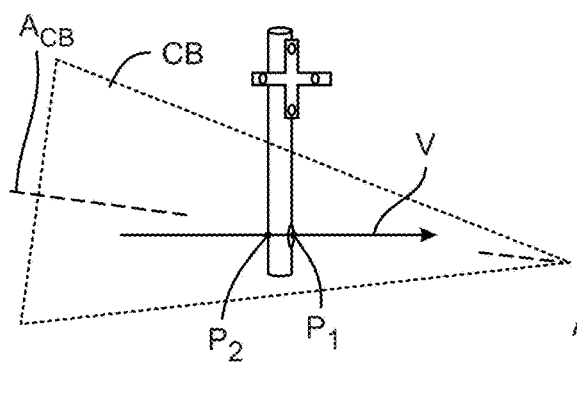
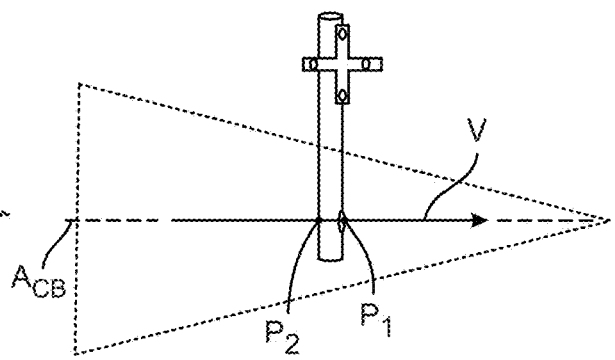
FIG. 63A  FIG. 63B
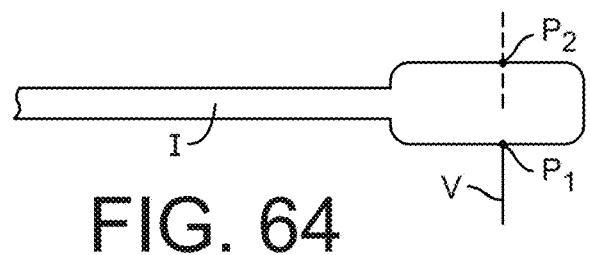
FIG. 64

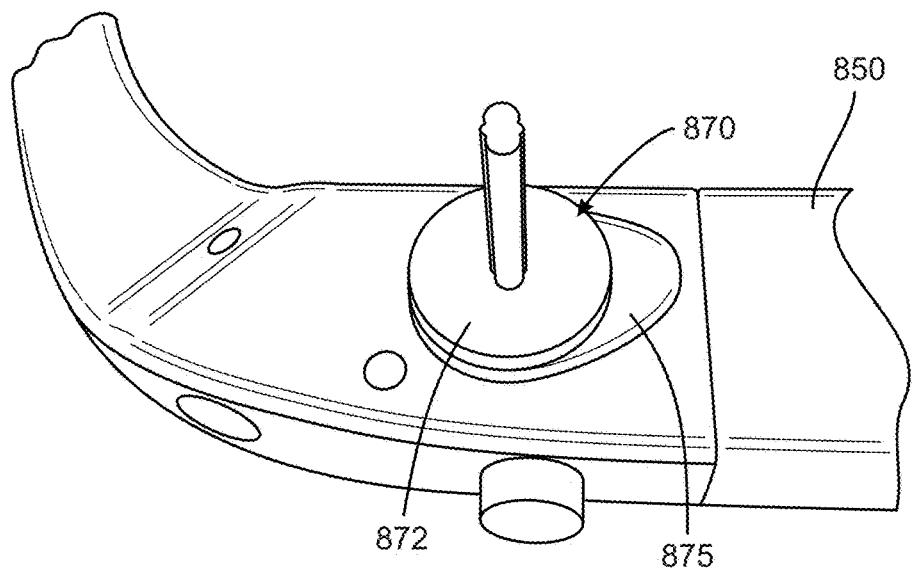
FIG. 90A
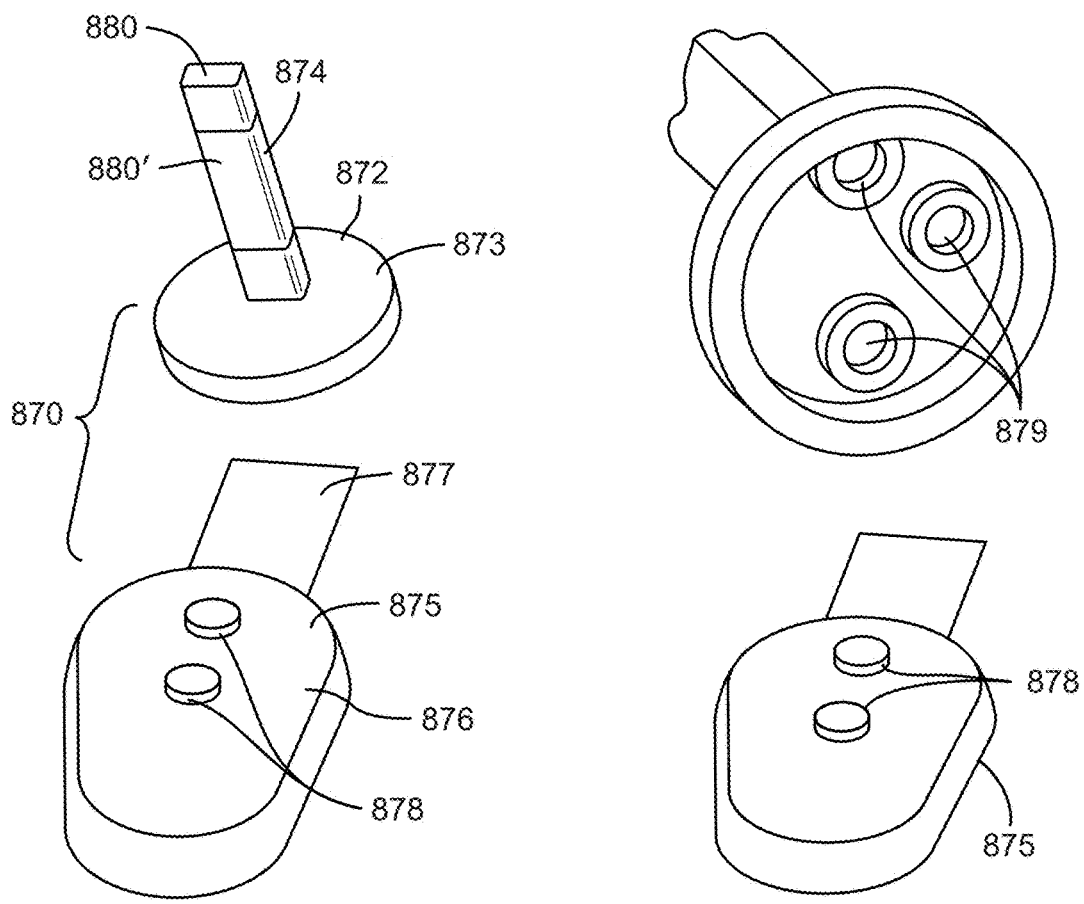
FIG. 90B
FIG. 90C

IMAGING SYSTEM AND METHOD FOR IMAGE LOCALIZATION OF EFFECTERS DURING A MEDICAL PROCEDURE

PRIORITY CLAIM AND REFERENCE TO RELATED APPLICATIONS

This application is a continuation-in-part of co-pending application Ser. No. 15/596,547, filed on May 16, 2017, which is a utility filing from and claims priority to U.S. Provisional Application No. 62/336,999, entitled "System and Method for Image Localization of Effecters During a Medical Procedure" filed on May 16, 2016, the entire disclosure of which is incorporated herein by reference, and to U.S. Provisional Application No. 62/337,010, also filed on May 16, 2006, the disclosure of which is incorporated herein by reference. This application is also a utility filing from and claims priority to U.S. Provisional Application No. 62/374,187, entitled "Detection of Tracked Radio-dense objects During Imaging", filed on Aug. 12, 2016, the entire disclosure of which is incorporated herein by reference.

BACKGROUND

Many surgical procedures require obtaining an image of the patient's internal body structure, such as organs and bones. In some procedures, the surgery is accomplished with the assistance of periodic images of the surgical site. Surgery can broadly mean any invasive testing or intervention performed by medical personnel, such as surgeons, interventional radiologists, cardiologists, pain management physicians, and the like. In surgeries and interventions that are in effect guided by serial imaging, which we will refer to as image guided, frequent patient images are necessary for the physician's proper placement of surgical instruments, be they catheters, needles, instruments or implants, or performance of certain medical procedures. Fluoroscopy, or fluoro, is one form of intraoperative X-ray and is taken by a fluoro unit, also known as a C-arm. The C-arm sends X-ray beams through a patient and takes a picture of the anatomy in that area, such as skeletal and vascular structure. It is, like any picture, a two-dimensional (2D) image of a three-dimensional (3D) space. However, like any picture taken with a camera, key 3D info may be present in the 2D image based on what is in front of what and how big one thing is relative to another.

A DRR is a digital representation of an X-ray made by taking a CT scan of a patient and simulating taking X-rays from different angles and distances. The result is that any possible X-ray that could be acquired for that patient can be simulated, which is unique and specific to how the patient's anatomical features look relative to one another. Because the "scene" is controlled, namely by controlling the virtual location of a C-Arm to the patient and the angle relative to one another, a picture can be generated that should look like any X-ray taken in the operating room (OR).

Many imaging approaches, such as taking fluoro images, involve exposing the patient to radiation, albeit in small doses. However, in these image guided procedures, the number of small doses adds up so that the total radiation exposure can be problematic not only to the patient but also to the surgeon or C-arm technologist and others participating in the surgical procedure. There are various known ways to decrease the amount of radiation exposure for a patient/surgeon when an image is taken, but these approaches come at the cost of decreasing the resolution of the image being obtained. For example, certain approaches use pulsed imaging as opposed to standard imaging, while other approaches involve manually altering the exposure time or intensity. Narrowing the field of view can potentially also decrease the area of radiation exposure and its quantity (as well as alter the amount of radiation "scatter") but again at the cost of lessening the information available to the surgeon when making a medical decision. Collimators are available that can specially reduce the area of exposure to a selectable region. For instance, a collimator, such as the Model Series CM-1000 of Heustis Medical, is placed in front of an x-ray source, such as the source 104 shown in FIG. 1. The collimator consists of a series of plates that absorb most incident X-rays, such as lead. The only x-rays that reach the patient are those that pass through apertures between the plates. The position of the plates can be controlled manually or automatically, and the plates may be configured to provide differently shaped fields, such a multi-sided field. Since the collimator specifically excludes certain areas of the patient from exposure to x-rays, no image is available in those areas. The medical personnel thus have an incomplete view of the patient, limited to the specifically selected area. Thus, while the use of a collimator reduces the radiation exposure to the patient, it comes at a cost of reducing the amount of information available to the medical personnel.

A typical imaging system 100 is shown in FIG. 1. The imaging system includes a base unit 102 supporting a C-arm imaging device 103. The C-arm includes a radiation source 104 that is positioned beneath the patient P and that directs a radiation beam upward to the receiver 105. It is known that the radiation beam emanated from the source 104 is conical so that the field of exposure may be varied by moving the source closer to or away from the patient. The source 104 may include a collimator that is configured to restrict the field of exposure. The C-arm 103 may be rotated about the patient P in the direction of the arrow 108 for different viewing angles of the surgical site. In some instances, metal or radio-dense material effecters, such as implants or instruments T, may be situated at the surgical site, necessitating a change in viewing angle for an unobstructed view of the site. Thus, the position of the receiver relative to the patient, and more particularly relative to the surgical site of interest, may change during a procedure as needed by the surgeon or C-arm technologist. Consequently, the receiver 105 may include a tracking target 106 mounted thereto that allows tracking of the position of the C-arm using a tracking device 130. For instance, the tracking target 106 may include several infrared emitters spaced around the target, while the tracking device is configured to triangulate the position of the receiver 105 from the infrared signals emitted by the element. The base unit 102 includes a control panel 110 through which a radiology technician can control the location of the C-arm, as well as the radiation exposure. A typical control panel 110 thus permits the technician to "shoot a picture" of the surgical site at the surgeon's direction, control the radiation dose, and initiate a radiation pulse image.

The receiver 105 of the C-arm 103 transmits image data to an image processing device 122. The image processing device can include a digital memory associated therewith and a processor for executing digital and software instructions. The image processing device may also incorporate a frame grabber that uses frame grabber technology to create a digital image or pixel-based image for projection as displays 123, 124 on a display device 126. The displays are positioned for interactive viewing by the surgeon during the procedure. The two displays may be used to show images from two views, such as lateral and AP, or may show a baseline scan and a current scan of the surgical site. An input device 125, such as a keyboard or a touch screen, can allow the surgeon to select and manipulate the on-screen images. It is understood that the input device may incorporate an array of keys or touch screen icons corresponding to the various tasks and features implemented by the image processing device 122. The image processing device includes a processor that converts the image data obtained from the receiver 105 into a digital format. In some cases the C-arm may be operating in the cinematic exposure mode and generating many images each second. In these cases, multiple images can be averaged together over a short time period into a single image to reduce motion artifacts and noise.

Standard X-ray guided surgery typically involves repeated x-rays of the same or similar anatomy as an effecter (e.g.—screw, cannula, guidewire, instrument, etc.) is advanced into the body. This process of moving the effecter and imaging is repeated until the desired location of the instrument is achieved. This iterative process alone can increase the lifetime risk of cancer to the patient over 1% after a single x-ray intensive intervention.

Classic image guided surgery ("IGS") uses prior imaging as a roadmap and projects a virtual representation of the effecter onto virtual representations of the anatomy. As the instrument is moved through the body, the representation of the effecter is displayed on a computer monitor to aid in this positioning. The goal is to eliminate the need for x-rays. Unfortunately, in practice, the reality of these devices doesn't live up to the desire. They typically take significant time to set-up, which not only limits adoption but only makes them impractical for longer surgeries. They become increasingly inaccurate over time as drift and patient motion cause a disassociation between physical space and virtual space. Typical IGS techniques often alter work flow in a significant manner and do not offer the physician the ability to confirm what is occurring in real-time and to adjust the instrument as needed, which is a primary reason fluoroscopy is used.

What would benefit greatly the medical community is a simple image localizer system that helps to position instruments without altering workflow. It would be substantially beneficial if the system can quickly be set-up and run, making it practical for all types of medical interventions both quick and protracted. The desirable system would significantly limit the number of x-rays taken, but does not require eliminating them. Therefore, by both encouraging reimaging and using this as a means to recalibrate, the system would ensure that the procedure progresses as planned and desired. Using the actual x-ray representation of the effecter rather than a virtual representation of it would further increase accuracy and minimize the need for human interaction with the computer. If the system mimics live fluoroscopy between images, it would help to position instruments and provide the accuracy of live imaging without the substantial radiation imparted by it.

SUMMARY OF THE DISCLOSURE

A computer-assisted imaging localization system is provided that assists the physician in positioning implants and instruments into a patient's body. The system has the desired effect of displaying the actual instrument or implant and using this displayed to guide surgery without the need to directly interact with the computer. The system does so by displaying and moving overlapping images on a computer screen, allowing one image to be seen through the other. These image "masks" can be the unaltered image or doctored images to intensify or mitigate the anatomical or non-anatomical aspects of the image. Sliding these images over one another can help to position medical devices with a high degree of accuracy with a limited number of additional x-rays.

In another feature, tracking elements are provided for a surgical tool or instrument having an elongated shaft and a working tip that allows the instrument or tool to be tracked by an optical tracking associated with the imaging localization system. In one embodiment, the tracking element includes a cylindrical body configured to clamp onto the elongated shaft of the tool or instrument and at least one concentric band at least partially encircling the outside surface of the cylindrical body, the at least one concentric band adapted to be detected by an optical localizer or an optical detection device associated with an x-ray imaging system. Other tracking elements are provided that allow tracking of the instrument or tool in all degrees of freedom of movement to allow accurately locating the instrument and its working tip relative to the anatomy in the surgical field.

In another feature, a calibration device is provided for calibrating the position of a C-arm radiation machine having a detector in a detector housing and an imaging ray source in a source housing. The device includes a calibration collar configured to be mounted on a detector housing of the C-arm, the collar including an end face configured to be mounted flush with the end face of the detector housing, the end face defining a central opening for passage of the imaging ray from the source to the detector. The calibration collar further includes a plurality of glyphs, uniquely configured in relation to each other, mounted to the calibration collar within the central opening, the plurality of glyphs formed of a radio-opaque material.

A calibration device is also provided for calibrating the position of a C-arm radiation machine having a detector in a detector housing and an imaging ray source in a source housing, the device including a cap configured to be mounted over the source housing, the cap including a plate configured to be seated flush with the face of the source housing when the cap is mounted thereon, said plate defining an opening aligned with the transmission path of the imaging ray from the imaging ray source. The calibration device further includes a plurality of glyphs that extend into the opening so that the glyphs intersect the beam transmitted by the imaging ray source.

DESCRIPTION OF THE DRAWINGS

FIGS. 3A-D are screen shots of image displays of a surgical site showing the patient's anatomy and a movable image of a radio-dense effecter in relation to a fixed image of the surgical site.

FIGS. 4A-C are screen shots of x-ray images of a surgical site and radio-dense effecter, including a low dose x-ray image and an image in which the display of the radio-dense effecter is enhanced relative to the image of the anatomy.

FIGS. 12A-C are screen shots of low dose x-ray images showing images of radio-dense effecters.

FIGS. 14A-E are a series of screen shots of an x-ray image in which the radio-dense effecters are automatically detected by the image processing device of the present disclosure.

FIG. 29A is an image of a surgical field acquired using a full dose of radiation in the imaging system.

FIG. 29B is an image of the surgical field shown in FIG. 29A in which the image was acquired using a lower dose of radiation.

FIG. 29C is a merged image of the surgical field with the two images shown in FIGS. 29A-B merged in accordance with one aspect of the present disclosure.

FIG. 32A is an image of a surgical field including an object blocking a portion of the anatomy.

FIG. 32B is an image of the surgical field shown in FIG. 32A with the image of FIG. 32A partially merged with a baseline image to display the blocked anatomy.

FIGS. 33A-B are displays of the surgical field adjusted for movement of the imaging device or C-arm and providing an indicator of alignment of the imaging device with a desired trajectory for acquiring a new image.

FIG. 35A is an image of a surgical field obtained through a collimator.

FIG. 35B is an image of the surgical field shown in FIG. 35A as enhanced by the systems and methods disclosed herein.

FIGS. 54A-54D are perspective views of tracking elements according to further embodiments.

FIGS. 57A-57C are views of another tracking element, including two views of the tracking element mounted on an instrument.

FIGS. 61A-61B are perspective views of a calibration tool for calibrating the position of a hole in an instrument.

FIGS. 62A-62D are diagrams illustrating a method for aligning an X-ray device along a longitudinal axis of an instrument.

FIGS. 63A-63B are diagrams illustrating a method for aligning an X-ray device along a transverse axis of an instrument.

FIG. 64 is a side view of an instrument having an enlarged working end for application of the alignment method shown in FIGS. 63A-63B.

FIGS. 90A-90C are views of a tracking element removably mounted to the nail guide shown in FIGS. 87A-87B.

DETAILED DESCRIPTION

Figure 1:
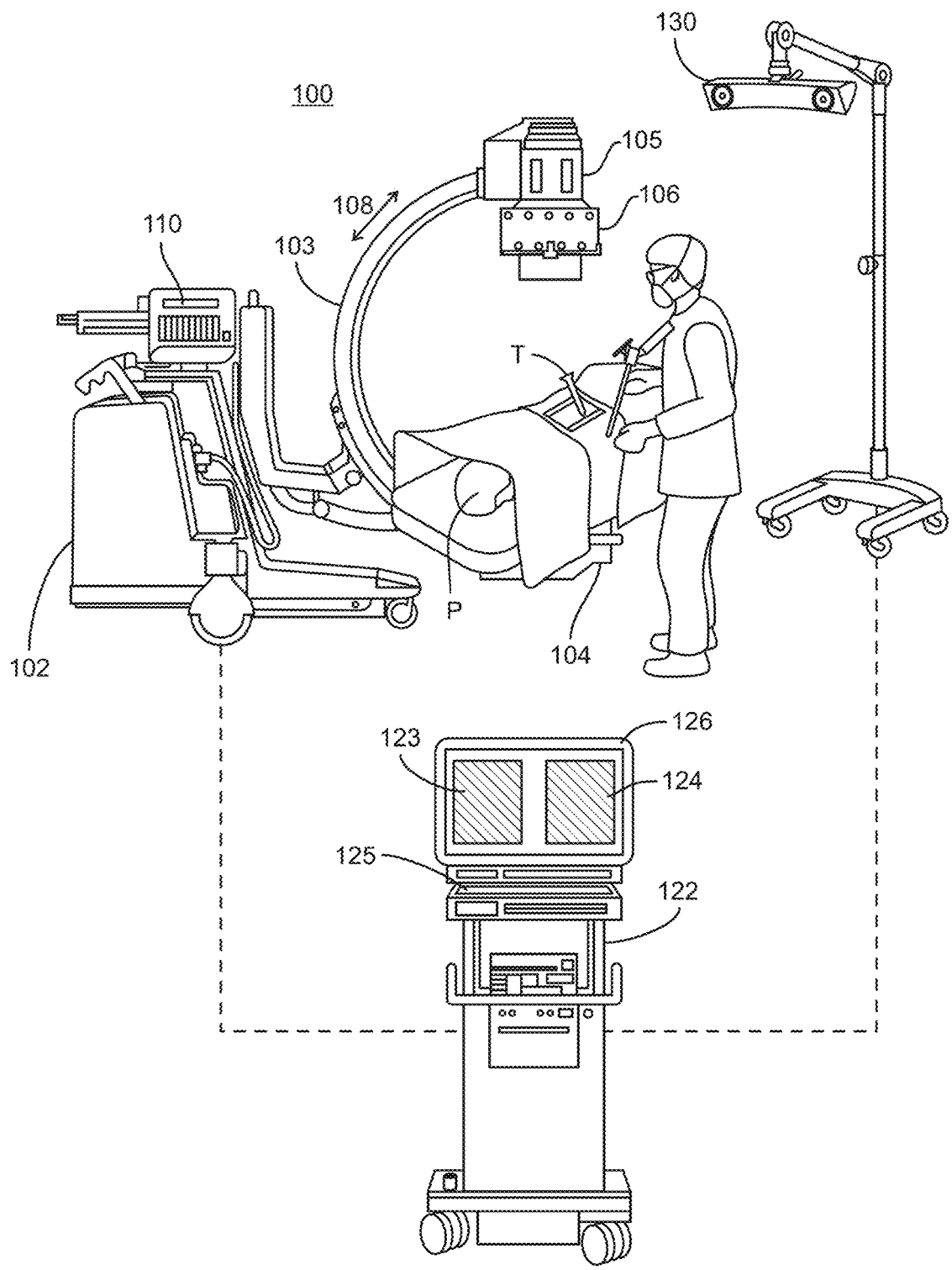
FIG. 1 is a pictorial view of an image guided surgical setting including an imaging system, an image processing device and a localizer or tracking device for surgical instruments and devices.

For the purposes of promoting an understanding of the principles of the disclosure, reference will now be made to the embodiments illustrated in the drawings and described in the following written specification. It is understood that no limitation to the scope of the disclosure is thereby intended. It is further understood that the present disclosure includes any alterations and modifications to the illustrated embodiments and includes further applications of the principles disclosed herein as would normally occur to one skilled in the art to which this disclosure pertains.

According to one aspect of the invention, the process begins with taking an image of the anatomy to be addressed surgically. Typically this "localizing shot" or "baseline image" does not contain the radio-dense effecter (e.g.—screw, cannula, guidewire, instrument, etc.) that is to be moved/adjusted, although in one embodiment a single image containing the effecter can be used. The image processing device 122 (FIG. 1) generates a digital image that can be displayed and manipulated digitally. With the anatomy identified and displayed on a computer screen, a "new" image with the effecter or instrument is taken, with this image also converted to a digital image by the image processing device 122. This new image is displayed on top of the original localizing shot so that the resulting image looks like the conventional image on a fluoroscope screen, such as shown in FIG. 3A. In one aspect of the present disclosure, the effecter, such as effecter T in FIG. 1, incorporates a localizer system (e.g.—EM, Optical IGS, etc) capable of tracking movement of the effecter. The 3D movement of the effecter measured by the localizer system can be applied to the digital representation of the "new" image relative to move the "new" image relative to the "localizing shot" image. Thus, as the tip of the effecter is tracked, the movement of the "new" image shows the change in position of the tip of the instrument being tracked relative to the stationary anatomy depicted in the "localizing shot". On the computer screen, it thus appears as if live fluoroscopy is being taken as the effecter is being moved and as if the actual tool or implant is being moved and adjusted relative to the patient's anatomy. When the next image is taken, the tip of the effecter is at the location that the physician desires. It can be appreciated that unlike the typical IGS system in which a digital model of the effecter is manipulated, the system and method of the present disclosure relies on manipulating an actual image of the effecter in the surgical field.

Figure 2:
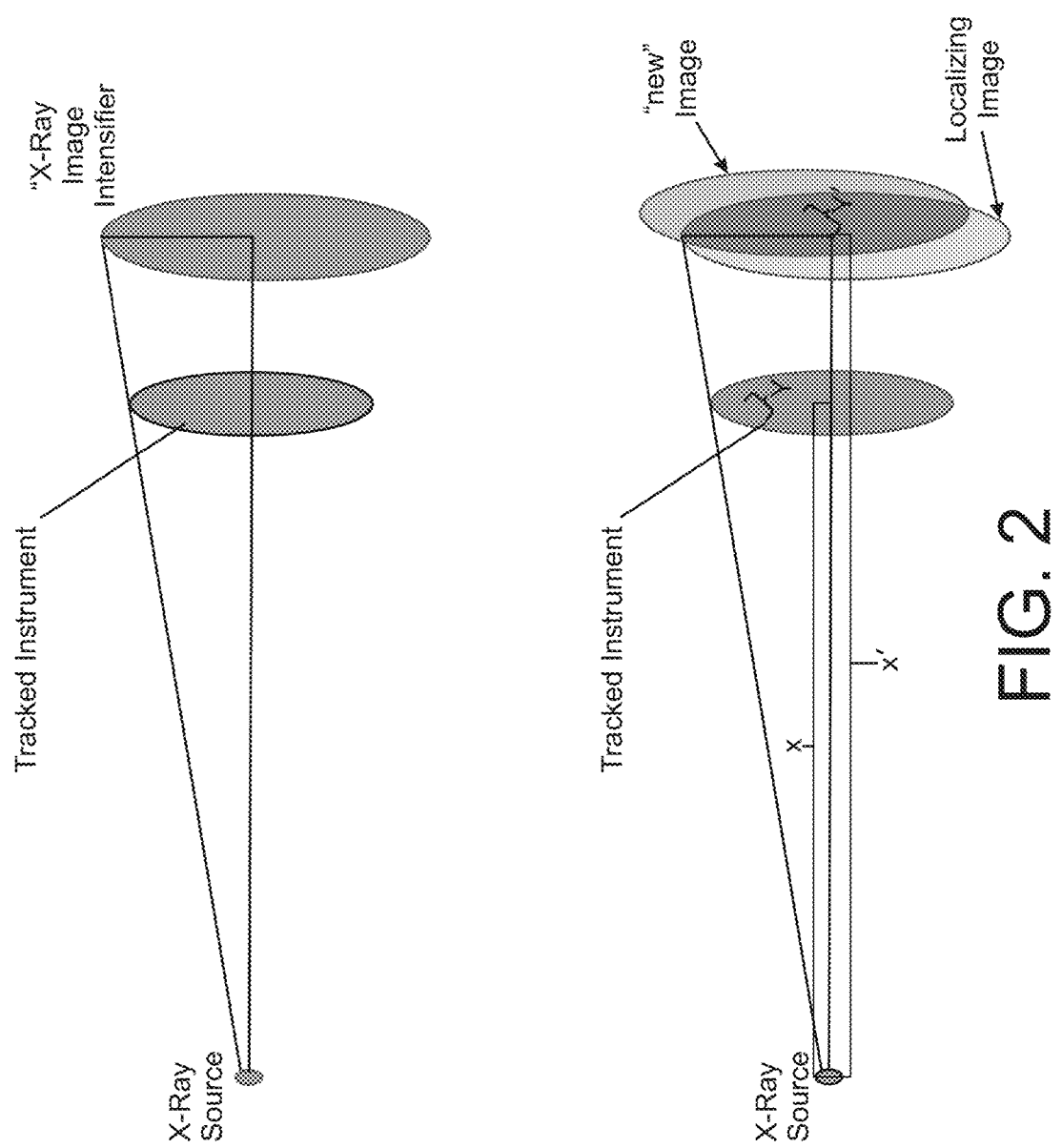
FIG. 2 is a diagram of steps in displaying movement of a tracked effecter on an x-ray image of a surgical site.

The movement of the "new" image on the display is based on the geometry of the tip of the effecter relative to the location within the cone beam of the fluoroscope, as depicted in FIG. 2. The nearer the tip of the tracked effecter is to the x-ray source, for the same relative movement, the greater the movement of the "new" image and therefore the effecter's projection (in pixels) relative to the size of the "localizing shot". Assuming a standard size image, such as a 9 in. image intensifier, and assuming a typical 1000 mm separation of the x-ray source from the intensifier, there is an approximate 2.24 pixel per mm movement of the tracked effecter projected on the image intensifier. Away from the image intensifier and closer to the source, this pixel-per-mm movement ratio is magnified in a consistent manner as shown in FIG. 2. In particular, the movement distance of the projection of the tracked effecter on the image intensifier is given by $Y'=X'*Y/X$, where Y is the actual movement distance of the effecter, X is the distance from the source to the tracked effecter/instrument, X' is the distance from the source to the localizing image at the image intensifier and Y' is the projected movement distance. It can be appreciated that the distance X' is typically fixed throughout the procedure for a conventional C-arm X-ray source. The distance X and the movement distance Y can be determined by the image processing device 122 (FIG. 1) based on data received from the localizer system used to track the movement of the effecter. The image processing device uses the projected movement distance Y' to move the "new" image accordingly on the display.

The "new" image, shown in the lower representation in FIG. 2, can be taken using standard x-ray settings, or may be taken using less than full dose radiation or low dose settings which has the benefit of blurring out the anatomy while having relatively little impact on the image of a metal or radio-dense material effecter in the image. (It is understood that a "radio-dense" material generally does not allow the imaging rays or x-rays to pass through so that the radio-dense effecter blocks the underlying anatomy). When the "new" image is a low dose image, the "new" image can be combined with or overlaid on the image from the localizing shot allowing the user to see the resulting combined image with the appearance of the anatomy appearing as a live fluoroscopic image. The result is an image as seen in FIG. 3A that can help guide an effecter to the correct location desired by the physician.

In the example shown in FIGS. 3A-D, a bone screw 10 to be tracked is introduced into a patient after an initial "localizing shot" and projected on the display 122/123 (FIG. 1) as the screen shot of FIG. 3A. As the tracked instrument 10 is moved out of the field of the localizing shot or baseline image 12, as depicted in the screen shot of FIG. 3B, the two overlapping images can be appreciated, with the localizing shot 12 seen to the left and the new low radiation image 14 to the right. It can be noted that the metal screw in the low radiation image is very prominent while the representation of the anatomy is obscure. When the tracked screw is moved into an ideal location based on the desire of the physician, such as shown in the screen shot of FIG. 3C, the image on the screen can constantly project a combined image (overlaying the full dose localizing shot with the low dose image) that replicates what a new fluoroscopic image would look like at any point, mimicking live fluoroscopy without obtaining a new live image. It can be appreciated that the localizing or baseline image 12 does not change as the effecter 10 is moved, at least so long as the C-arm or X-ray source is not moved. Thus, the digital data for the localizing image 12 is not manipulated by the image processing device during movement of the effecter. On the other hand, the image processing device does manipulate the digital data of the "new" image based on the projected movement of the tracked effecter so that the "new" image moves across the display as the effecter is moved.

A stationary full dose new image can be taken, such as the display in the screen shot of FIG. 3D, to confirm that the effecter 10 is in the location desired by the physician. If for some reason the image alignment is off or further fine tuning is required, this newly acquired image can replace the prior localizing shot image as the baseline image, and the process is repeated. The system thus resets or recalibrates when the full dose new image is taken, so that subsequent images are always more accurately displayed than previous ones.

It can be appreciated that as the physician moves the effecter 10 the low dose image moves with the effecter. When the effecter is within the field of the baseline or localizing shot image, as in FIG. 3C, the image of the effecter from the low dose image is combined with the stationary localizing image so that the physician can clearly see the patient's anatomy and the effecter's position relative to that anatomy. As the effecter is moved within the field of the baseline image, the image of the effecter (and the "new" image) moves accordingly so that the physician can guide the tip of the effecter to the desired position in the anatomy. In recognition that a new image is not actually being acquired during each step of movement of the effecter, the physician can acquire new low dose images at various stages of movement of the effecter to verify the actual location of the effecter. Thus, any error in the actual vs. displayed position of the effecter relative to the anatomy is eliminated with each new low dose image taken. In other words, with each low dose image, the system recalibrates the actual position of the effecter relative to the anatomy based on the digital data acquired from the low dose image. The new data identifying the new position of the effecter is then the starting point for movement of the new image as the effecter is moved by the surgeon. It is contemplated that the physician may require multiple low dose images as the effecter is moved into its final position, with each low dose image recalibrating the actual position of the effecter, potentially culminating in a full dose image to verify the final position.

In one modification, rather than overlaying a low dose image of the effecter and anatomy over a full dose image, the present disclosure contemplates overlaying the acquired full dose image over itself as the effecter is moved in the surgical field. The moving full dose image can be modified to be more translucent than the underlying full dose image, such as by reducing the pixel intensity of the image. The effecter will inherently be darker and more visible than the anatomy visible in either of the full dose images, so reducing pixel intensity will not significantly affect the ability to view the effecter as it is moved in the surgical field. As with the low dose image, this aspect of the present disclosure contemplates moving the modified full dose image as the effecter is moved. In particular, the movement of the effecter is tracked with a tracking device 130, as described in more detail herein. As the tracking device detects the new position of the effecter, the present system moves the overlaid full dose image consistent with the movement of the effecter, since the relationship between the image pixels representing the effecter have a fixed relationship to the pixels representing the anatomy in the moving full dose image. As with the lose dose overlaying image described above, the surgeon can manipulate the effecter within the surgical field and have an immediate image of where the effecter is relative to the actual fixed anatomy depicted in the full dose image. A new full dose image (or even low dose image) can be acquired at any point in the movement of the effecter to recalibrate the image.

In one aspect, each new low dose image can be processed according to the techniques described U.S. Pat. No. 8,526,700 (the '700 patent), which issued on Sep. 3, 2013, the entire disclosure of which is incorporated herein by reference. As described in more detail in the '700 patent a full dose image is manipulated into a multitude of orientations, with an image of each of the orientations stored in memory. The low dose image is compared to these multitude of stored images to find a "full dose" image that matches the current low dose image. The new low dose image is then merged with the extracted full dose image to produce a display that simulates an actual full dose image. It can be appreciated that this new merged image is only of the anatomy; however, the actual low dose image showing the effecter can be overlaid on the new "full dose" image, as described above. The presence of the effecter in the low dose image used to obtain the new merged image can be accounted for as described in the '700 patent and in further detail herein.

Although a low radiation image is shown in FIGS. 3A-D, a conventional or full dose "new" image can be taken and displayed with similar results, as shown in the screen shot of FIG. 4A. A low radiation image can be used, as see in the screen shot of FIG. 4B, or a metal intensification of the "new" image can be performed as shown in the screen shot of FIG. 4C. The image of FIG. 4B is obtained under low radiation so that the anatomic features are effectively washed out. While the image of the effecter 10 is also washed out due to the low dosage, the metal or other radio-dense material is sufficiently radiopaque so that the resulting image of the effecter in FIG. 3B is still outstanding enough to be easily seen.

The image of FIG. 4C is generated by intensifying the pixels associated with the image of the effecter 10, so that when the full image is displayed the image of the effecter essentially washes out the image of the underlying anatomy. In either case, what is projected has the ability to "fool the eye" to make it appear to the surgeon as if the instrument is moving under live fluoroscopy.

Figures 5A, 5B, 5C:
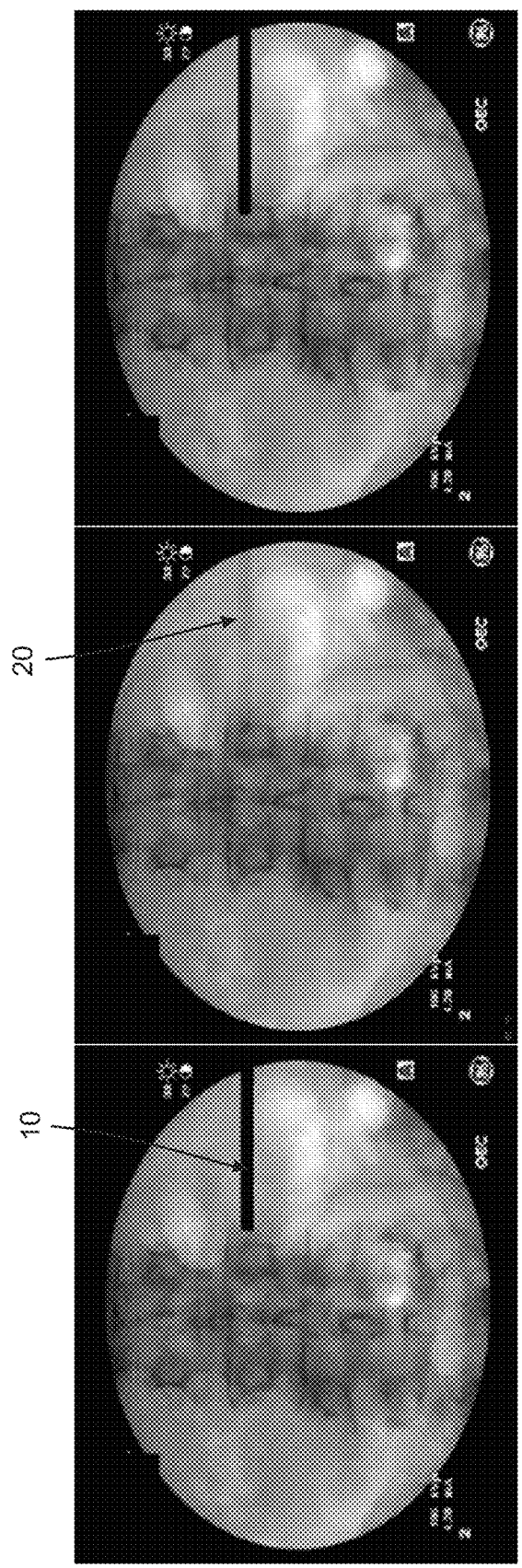
FIGS. 5A-C are screen shots of x-ray images in which the radio-dense effecter is represented by a metal mask in an image that moves relative to the fixed image of the surgical site as the effecter moves.

The metal intensification image of FIG. 4C can constitute a metal mask applied to the images, such as the image in the screen shot of FIG. 5A. As shown in FIG. 5B, the image of the effecter 10 is represented by a green mask 20 overlaying the actual image. The movement of the mask is correlated to the actual movement of the effecter as determined by the localizer. When the green layer of the mask 20 is moved to a more ideal location, a confirmatory x-ray can be taken as in the screen shot of FIG. 5C. The green or metal mask 20 can be generated by the image processing device 122 (FIG. 1) using software that examines the pixels of the image to determine which pixels are associated with anatomic features and non anatomic features based primarily on the intensity value of each pixel. Various filters can be applied each pixel of the digitized X-ray image to enhance the edges between pixels representing anatomic and non-anatomic features. Once the pixels associated with the non-anatomic features are acquired and the edges enhanced, the pixels outside the selected non-anatomic pixels can be washed out, leaving only the pixels for the non-anatomic feature corresponding to the effecter.

Figure 6A:
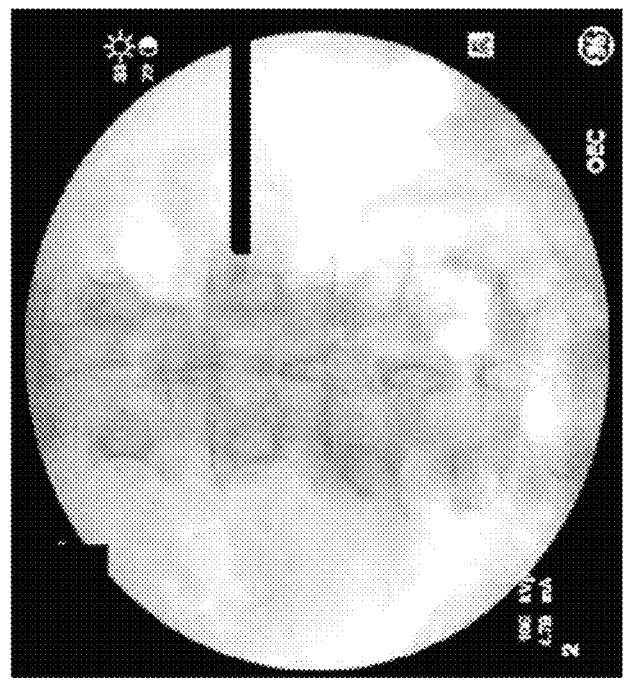
FIGS. 6A-B are screen shots of x-ray images of the surgical site with an overlaying metal mask image of the effecter.
Figure 6B:
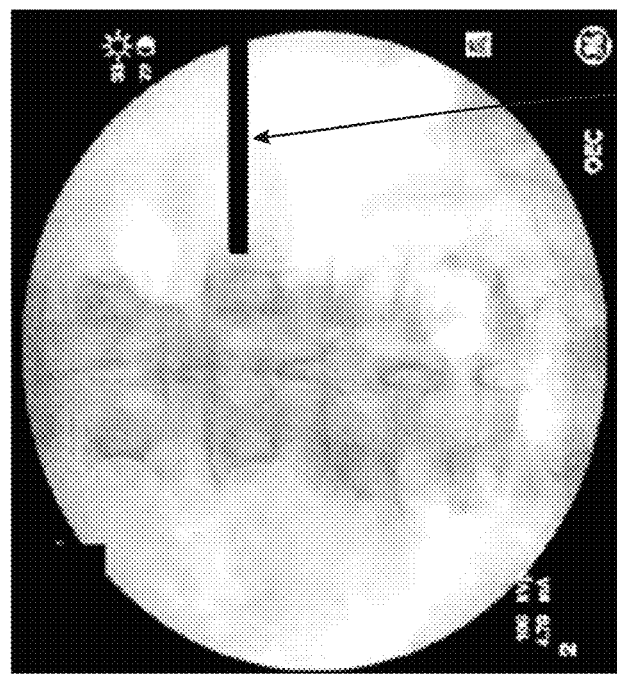

Similar to the images of FIGS. 5A-C, image tracking can be applied in FIGS. 6A-B to a Jamshedi needle 10' that is repositioned to a desired position in the patient's body. However, in FIG. 6A there is no initial "localizing shot". The "new" image serves as both the stationary and the moved image. The image of the effecter is replaced by a green layer mask, such as the mask 20 of FIG. 5C, and just the green layer of the image is moved on the background of the "new" image. The image guidance system of the effecter can determine the relative location of the instrument in the image, so that rather than moving the entire image as in the prior examples, only a narrow area around the region of the effecter 10' is moved.

The present invention contemplates a system and method for moving image masks or overlapping image sets based on the movement of a tracked object, which provides the physician or surgeon with the ability to place a surgical effecter at the correct location inside a patient with a minimal number of X-ray images. Movement projection is not based on the absolute motion of the effecter but rather on the relative motion of the tracked effecter within the imaging space. Although knowledge of the absolute location of the tip of the effecter is needed for certain image movements, such as shown in FIG. 6B, such knowledge is not necessary. It is only necessary to know the relative motion between the original position and the new position of the effecter, and the distance from the tip of the effecter/instrument to the X-ray source.

The position of the effecter/instrument is recalibrated on each new X-ray shot. On the instrument side this means that each x-ray resets the relative position or the initial starting point of the "new" image to the current location of the tracked effecter to which is linked a "new" image with that effecter in it. This feature makes the system mostly focused on relative movement so that the potential time horizon for drift to set in is minimized.

The system and method disclosed herein creates "pseudo-live fluoroscopy", meaning that the physician/surgeon can see the movement of the effecter/instrument in real-time without constant imaging of the patient. The present disclosure further contemplates automating taking images to create constantly re-updated spot images with "pseudo-live fluoroscopy" in between to create a continuous high accuracy instrument tracking device with a live fluoroscopy appearance with dramatically fewer images and resulting radiation. The methods of the present disclosure only require knowledge of relative movement (meaning the delta between the last position of the instrument to the current) and only require displaying the 2D motion of the effecter/ "new" image to make this functional. The present disclosure provides a more comprehensive imaging system compared to typical IGS where it is necessary to know the absolute movement and the actual knowledge of what is being moved (in order to project a correct virtual representation of it).

The system and method of the present invention works with a metal mask or an actual image, and can work with low dose images or full dose images. With this system, the entire image can be moved or adjusted, as shown in FIGS. 3, 4, or only a region of interest is moved or adjusted, as shown in FIG. 6B.

The system and method disclosed herein uses the actual effecter (or more specifically an active x-ray picture of the effecter), not a virtual representation of it as in a typical IGS. This approach makes it possible to emphasize or deemphasize different features (e.g.—anatomy, metal, etc) of the two images to aid in visualization. The methods disclosed herein do not require distortion correction or dewarping, or a calibration phantom, as is often required in typical IGS. Thus, the present system does not require a grid on the c-arm to correct for the various types of distortion (i.e.—pin cushion, etc.). When an IGS system is being used, the present system permits the IGS tracker to be either placed at the tip of the effecter (in the case of an EM microsensor or the like) or projected to the tip by a known offset that is more typical of an optical system. The present system does not require any patient reference, such as a "beacon" that is standard on nearly all IGS systems. In particular, it is not necessary to know the location of the object's tip relative to the c-arm (the distance of the tip between the image intensifier and the x-ray source) and the in plane movement (distance and trajectory) of the effecter The present system and method can operate with a single image, separating metal or radio-dense material from anatomy and leaving the anatomy without the radio-dense material as a layer, or the radio-dense material can be moved without anatomy as a layer, as depicted in FIGS. 5, 6, or the layers can be moved in any combination.

The present method and system even works with distorted IGS data (like is classically a problem with EM), as the movement won't be perfect but will asymptotically get closer to the correct position. For instance, if the IGS data is inaccurate by 20%, then after the first movement, a "new" x-ray will confirm that it is 20% off. However, the system is then recalibrated so that now moving the new "new" image is not only more accurate, but the distance needed to move is only $\frac{1}{5}^{th}$ the prior distance. Thus, even if the system still has a 20% error, the next movement to close the gap of this 20% will be only 4% off (i.e., 20% of 20%). The use of relative motion and this perpetually smaller distance moved between each x-ray allows the present system to use noisy warped EM data for application in the OR.

Figure 7:
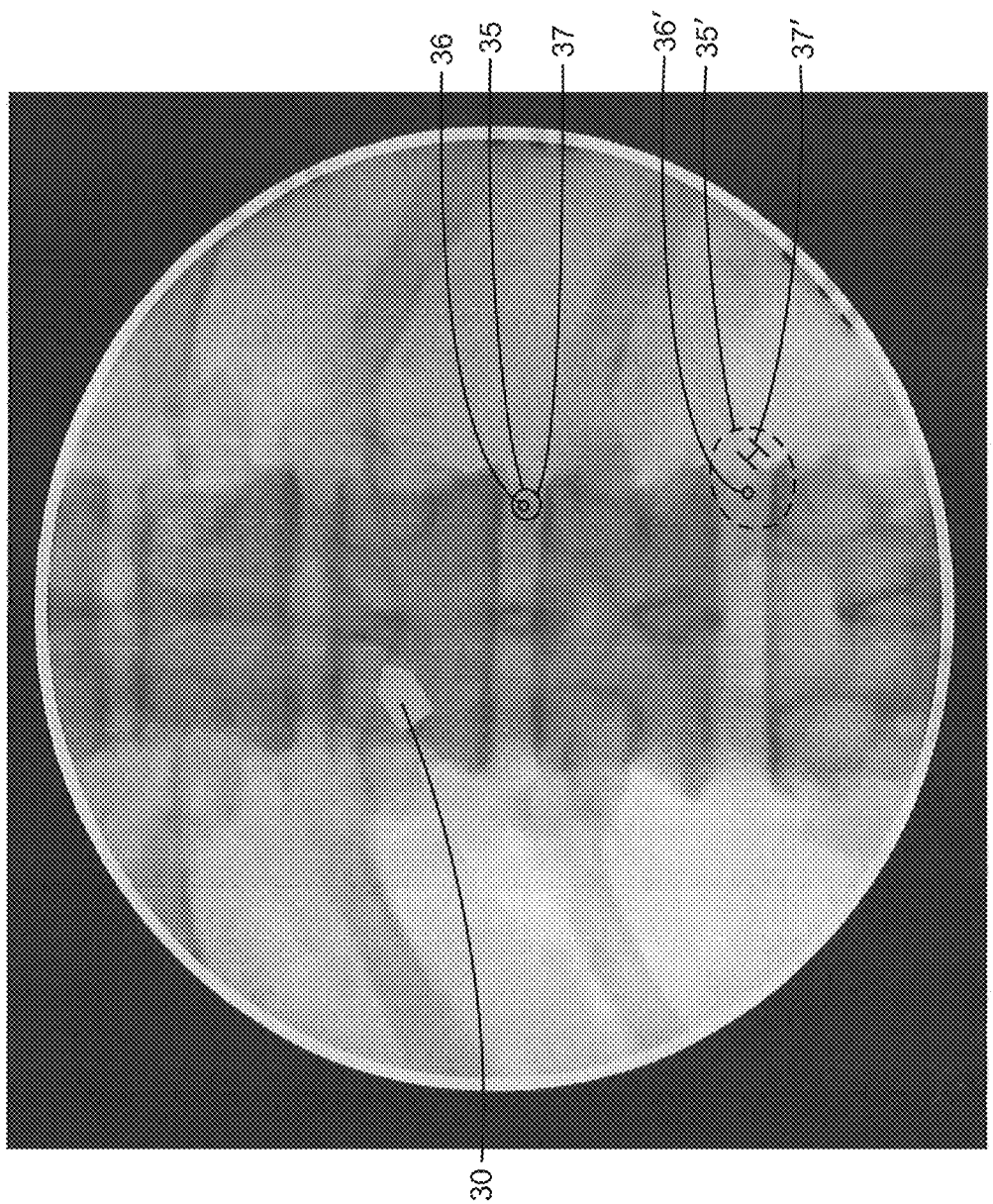
FIG. 7 is a screen shot of an x-ray image with slugs indicating the position of the tip of radio-dense effecters relative to the anatomy shown in the image.

In another feature, the tip of the effecter, such as effecter 10, can be represented on the displayed x-ray image as a slug 30 shown in the screen shot of FIG. 7. The position of the slug can correspond to the position of the tip of the effecter relative to the anatomy and can take various forms, including a circle or bulls-eye and an arrow, as depicted in FIG. 7. The appearance of the slug 30 can be varied to signify different conditions in the process of navigating the effecter to the desired anatomical position. For instance, the size or configuration of the slug can be indicative of the degree of accuracy associated with the particular movement. For example, the slug can be depicted as a circle when the accuracy is lower and an arrow when the accuracy is greater. The size of the circle can be related to the degree of accuracy for the location of the tip of the effecter.

The color of the slug can be also varied to indicate certain conditions, namely conditions of the C-arm or x-ray device. For example, the slug can be green if the current position of the C-arm is within a narrow range of its position, 2 mm for instance, when the localizing image was acquired, and red if the current position is outside that range. When the slug changes from green to red the physician can obtain a new x-ray image to establish a new baseline and verify the actual current position of the effecter. As long as the color of the effecter remains green the physician can have confidence that the actual location of the effecter tip corresponds to the displayed location. As an alternative to changing color, the slug 30 can flash if the position of the C-arm has changed.

In the case where multiple effecters are present in a surgical site, the color of the slug 30 can be indicative of the particular effecter associated therewith. It should be appreciated that all of the steps discussed above can be implemented for multiple effecters for accurate navigation of the effecters to a desired position. It can be expected that the multiple effecters may require positioning and re-positioning during a procedure, so methods of the present disclosure can be modified accordingly to account for multiple effecters and multiple slugs.

In another embodiment, a slug 35, shown in FIG. 7, marking the location of the tip of the effecter can include a central element 36, in the form of a dot or small circle, corresponding to the position of the tip, and a second element 37, in the form of a circle that is at least initially concentrically disposed around the central element 36. The second element in the form of a circle can correspond to a point on the effecter offset along the longitudinal axis of the effecter from the tip. The location of the second element or circle 37 relative to the central element or dot 36 provides the physician with an indication of the attitude of the effecter. In the depiction of FIG. 7, the offset of the circle 37 relative to the dot 36 indicates that the shaft of the associated effecter extends to the left and downward in the surgical field.

In an alternative embodiment, a slug 35' can include the same first element in the form of a dot or small circle 36' depicting the position of the effecter tip, as shown in FIG. 7. However, rather than include a circle for the second element, the second element of the slug 35' is an "I" that not only indicates the orientation of the effecter relative to its tip, but also indicates the rotation about the axis of the effecter. The angular offset of the "I" from a vertical orientation provides the surgeon with a visual indication of the rotational orientation of the implant, tool or instrument.

Figure 83A:
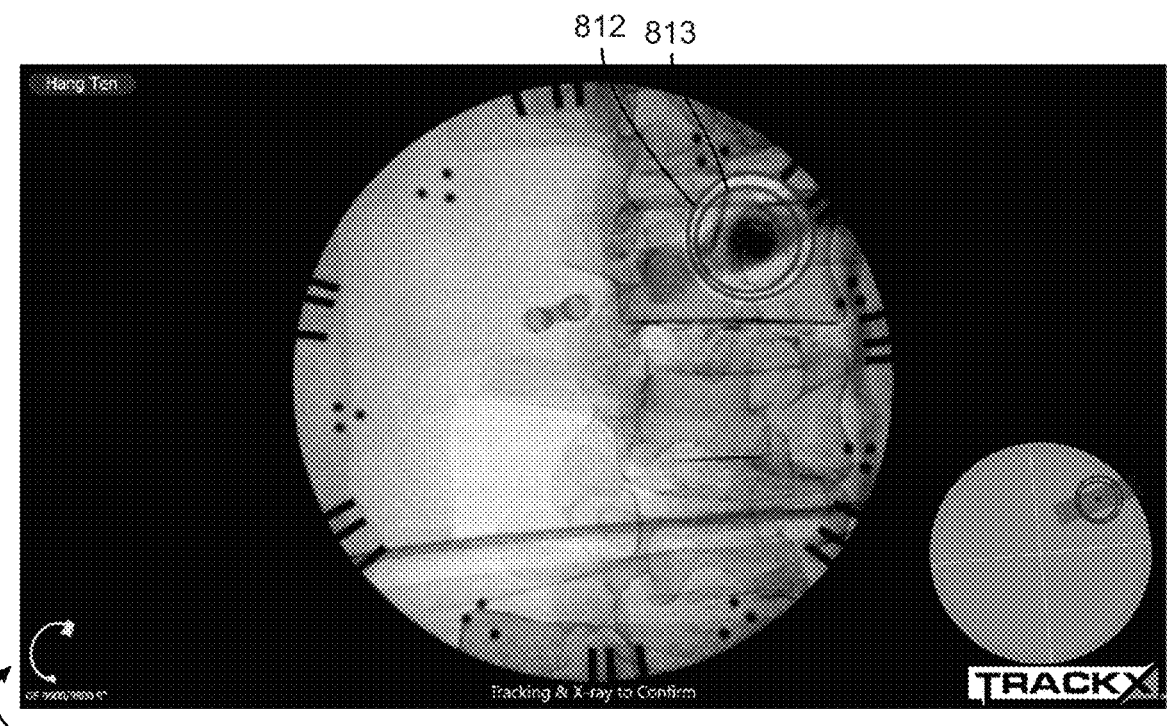
FIGS. 83A-83B are x-ray images showing an X-ray alignment method according to one aspect of the present disclosure.
Figure 83B:
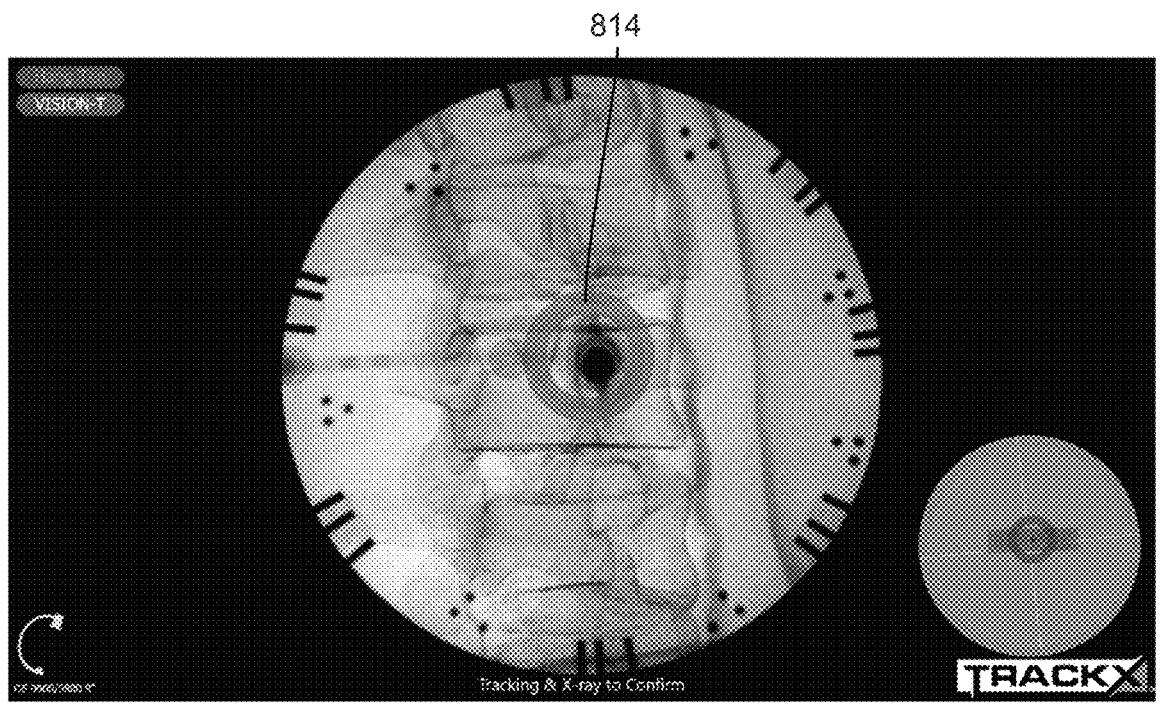

A further alternative embodiment is shown in FIGS. 83A, 83B, which are screen shots from a display occurring interactively as a surgeon manipulates an instrument at the surgical site. The instrument can be, for instance, a drill or a bone screw to be threaded into the vertebral bone pictured in the X-ray image. In this image, the X-ray is oriented along a desired line of insertion of the instrument/tool/implant into the bone, as indicated by the C-arm icon 810 at the lower left of the display. The orientation of the icon is a visual indication to the C-arm technologist/surgeon of the actual orientation of the C-arm as the X-ray image is taken. The orientation information is derived from the detection of tracking markers on the C-arm, or on components attached to the C-arm, such as the calibration collar 750 shown in FIGS. 67-74 and described in more detail herein. The surgeon thus knows that a properly oriented instrument/tool/implant will have its longitudinal axis directly aligned with the X-ray line of site. The present embodiment contemplates concentric circles 812, 813 that are actuated in a specific manner depending on the closeness of the actual orientation of the instrument to the proper alignment. The image processing device is configured and operable to activate the concentric circles only when the instrument is within a pre-defined range of proper alignment. In one specific embodiment, the pre-defined range can be within 5 degrees of the exact alignment. The position and alignment of the instrument can be determined using tracking elements as described in more detail herein. The tracking elements are detected by the tracking device 130 and the image detection device 122 is programmed to determine the position of the working end or tip of the instrument along with its physical orientation in system space, and more particularly its physical orientation in relation to the patient anatomy captured in the X-ray image.

Once the alignment of the instrument is within a first pre-determined angular range, the surgeon can continue to manipulate the instrument to reach the desired alignment. As the instrument is moved, the innermost circle 813 moves with the instrument and relative to the outer circle 812. The surgeon thus has a direct visual indication of where and how much to angle the instrument to reach the desired alignment. When the two concentric circles are within a second pre-defined range, such as 1 degree, the gap between the two concentric circles is filled in so that the circles become a donut 814 (FIG. 83B) centered on the tip of the instrument. The depiction of the donut can appear at different pre-defined angular ranges, such as increments of 1 degree, depending on the angular tolerance permitted for the instrument when it is finally introduced. Once the donut 814 appears the surgeon can advance the instrument into the bone knowing that the instrument is properly angularly aligned.

It is further contemplated that this same alignment procedure can be implemented to help the C-arm technologist align the x-ray beam with a drill hole in the patient's bone. In this instance, a tubular calibrator tool can be inserted into the drill hole and this calibrator tool thus becomes the instrument that is monitored by the tracking device and image processing device. In this instance, it is not the instrument—i.e., drill hole—that is moved, but rather it is the C-arm itself that is moved. The same concentric circles appear when the C-arm axis is within 5 degrees and 1 degree of the spatial orientation of the calibrator tool inserted into the drill hole. When the C-arm is properly aligned, the X-rays emanating from the device will pass perfectly through the center of the calibrator tool. Then, with the C-arm perfectly aligned with the drill hole, the calibrator tool can be removed and the implant, such as a bone screw, can be introduced into the X-ray field and manipulated as described above to achieve the proper orientation of the bone screw relative to the screw hole.

As discussed above, the present systems and methods utilize tracking information from a localizer system that acquires the position of the effecter. The tracking systems disclosed herein are configured to track six degrees of freedom of movement (X, Y, Z, Pitch, Yaw and Roll) of the fluoroscope as it is acquiring images of the surgical site. However, it is not always necessary to track all six degrees of freedom of movement of the surgical instruments used at the site. For instance, the roll movement of a Jamshidi needle or a bone screw is irrelevant to visualizing the surgical procedure. In certain instances, knowledge of only 3, 4 or 5 degrees of freedom (DOF) of the instrument is needed. When only 3 DOF are tracked, only the location of the tip of the instrument is known, so any change of angular orientation of the instrument is not available. When 5 DOF are tracked, pitch and yaw angular changes are known. With respect to tracking elements on an instrument, three or more markers are required to achieve tracking in 6 DOF. However, since some instruments do not require 6 DOF tracking, as discussed above, suitable tracking elements do not require three or more markers.

Figure 8A:
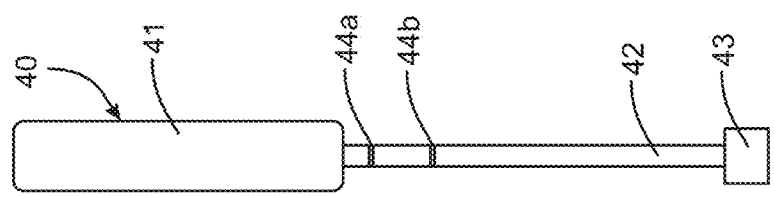
FIG. 8A is a side view of a generic effecter having marker bands used for tracking the position of the effecter.

Typical localizer systems utilize an array of optical sensors to track an optical tracking component mounted to the end of the effecter. In one aspect of the present disclosure, an effecter 40 includes a handle 41 with an elongated shaft 42 terminating in a working tip 43, as depicted in FIG. 8A. The shaft 42 is provided with optically trackable markers 44a, 44b in the form of optical bands that encircle the shaft so that the markers are visible at all rotational angles of the effecter. The bands may be formed by optical tape applied to the effecter or may be applied directly to the material of the effecter, such as by etching. The two markers 44a, 44b permit tracking the movement of the effecter in five degrees of freedom—X, Y, Z, pitch (X rotation) and yaw (Y rotation). The markers 44a, 44b are provided at a predetermined distance from the working tip 43 so that the localizer software can use the detected location of the two markers to extrapolate the 5 DOF position of the working tip.

In one aspect of this feature, the markers 44a, 44b are cylindrical and mounted on a cylindrical tool. The cylindrical nature of the markers means that they can be visualized by the optical tracking device at any roll orientation of the tool and at a full 360° viewing angle relative to the tool. The markers of the present embodiment thus provide on-axis tracking of the instrument regardless of the orientation of the tool or instrument on which the markers are mounted and regardless of the position of the optical tracking device. The longitudinal offset of the markers relative to each other provide a direct indication of the axis of the tool, which can then be tracked in five degrees of freedom.

In a further aspect of this feature, the markers 44a, 44b are separated by a predetermined spacing in which the spacing is indicative of the type of effecter. For instance, one spacing of the markers may denote a cage inserter while another different spacing of the markers may denote a distracter. The localizer system can be configured to discern the spacing of the markers 44a, 44b and then refer to a stored data base to determine the nature of the effecter being detected. The data base includes information locating the working tip in relation to the markers so that the position of the working tip can be accurately determined by sensing the location of the markers. The data base may also include a model of the instrument that can be used to generate the metal mask 20 described above. Once the particular effecter is identified, the localizer system will always know where the working tip is located even when one of the two markers is obscured.

Figure 8B:
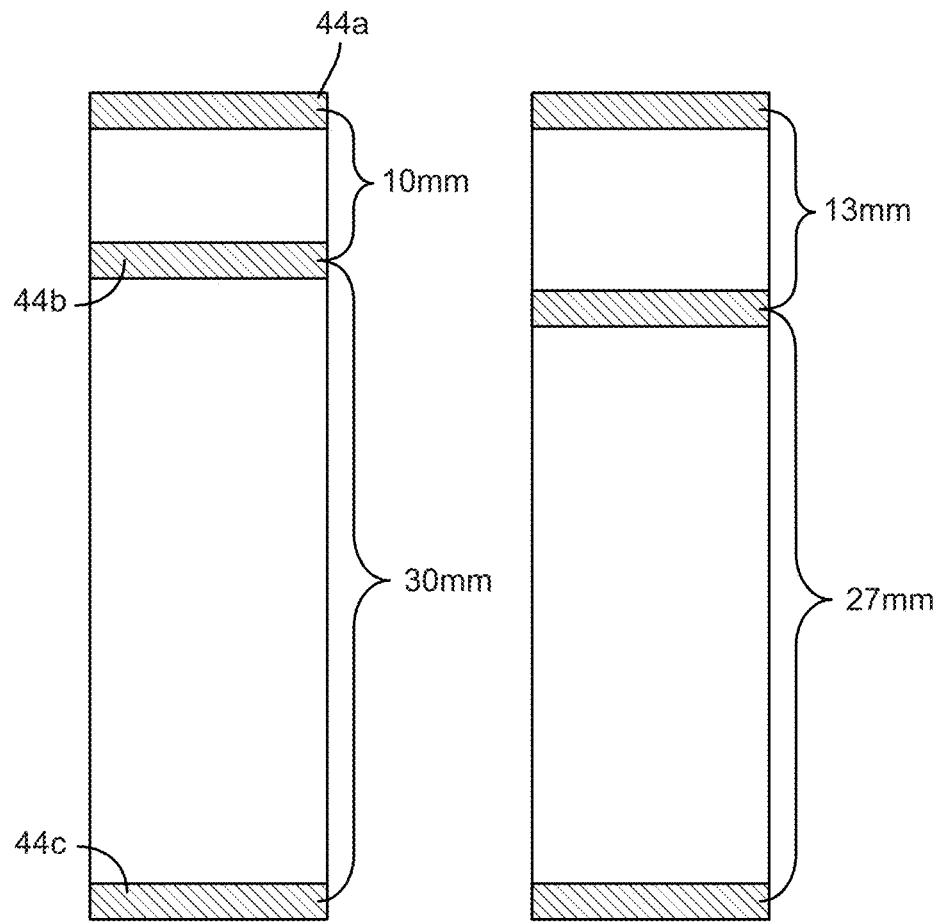
FIG. 8B is a representation of patterns of three marker bands for use on the effecter shown in FIG. 8A.

In an alternative embodiment, three marker bands can be positioned at pre-determined locations on the instrument. In this embodiment, three bands 44a, 44b, 44c are located at pre-determined spacings with the lowermost band 44c (or optionally the uppermost band) located at a predetermined distance from the working tip 43 of the instrument, as shown in FIG. 8B. In one specific example on the left side of FIG. 8B, the spacing between the top two bands is 10 mm while the spacing from the middle band to the lowermost band is 30 mm. The relative positions of the three bands can be used to identify the particular instrument and the location of the working tip, as can be done with two bands. The band arrangement depicted in the right side of FIG. 8B in which the middle band is 13 mm from the top band (rather than 10 mm as in the left side band arrangement) denotes a different instrument than the other band arrangement. In both cases, however, the three bands are positioned on the instrument so that the distance from the lowermost band 44c to the working tip (43 in FIG. 8A) is the same known value.

While the two band and three band arrangements can be easily used to identify the type of instrument, the three band embodiment always allows the image processing system to determine the location of the tip even when one band is covered or otherwise not visible to the optical detector. Thus, if the top band is covered, the imaging system can still recognize the separation between the middle and lower bands—30 mm in the left side arrangement and 27 mm in the right side arrangement—so the image system still knows what instrument is being imaged and where the working tip is located in space and ultimately in the X-ray image of the surgical site. Likewise, if the bottom band is covered the processor recognizes the 10 mm or 13 mm separation of the top and middle bands and still knows the instrument type and location of the working end. It can be noted that if the middle band is not detected by the optical tracking device the image processor cannot determine the type of instrument since the distance between the top and bottom bands is necessary the same for all instruments. However, the two bands can still be used to establish the location of the working tip and the five DOF position of the instrument.

Figure 9:
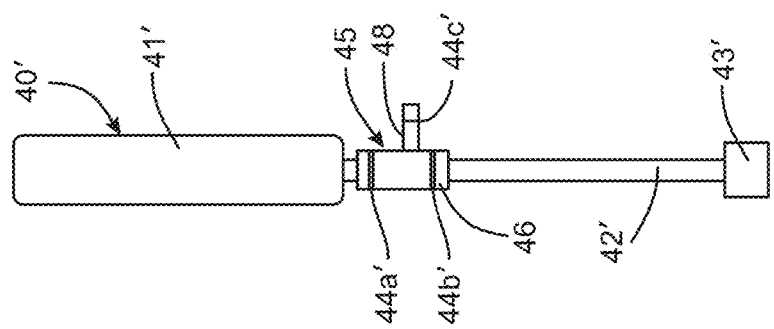
FIG. 9 is a side view of a generic effecter having a tracking element mounted on the effecter and providing marker bands for tracking the position of the effecter.

In another aspect, the markers are incorporated into a tracking element 45 that can be mounted to the shaft 42' of a tool 40' that is otherwise similar to the tool 40, as shown in FIG. 9. The tacking element includes a cylindrical or partially cylindrical body 46 that can be clipped onto the shaft 42' and held in position with a friction grip. The cylindrical body 46 includes the two markers 44a', 44b' in the form of bands that encircle the body. A third marker 44c' can be provided on an arm 48 that projects from the cylindrical body so that it is offset from the longitudinal axis of the shaft 42', with the third marker constituting an optically detectable band. The addition of the third marker 44c' adds a sixth degree of freedom to the position data detected by the localizer device, namely roll or rotation about the Z-axis or longitudinal axis of the shaft 42'. The bands 44a', 44b' can be spaced apart in the manner described above to denote a particular effecter.

Figure 36A:
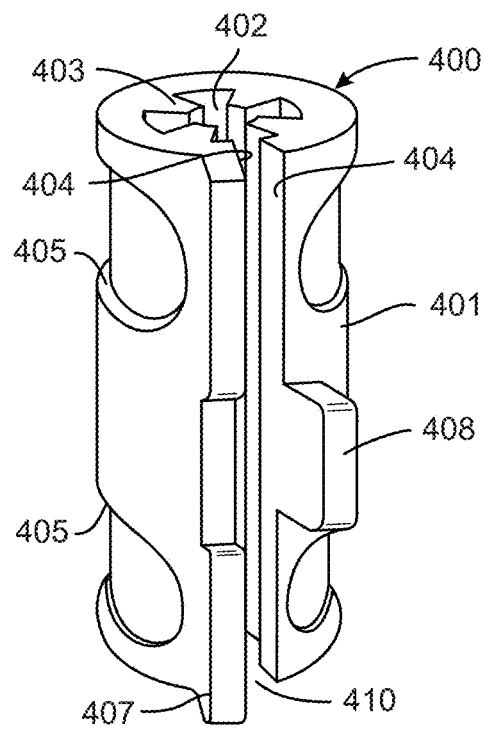
FIGS. 36A, 36B are perspective views of an in-line tracking snap according to one aspect of the present disclosure.
Figure 36B:
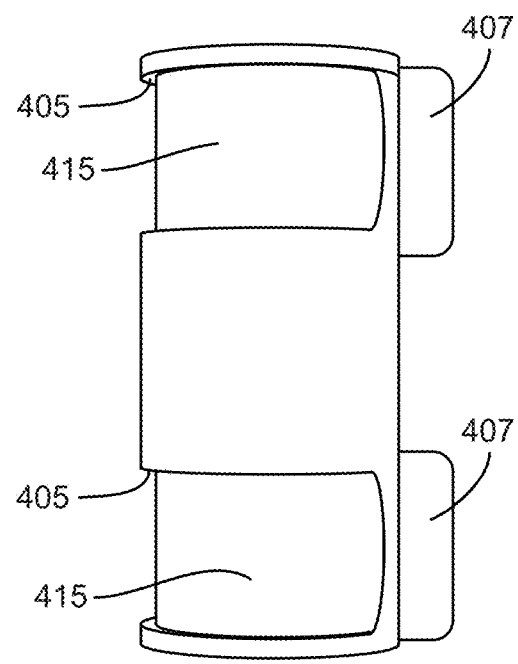
Figure 37A:
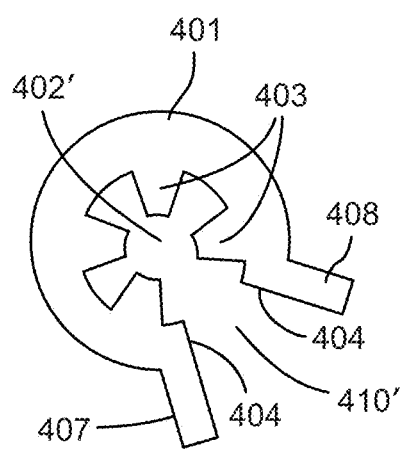
FIGS. 37A, 37B are end views of the in-line tracking snap shown in FIG. 36A, with the snap depicted in different opening configurations.
Figure 37B:
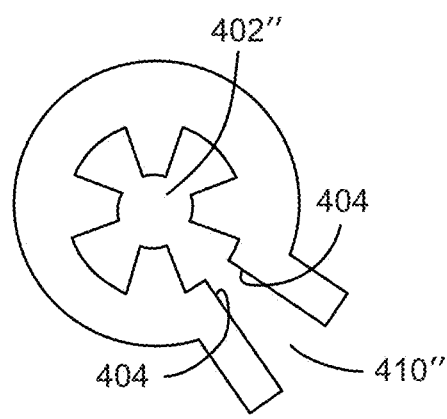
Figure 38:
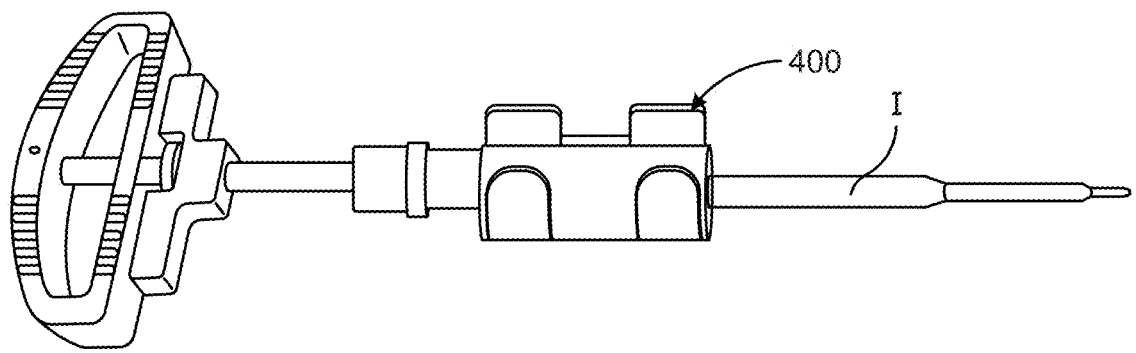
FIG. 38 is a side view of an instrument with the in-line tracking snap of FIG. 36A mounted thereon.

In-line or on-axis tracking elements according to alternative embodiments incorporate a resilient snap structure that clamps to the shaft of an instrument, tool or effecter by spring force. The in-line tracking snap 400 shown in FIGS. 36-37 includes a resilient cylindrical body 401 that defines a central bore 402 sized to fit around the cylindrical shaft of an instrument. The circumferential body includes inwardly projecting ribs 403 that are configured to provide a specific clamping force on the outer surface of the instrument when the snap 400 is closed on the instrument shaft. The cylindrical body 401 is thus formed of a strong resilient material that has an undeformed configuration shown in FIG. 36A in which the body defines a narrow gap 410 between the ends of the 404 of the body. In this undeformed configuration, the diameter of the bore 402 is slightly smaller than the diameter of the instrument shaft. The body defines tabs 407 at one end 404 and a tab 408 at the end 404 on the other side of the gap 410. The tabs 407, 408 are sized and arranged to be engaged by a person's fingers to pry the cylindrical body apart to increase the gap and therefore the diameter of the bore 402 as needed to be received on the shaft of an instrument. Thus, as shown in FIG. 37A, the gap 410' can be larger than the gap 410 so that the bore 402' has a larger diameter. Likewise, the gap 410" shown in FIG. 37B can be smaller than the gap 410' but larger than the undeformed gap 410 to accept an instrument having a thinner shaft. In each configuration, the natural resiliency of the circumferential body 402 generates a spring force sufficient to clamp the tracking snap 400 on the instrument. It can be appreciated that the inner surface of the circumferential body can include a coating or sheet providing greater friction in the contact with the instrument shaft to prevent slippage of the snap once it is engaged on the instrument, as shown in FIG. 38.

The body 402 is formed of a material that is not detectable by X-rays or by an optical tracking device, such as the device 130 shown in FIG. 1. The body of the tracking snap defines two circumferential indentations 405 that are sized to receive an insert 415 that is configured to be detected by the optical tracking device. Thus, in one embodiment, the insert 415 can be a reflective tape applied to the body at the indentation. Alternatively, the insert can be a body formed of a radio-transparent but optically detectable material that is press-fit or snap-fit into the indentations 405. It can be appreciated that the indentations, and thus the position of the detectable inserts 415, are at a specific distance apart, in the same manner as the fiducial markers 44a, 44b in the embodiment of FIG. 8A. It is further appreciated that the detectable inserts 415 extend substantially around the circumference of the tool, thereby providing the advantages of the cylindrical tracking elements discussed above.

Figures 39A, 39B:
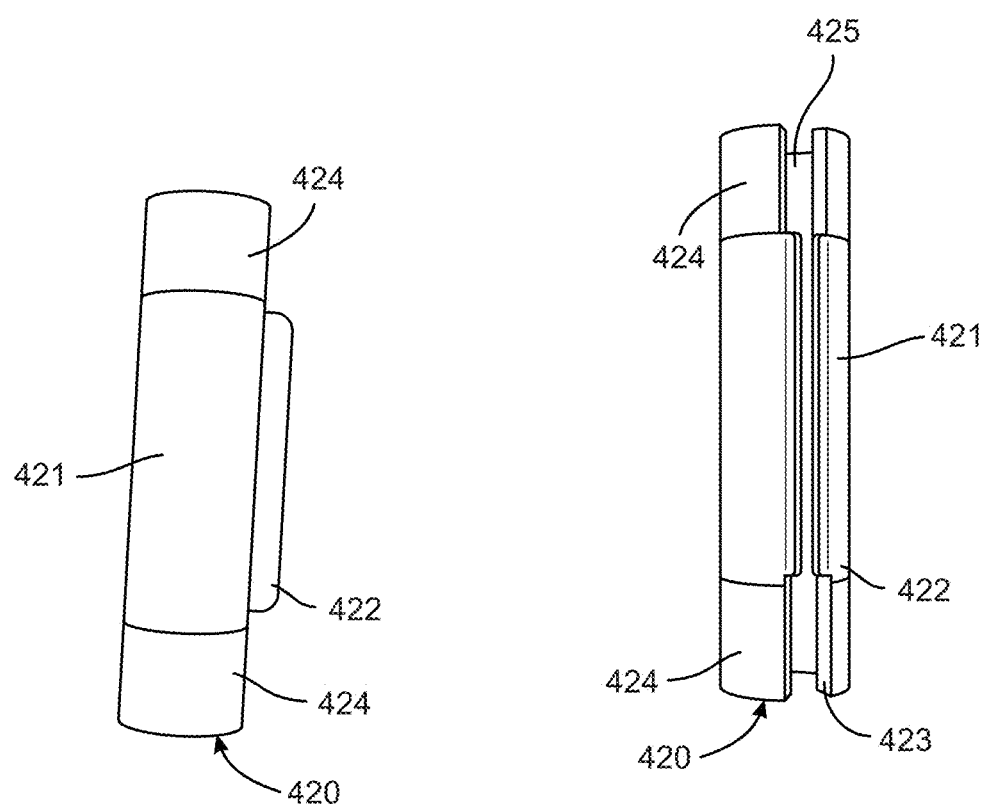
FIGS. 39A, 39B are side views of an in-line tracking snap according to a further embodiment of the present disclosure.

The in-line tracking snap 420 shown in FIGS. 39A, 39B is similar to the snap 400 in that the snap includes a resiliently deformable body 421 that defines a bore 425, with the ends of the body defining a gap 422 open to the bore. The body 421 defines opposing flanges 422 on either side of the gap that are configured to open when pressed against the shaft of an instrument. The flanges are thus outwardly curved to form a cam surface to push the ends of the body apart to widen the gap 423. Once the shaft of the instrument passes through the gap the resiliency of the body 421 springs back onto the outer surface of the instrument shaft. As with the snap 400, the inner surface of the snap 420 can include a friction coating or layer to enhance the grip of the snap onto the instrument. Like the snap 400, the snap 420 includes a detectable element 424 at opposite ends of the cylindrical body 421. Unlike the prior snap, the detectable element is applied directly to the cylindrical body, rather than engaged within an indentation. Thus, in one embodiment the detectable element 424 can be an optically reflective sticker. As with the prior embodiments of the in-line tracking feature, the detectable elements 424 are provide at a specific spacing to act as an identifier of the type of instrument, and to be used in identifying the location of the working end of the instrument. The detectable elements 424 also substantially encircle the instrument, providing the benefits of the cylindrical markers described above.

Figure 40A:
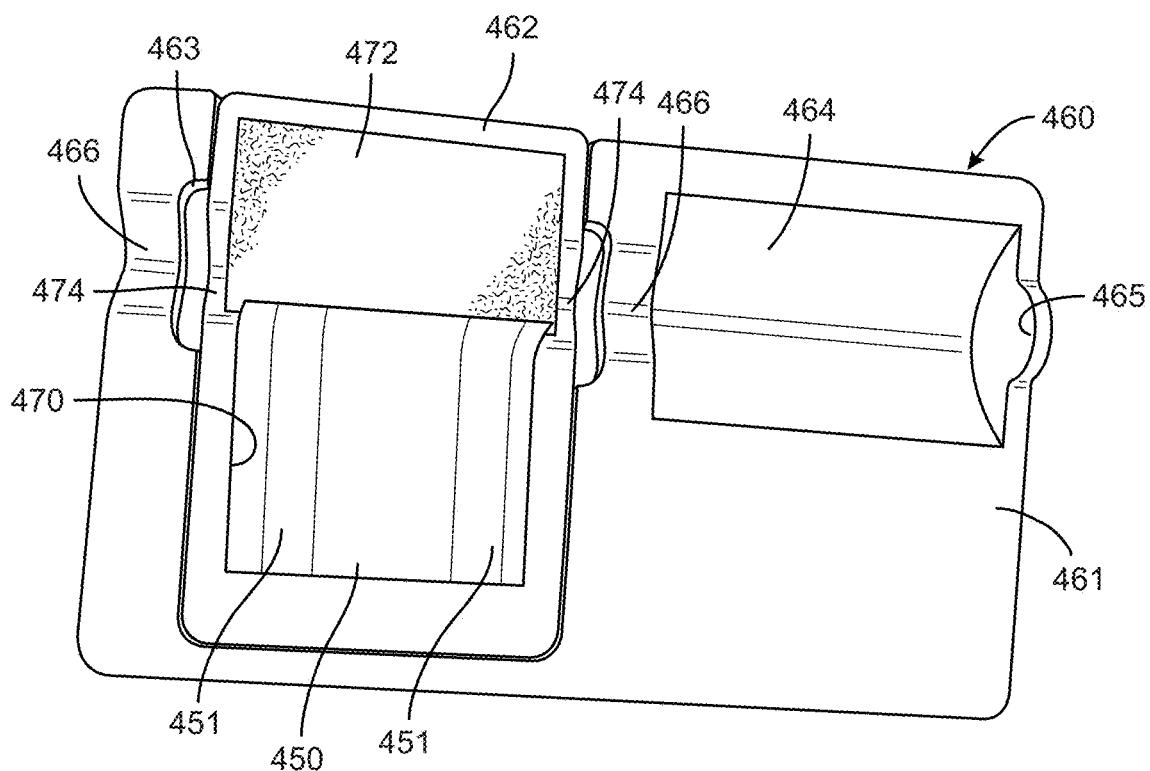
FIGS. 40A-40D are views of an applicator for applying a tracking sticker to an instrument according to another aspect of the present disclosure.
Figure 40B:
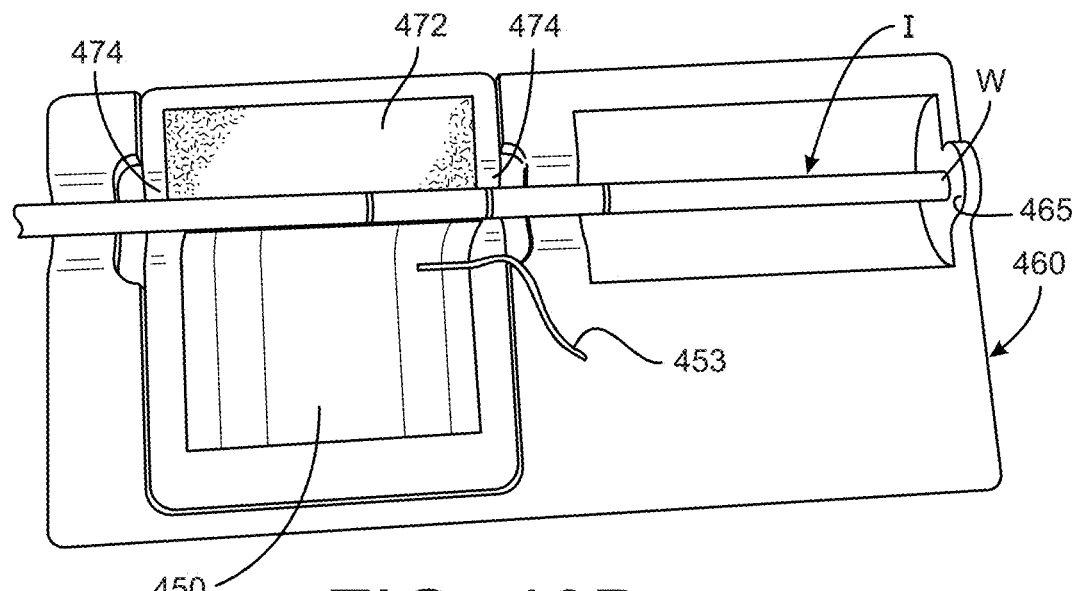
Figure 40C:
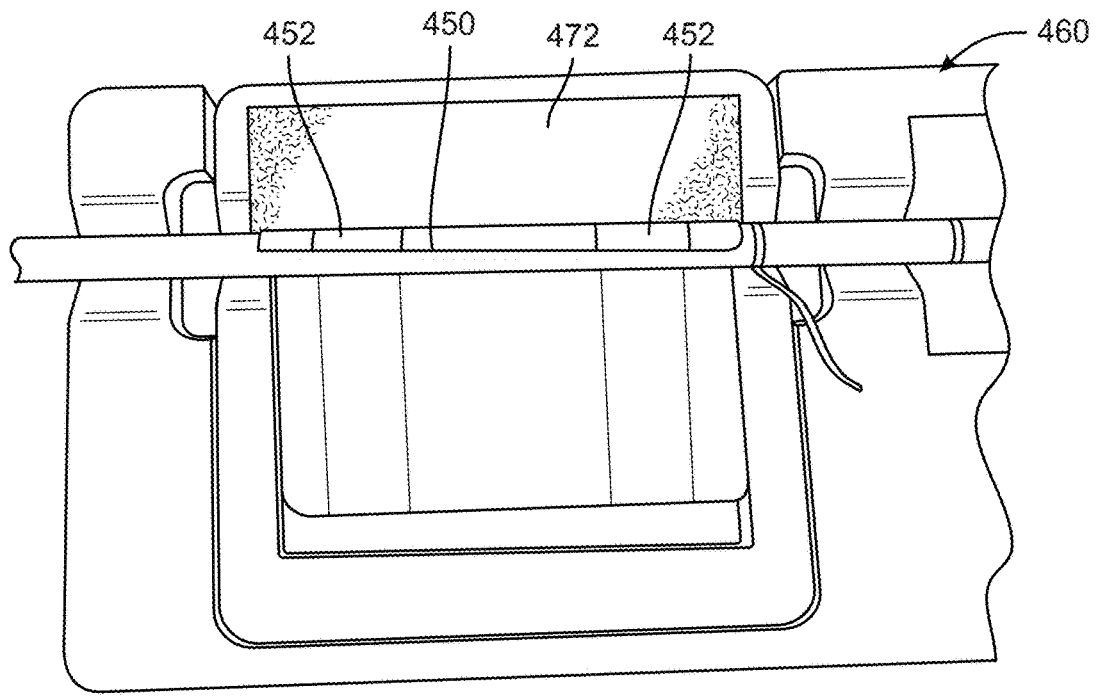
Figure 40D:
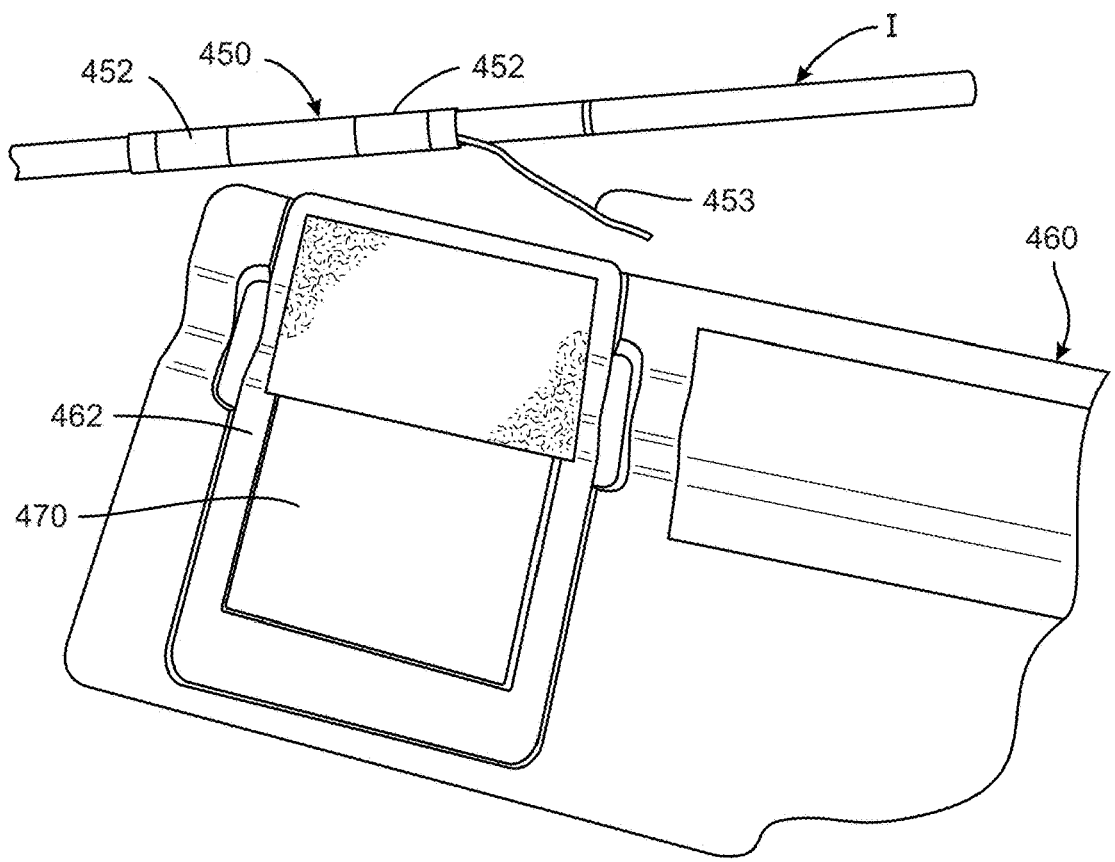

In another embodiment of the in-line tracking element, the element is a tape or sticker 450 with detectable bands 451, as shown in FIG. 40D. The sticker is applied continuously around the circumference of the shaft of an instrument, such as the instrument I in FIGS. 40B-40D. It is understood that the sticker is formed of a material that is transparent to X-rays and to the optical detector 130, while the detectable bands 451 are transparent to X-rays but detectable by the optical detector (or similar detector that does not interfere with X-rays). The stickers and detectable bands 451 are configured so that the bands are orthogonal to the longitudinal axis of the instrument so that an accurate location of the working tip can be established. The bands also encircle the instrument, providing for full 360° detectability.

In order to properly apply the sticker 450 to an instrument, the present disclosure provides an applicator assembly 460 as shown in FIGS. 40A-40D. The applicator 460 includes a tray 461 that can be molded from a suitable non-reactive material, such as a plastic. The tray defines a first recess 463 that supports a removable insert 462, and a second recess 464. The second recess terminates in a calibration wall 465 that is configured to establish the position of the working end W of the instrument I (FIG. 40B) when the instrument is positioned within the applicator. The tray 461 further defines notches 466 that are aligned with the calibration wall 465 to properly align the instrument I within the applicator. The notches 466 can be V-shaped to accurately align the instrument regardless of the diameter of the instrument.

The insert 462 also defines a second pair of notches 474 that are aligned with the notches 466 of the tray when the insert is received within the first recess 463. The second notches can also be V-shaped to accommodate varying instrument diameters. It is contemplated that the notches 466 and 474 are aligned both horizontally and vertically when the insert 462 is properly positioned within the tray. The insert 462 defines an insert recess 470 that receives the sticker 450 and a resilient body 472. The resilient body 472, which can be a sponge, is sized to overlap the second notches 474, as shown in FIG. 40D. The sticker 450 is positioned within the insert 462 overlapping the top surface of the resilient body 472, as shown in FIGS. 40A, 40B. The sticker 450 includes a pressure adhesive surface that is on the opposite surface of the sticker from the detection bands 452. Thus, the sticker 450 is placed within the insert with the adhesive surface facing upward. The insert recess 470 and sticker 450 are sized and configured so that the sticker seats uniformly or snugly within recess to ensure that the marker bands 452 are properly oriented on the instrument when the sticker is applied. In one aspect, the sticker 450 can be provided with a cord or string extending across the width of the sticker and exposed at one side of the sticker, as shown in FIGS. 40B, 40D. When the sticker is adhered to the instrument, the string can be pulled to tear the sticker along its width, facilitating removal of the sticker by peeling along the torn edge.

In use, the sticker 450 is positioned squarely within the insert recess 470 with one end of the sticker overlapping the resilient body 472 and with the adhesive surface facing upward. the instrument I is placed within the tray 461 with the working end W bearing against the calibration wall 465 and then the shaft of the instrument is pivoted downward onto the sticker and onto the second notches 474. The resilient body 472 is configured to provide resistance or an upward force against the sticker as the instrument is pressed down onto the sticker during application of the sticker onto the instrument. The instrument I is then rolled within the notches 474 while maintaining pressure on the resilient body, as shown in FIG. 40C, so that the sticker is uniformly adhesively applied to the instrument, as shown in FIG. 40D.

The applicator 460 includes two components—the tray 461 and the insert 462—that determine the location of the marker bands 452 on an instrument. The tray is configured so that the calibration wall 465 is at a predetermined distance from where the sticker will be applied. It is thus contemplated that different trays can be provided for different types and sizes of instruments. The insert 462 is also configured to properly align the sticker with the calibration wall for the desired location of the marker bands. Different inserts can have different dimensions of the recess 464 to accommodate different types of stickers. An array of stickers can be provided with different spacings between the marker bands 452, and even different numbers of bands. The applicators 460 and stickers 450 of the present disclosure thus provide a universal system for providing optical (or similar) marker bands on a wide array of instruments.

Figure 47:
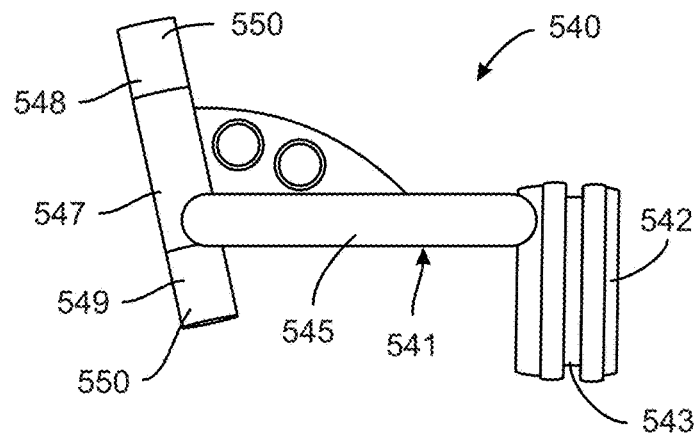
FIG. 47 is a top view of an alternative configuration of a tracking element incorporating cylindrical markers according to another aspect of the present disclosure.
Figure 51:
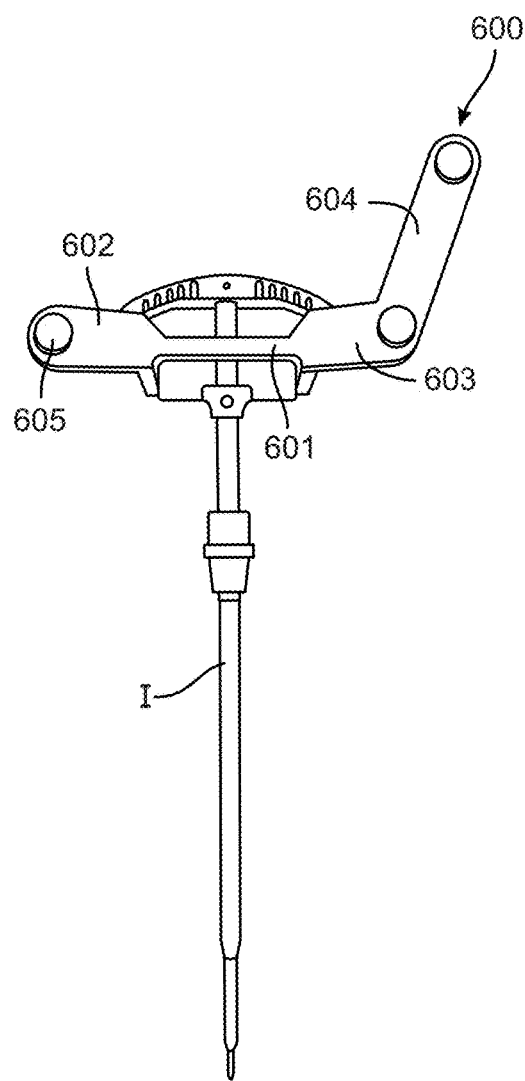
FIG. 51 is a side view of a tracking element according to a further embodiment mounted on an instrument.
Figure 58A:
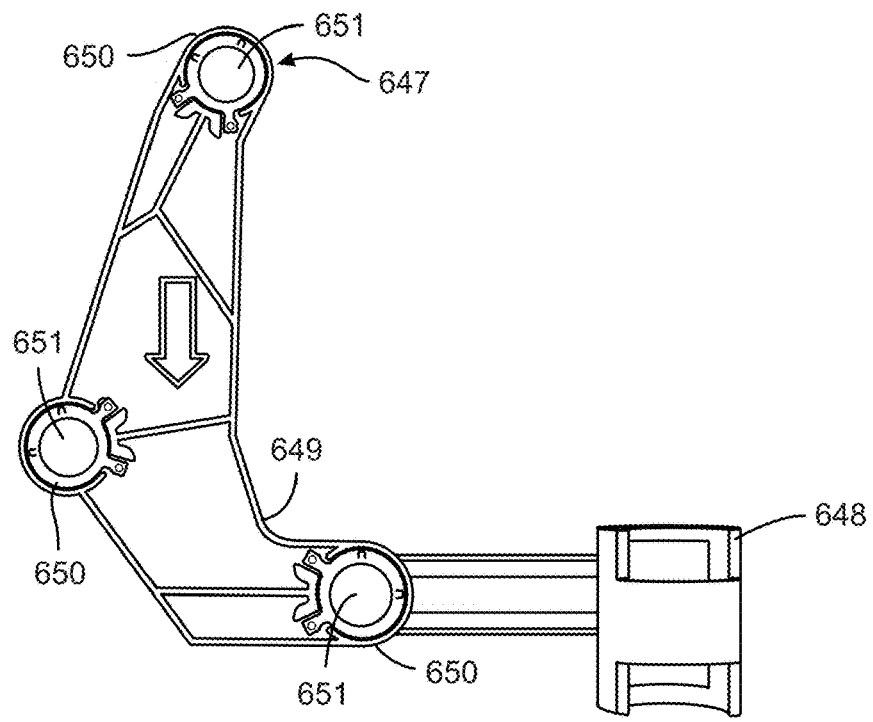
FIG. 58A is a top view of another tracking element using disc-type tracking components.

The tracking elements just described include components that can be optically tracked by the tracking device 130, as described above. Thus, in these embodiments the optically detectable components provide a continuous, uniform surface that can be detected by the tracking device, whether IR or visible spectrum. In alternative embodiments, one of more of the detectable components can carry encoded information, such as a bar code or a QR code. For example, the detectable sticker 450 shown in FIG. 40D can incorporate a bar code or QR code for the first band 451. The coded band can carry information indicative of the particular instrument, which information can be detected and used by the image processing device 122, such as to assist in locating the working tip and/or positional orientation of the instrument carrying the coded band. The bar code or QR code feature may be read by a high-definition camera independent of the tracking device 130, while still performing its tracking function. It can be appreciated that the bar code or QR code feature can be incorporated into the other cylindrical markers described herein, such as the markers 400 (FIG. 36A), 420 (FIG. 39A), 550 (FIG. 47), 624 (FIG. 53A), 632 (FIG. 54D), and can even be incorporated into the disc-shaped markers 510 (FIG. 42), 605 (FIG. 51), 651 (FIG. 58A), for example.

Figure 10:
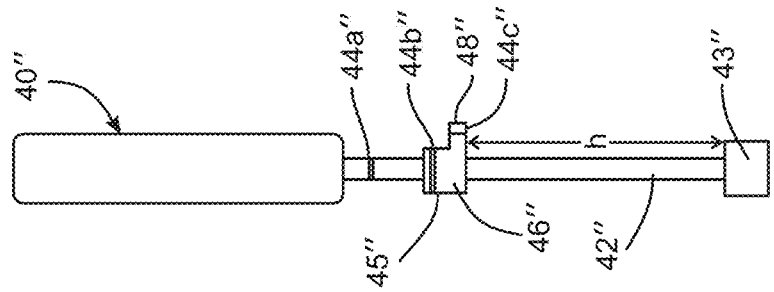
FIG. 10 is a side view of a generic effecter having another tracking element mounted on the effecter and providing marker bands for tracking the position of the effecter.

In an alternative embodiment, an effecter 40" shown in FIG. 10 includes an existing conventional fiducial marker 44$a$" on the shaft 42" of the effecter. A tracking element 45" includes a cylindrical or partially cylindrical body 46" configured to be clamped onto the shaft 42" of the effecter. The body 46" includes a second marker 44$b$" in the form of a band that encircles the cylindrical body, and may include a third marker 44$c$" on a perpendicular extension 48". The two markers 44$b$", 44$c$" on the tracking element 45" cooperate with the existing fiducial 44$a$" on the effecter to permit detecting the position of the effecter, and therefore the working tip 43", in six degrees of freedom. In this embodiment, the tracking element 45" is clamped to the shaft 42" at a particular height h relative to the working tip 43". The height h produces a predetermined spacing relative existing fiducial 44$a$", which spacing can be used to identify the nature of the particular effecter. A calibration tool may be used to position the tracking element 45" at the proper height for a particular effecter as described herein.

Figure 41:
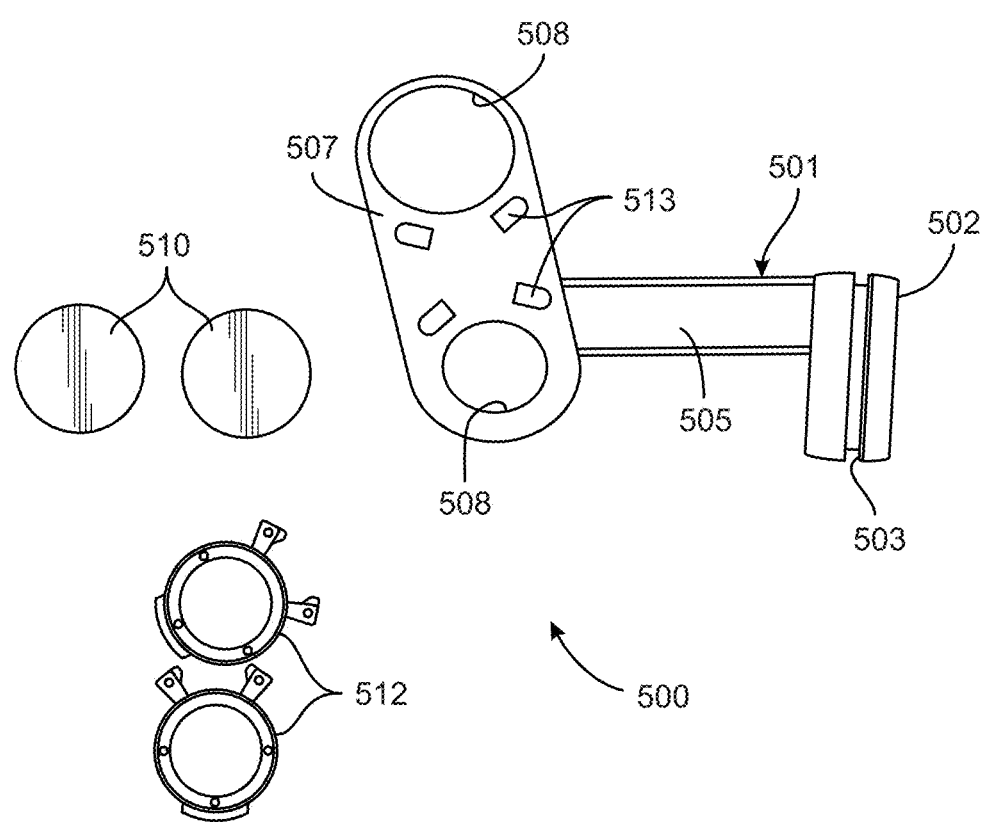
FIG. 41 is a perspective view of components of a tracking element according to a further aspect of the present disclosure.

FIGS. 41-44 show another embodiment of a tracking element in the form of a two-marker tracking element 500. Unlike the prior markers, the element 500 is not a cylindrical element, but instead projects laterally outward from the instrument on which it is mounted. The tracking element 500 includes a body 501 that is formed of a material that is transparent to x-rays and to optical detectors used in surgical settings. In one embodiment, the body is formed of a plastic in a conventional plastic molding process. The body 501 includes a mounting portion 501 that defines a channel 502 to be engaged around the shaft of an effecter, such as a surgical tool or instrument. An arm 505 extends from the mounting portion 501 and terminates in a marker support portion 507. The marker support portion 507 is an elongated plate that defines two marker openings 508 offset from each other by a predetermined distance (distance S in FIG. 48). The openings 508 are sized to receive a marker 510 therein, as shown in FIG. 41. The markers 510 positioned within each opening 508 are formed of a material that is radio-transparent to x-rays but detectable by the optical detectors used in surgical settings. Thus, the markers can be sensible by an electromagnetic or an infrared optical tracking system, such as system 130 (FIG. 1). In one embodiment, the markers 510 are in the form of discs that are sized to fit snugly within the openings 508. To that end the openings can be provided with a circumferential ledge against which the optical marker disc is seated. A marker clip 512 holds the marker in the opening by encircling the perimeter of the disc. The marker clip 512 engages a corresponding catch 513 formed on the support portion 507 to firmly hold the marker in the opening. In certain embodiments, two markers 510 can be disposed in each opening to permit symmetrical tracking of the instrument from both sides of the tracking element 500.

It is contemplated that other means can be provided for fixing the markers 510 to the tracking element 500. For instance, the clips 512 can have other configurations or can be a single clip that mates with the marker support portion 507 to simultaneously fix both markers. As a further alternative, the opening 508 and markers 510 can be configured for press-fit or snap-fit engagement, provided that the engagement is sufficiently strong to ensure that the markers cannot be dislodged during use in a surgical environment.

Figure 42:
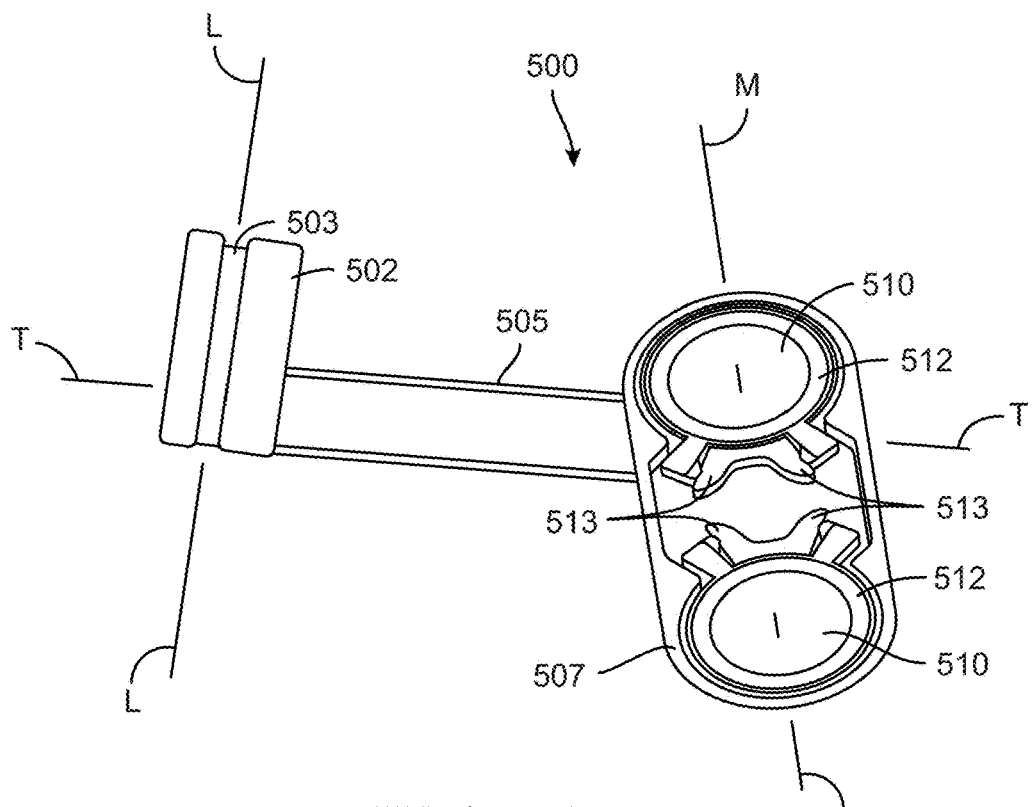
FIG. 42 is a top view of a component of the tracking element shown in FIG. 41.
Figure 43:
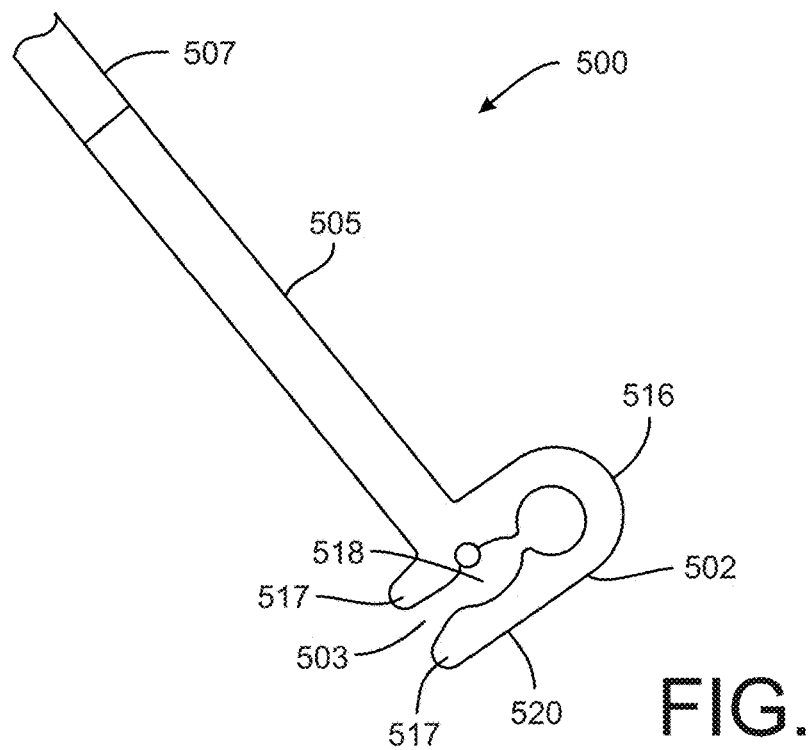
FIG. 43 is a side view of the component shown in FIG. 42 with an additional component to increase friction between the tracking element and an instrument on which the element is mounted.
Figure 44:
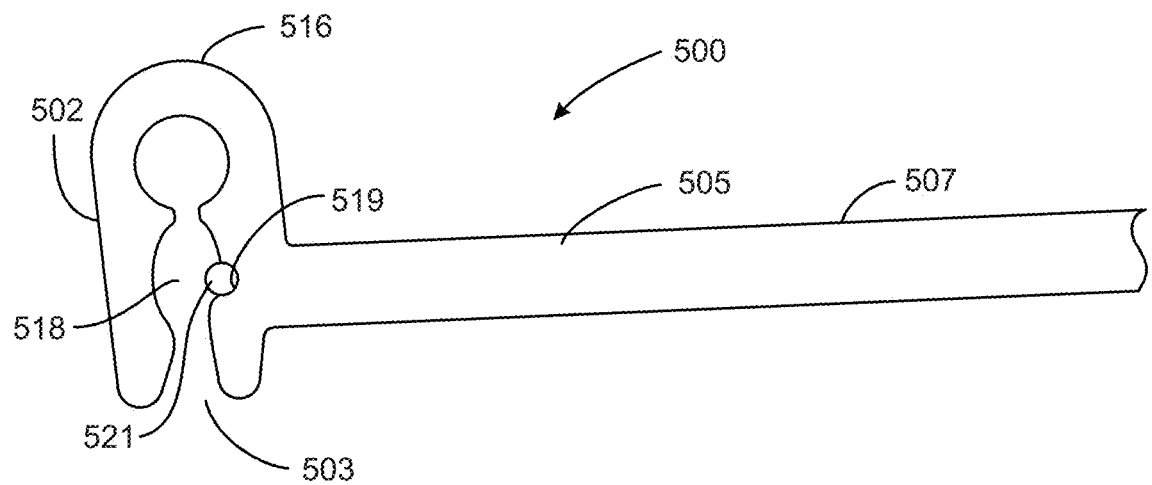
FIG. 44 is a side view of the component shown in FIG. 42 with a different component to increase friction.
Figure 48:
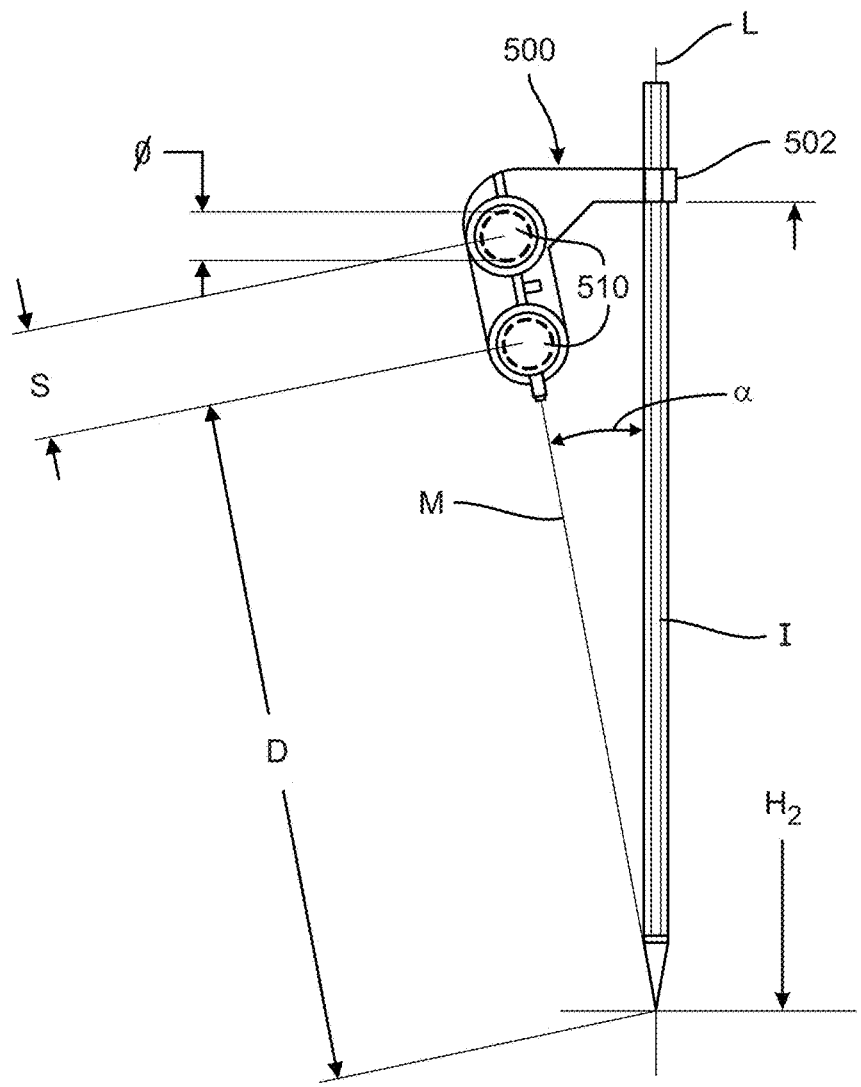
FIG. 48 is a view of the tracking element of FIG. 42 mounted on an instrument.

As shown in FIG. 42, the channel 503 in the mounting portion 501 extends along a longitudinal axis L that coincides with the longitudinal axis of the instrument when the tracking element 500 is mounted thereon. The arm 505 is elongated along a transverse axis T that can be generally perpendicular to the longitudinal axis T. The centers or origins of the openings 508 in the marker support portion 507 are aligned along an axis M that is not perpendicular to the transverse axis T and not parallel to the longitudinal axis L. As shown in FIG. 48, the axis M forms an angle $\alpha$ relative to the longitudinal axis L. This angle $\alpha$ is used to calibrate the location of the tracking element 500, as described in more detail herein with reference to FIGS. 48-50.

Figures 45, 46:
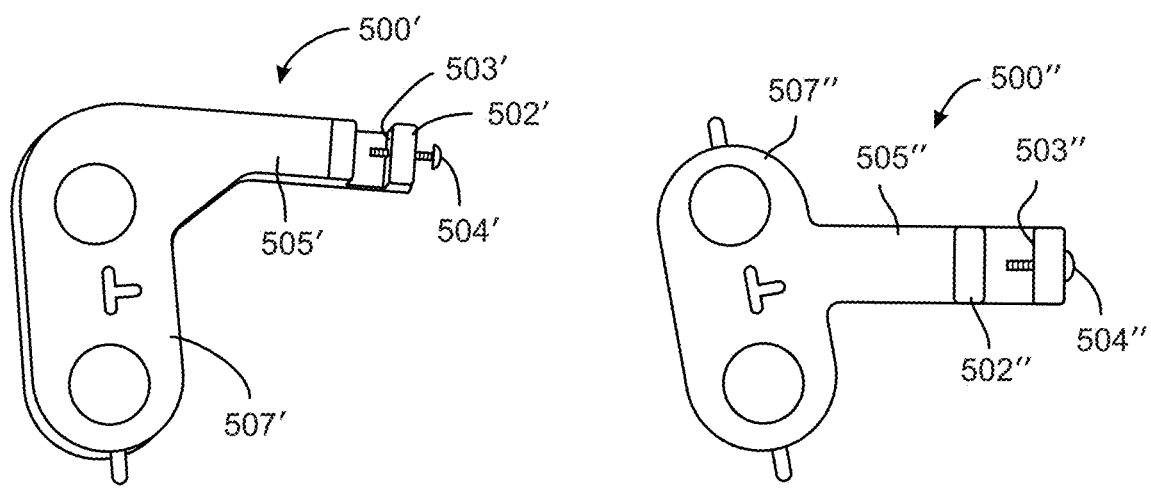
FIG. 45 is a top view of a component of a tracking element with an alternative feature for mounting the element on an instrument.
FIG. 46 is a top view of an alternative configuration of a tracking element according to a further aspect of the disclosure.
Figure 49:
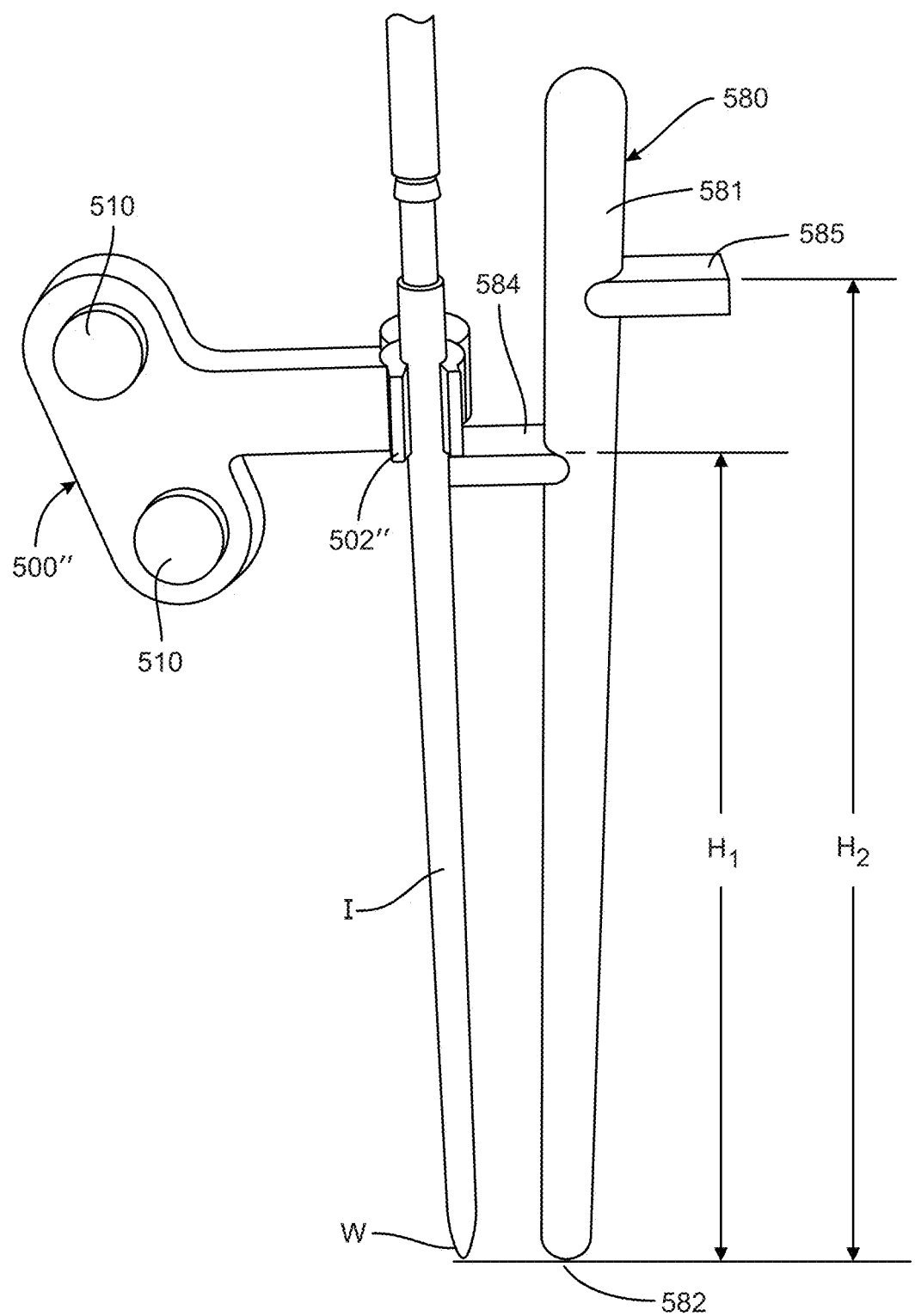
FIG. 49 is a perspective view of a calibration tool used to calibrate the position of the tracking element mounted on the instrument as shown in FIG. 48.
Figure 50:
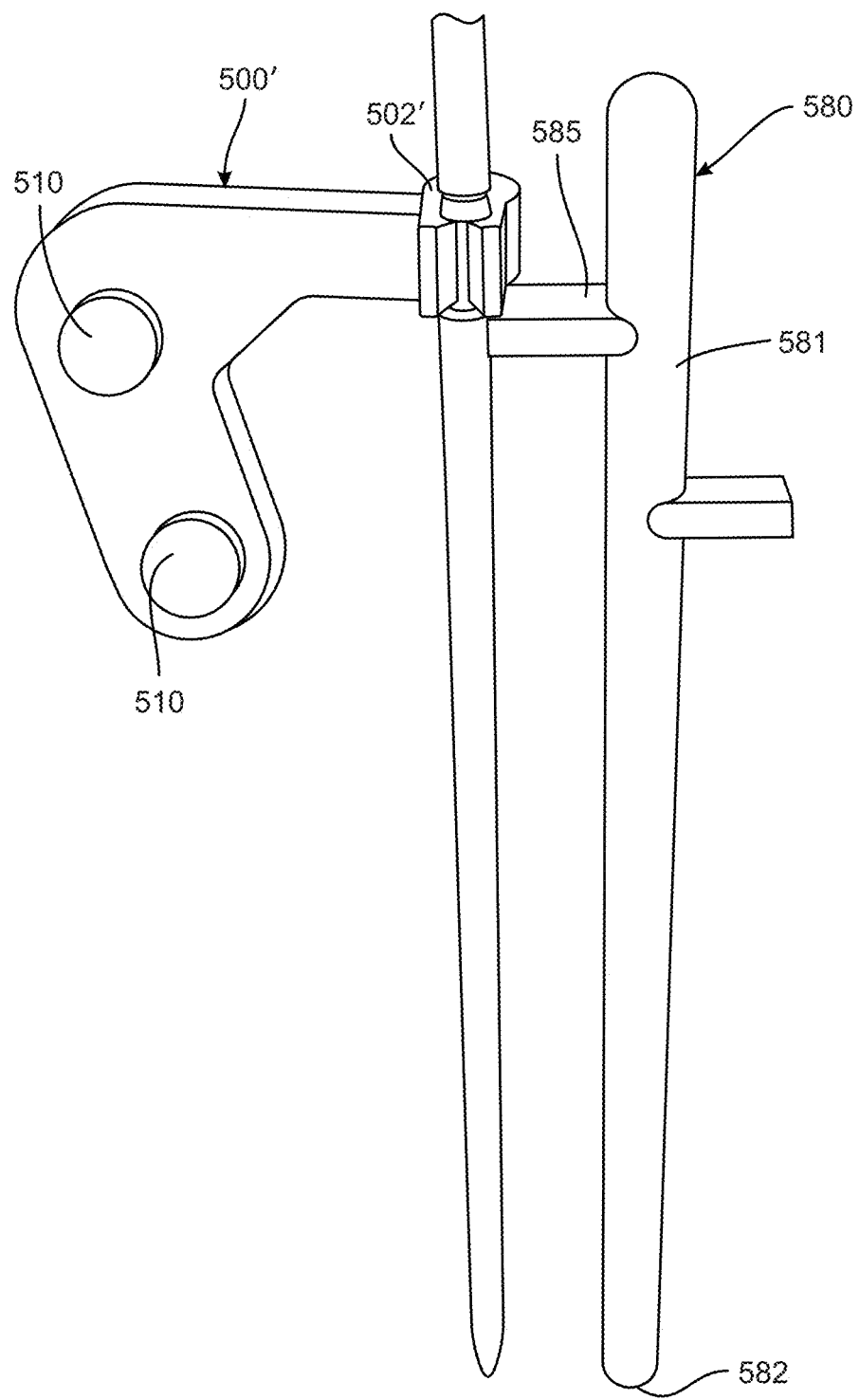
FIG. 50 is a perspective view of the calibration tool shown in FIG. 49 positioned for an alternative calibration of the tracking element.

In one aspect of the tracking element 500, the mounting portion 502 includes two legs 517 that define the channel 503. The legs 517 are resiliently deflectable to allow the legs to be pushed apart during insertion of an instrument into the channel 503. In one embodiment, the mounting portion can define a hinge 516 between the legs 517 that allow the legs to be deflected apart. The legs define a generally circular cavity 518 that is sized to receive the cylindrical shaft of an instrument, such as illustrated in FIGS. 48-50. The legs 517 and/or hinge 516 can be configured so that the cavity 518 must be expanded in order to receive the shaft of the instrument, thereby introducing friction between the tracking element 500 and the instrument to hold the element in position. Alternatively, the cavity may be lined with a friction surface or friction pad 520 formed of a high friction material, such as neoprene. The friction pad thus increases the friction between the element 500 and the instrument to firmly hold the element in place during use of the instrument. In another alternative, a notch 519 can be defined in one or both legs 517 at the cavity 518, the notch configured to receive a friction peg 521 that is formed of a high-friction material to improve the hold between the tracking element 500 and the shaft of the instrument. It is contemplated that the tracking element 500 is configured to ensure firm gripping of the tracking element on the instrument so that the element cannot move while the instrument is manipulated in a surgical procedure. In some instances, the instrument can be subjected to an axial force, such as when the instrument is a guide pin being driven into a bone by a mallet. The tracking element must be capable of gripping the instrument to that it is not dislodged under these conditions. Thus, in a further alternative, the mounting portion can be modified as shown in FIGS. 45-46. In those embodiments, the mounting portions 502', 502" include a channel 503', 503" to receive the shaft of the instrument in the same manner as the tracking element 500 described above. However, in this embodiment, a set screw 504', 504" is provided that can be tightened against the surface of the instrument to clamp the tracking element in position.

The tracking element 500 shown in FIGS. 41-42 is configured in a modified "L" configuration, with one marker location slightly offset to one side of the axis T and the other marker location offset to the opposite side of the axis. Other arrangements of the marker locations are contemplated, such as the arrangements shown in FIGS. 45-46. The tracking element 500' shown in FIG. 45 is in the general shape of the numeral "7" in which the marker support 507' is arranged relative to the arm 505' so that both marker locations are offset to one side of the arm. The tracking element 500"

shown in FIG. 46 is in the general shape of a "T" with the two marker locations offset to either side of the arm 505". In each embodiment, the marker supports align the marker locations along the known marker axis M (FIGS. 42, 48) so that the markers supported by the tracking element are in a well-defined known orientation relative to the instrument on which the element is mounted.

In the embodiments shown in FIGS. 41-46, the markers 510 are discs that are formed of an optically detectable but radio-transparent material. The tracking element 540 shown in FIG. 47 incorporates cylindrical markers that are formed of a radio-transparent but optically detectable material. The element 540 includes a body 541 that forms the mounting portion 542 with a channel 543 for receiving the shaft of an instrument, tool or effecter. An arm 545 extends from the mounting portion to support a marker mount 547. The marker mount includes two posts 548, 549 that extend along the marker axis M, as in the previous embodiments. The posts are generally cylindrical and each carry a cylindrical marker 550 at the same position and orientation as the markers 510. The cylindrical markers 550 mounted on the posts 548, 549 have the advantage of being offset from the longitudinal axis of the tool/instrument so that they are optically detectable from any orientation of the tracking element. On the other hand, the markers 510 of the tracking element 500 can theoretically be oriented so that the plane of the disc-shaped markers is perfectly aligned with the optical sensor, rendering the markers undetectable, at least for a moment.

The tracking elements 500, 500', 500", 540 described above are configured to be engaged on an instrument, tool or effecter so that the movement of that component can be tracked by the optical tracking device, such as the device 130 shown in FIG. 1. The tracking device tracks the position of the tracking elements and based on the geometry of the tracking element and the instrument the image processing device 122 (FIG. 1) can determine the location of the working end of the instrument as well as the actual position of the instrument relative to the X-ray C-arm 103. In order to effectively track the instrument in multiple degrees of freedom it is critical that the tracking element be at a pre-determined fixed relationship to the working end of the instrument so that the image processing device 122 can reliably use the marker locations to establish the instrument position in up to six DOF. In one embodiment, the instrument itself is provided with a fixed mounting location that is engaged by the tracking element. Thus, in one approach the shaft of the instrument can be configured with an indented circumferential groove sized to the length of the mounting portion 502 of the element 500 so that the mounting portion can be seated within the groove. Location in the roll degree of freedom (i.e., rotation about the longitudinal axis of the instrument) can also be fixed, such as by a ball and detent construction.

In another embodiment, a calibration tool 580 shown in FIGS. 49-50 is used to locate the tracking element on the shaft of the tool, instrument or effecter. The calibration tool includes an elongated body 581 with a tip 582 configured to seat on a flat calibration surface. A first platform surface 584 is defined at a height H1 from the tip 582 and a second platform surface 585 is defined at a greater second height 112. The platform surfaces 584, 585 can be in the form of a plate projecting perpendicularly from the body 581, or can be integrated into the body itself by increasing the diameter of the body at the two height locations.

As shown in FIG. 49, the tool 580 and an instrument I are positioned next to each other with their respective tips on the flat calibration surface. In FIG. 49, the lower platform surface 584 at height H1 is in contact with the shaft of the instrument I to serve as a guide for mounting the "T"-shaped tracking element 500". In particular, the element 500" is snapped onto the instrument so that the bottom of the mounting portion 502" rests on the platform surface 584. As shown in FIG. 50, the mounting portion 502' of the "7"-shaped tracking element 500' rests on the second platform surface 585 at the greater height 112.

In each case, the calibration instrument is positioning the tracking element so that the axis M of the markers intersects the working end W of the instrument, as shown in FIG. 48, forming the angle α relative to the longitudinal axis L passing through the instrument I. The tracking devices are mounted at a pre-determined location so that the distance D from the lowermost marker and the instrument tip is also known. It can be noted that the tracking elements 500', 400" have the lowermost marker at different locations below the corresponding arm 505', 505". The two different heights 111, 112 of the calibration tool 580 accounts for the differences in geometry of the elements to ensure that the distance D is known regardless of which tracking element is used. The tracking routines implemented by the image processing device 122 is provided with the pre-determined distance D and angle α, from which the actual 3, 4, 5 DOF location of the working end W of the instrument, tool or effecter can be calculated, as well as the position of the instrument in space. This information can thus be used to locate the instrument relative to an X-ray of the surgical site, which is useful in providing the metal mask images of FIGS. 5-6, but especially the image of the slug 35 indicative of the working tip W of the instrument in the X-ray image in FIG. 7, as discussed above.

Figure 52:
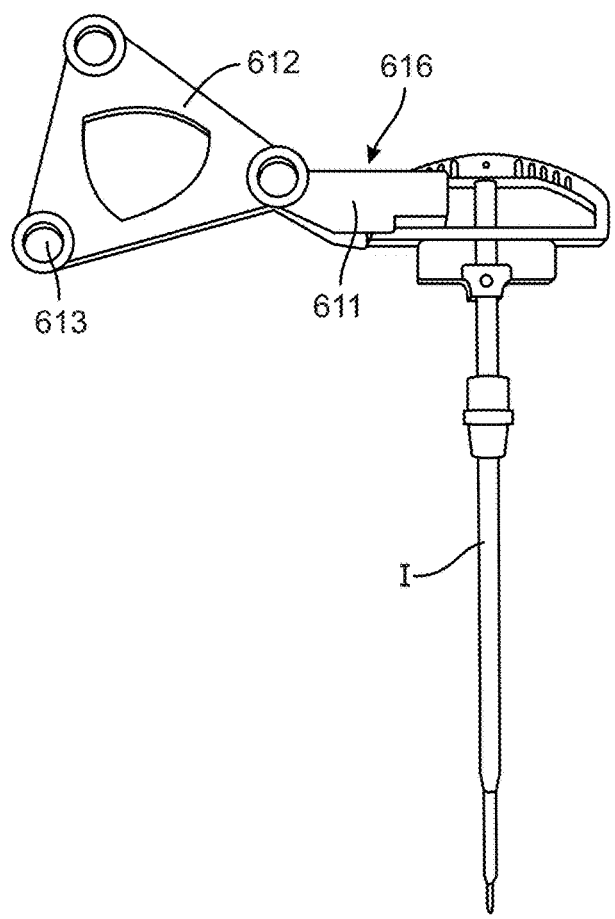
FIG. 52 is a side view of a tracking element according to another embodiment mounted on an instrument.

FIGS. 51-56 show other tracking elements that incorporate three markers. The element 600 shown in FIG. 51 includes a base 601 adapted to be mounted to the head of the instrument I. Arms 602, 603 extend from the base and arm 604 projects at a non-perpendicular, non-colinear angle from arm 603 so that the tracking device can define the orientation of the instrument in 6 DOFs. A marker 605 is mounted at the end of each arm. In this embodiment, the markers are discs that are pressed into openings defined in the arms. The tracking element 610 shown in FIG. 52 illustrates the openings 613 for receiving the discs 605 shown in FIG. 51. The tracking element 610 is also configured for 6DOF tracking of the instrument, with a triangular body 612 defining the disc openings 613 at the vertices of the body. The triangular body 612 extends from a mounting base 611 that is configured to be engaged to another part of the instrument I. In each case, the mounting base 601, 611 can be in the form of a snap that snaps onto structure of the instrument. For the tracking element 600, the base 601 snaps onto the head of the instrument, whereas for the tracking element 610, the base 611 snaps onto the handle of the instrument, which handle is in turn locked onto the head of the instrument. With both tracking elements 600, 610, the marker discs 605 are positioned in space to enable 6 DOF tracking of the instrument and may also be arranged in a unique pattern to be used to identify the type of instrument on which the tracking element is engaged.

Figure 53A:
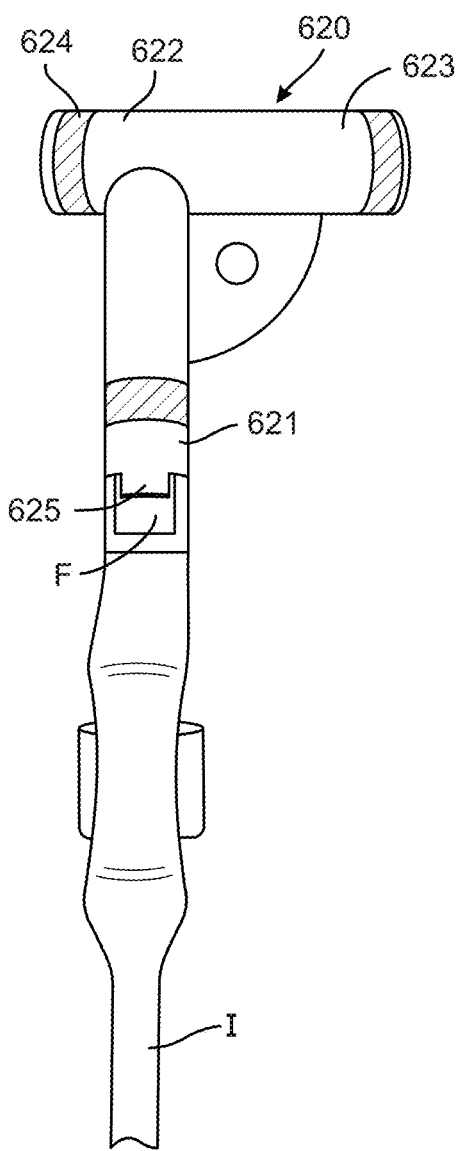
FIGS. 53A, 53B are side views of another tracking element in alternate positions on the end of an instrument.
Figure 53B:
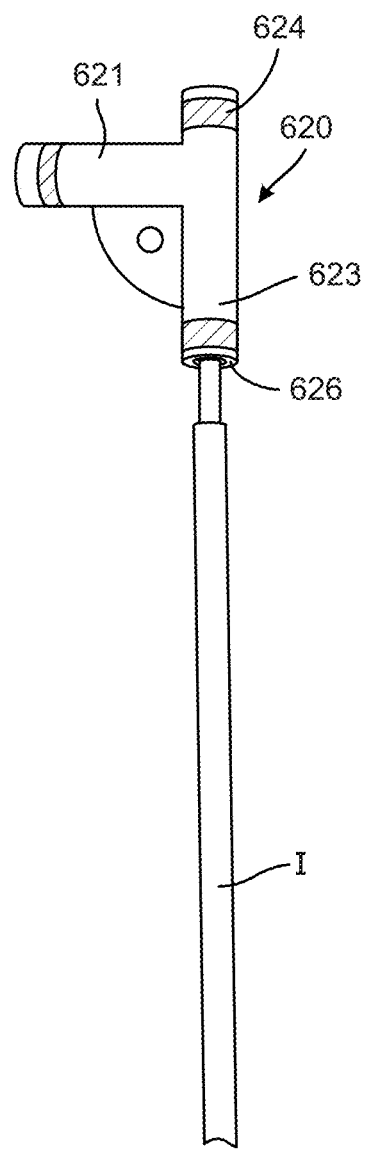
Figure 55:
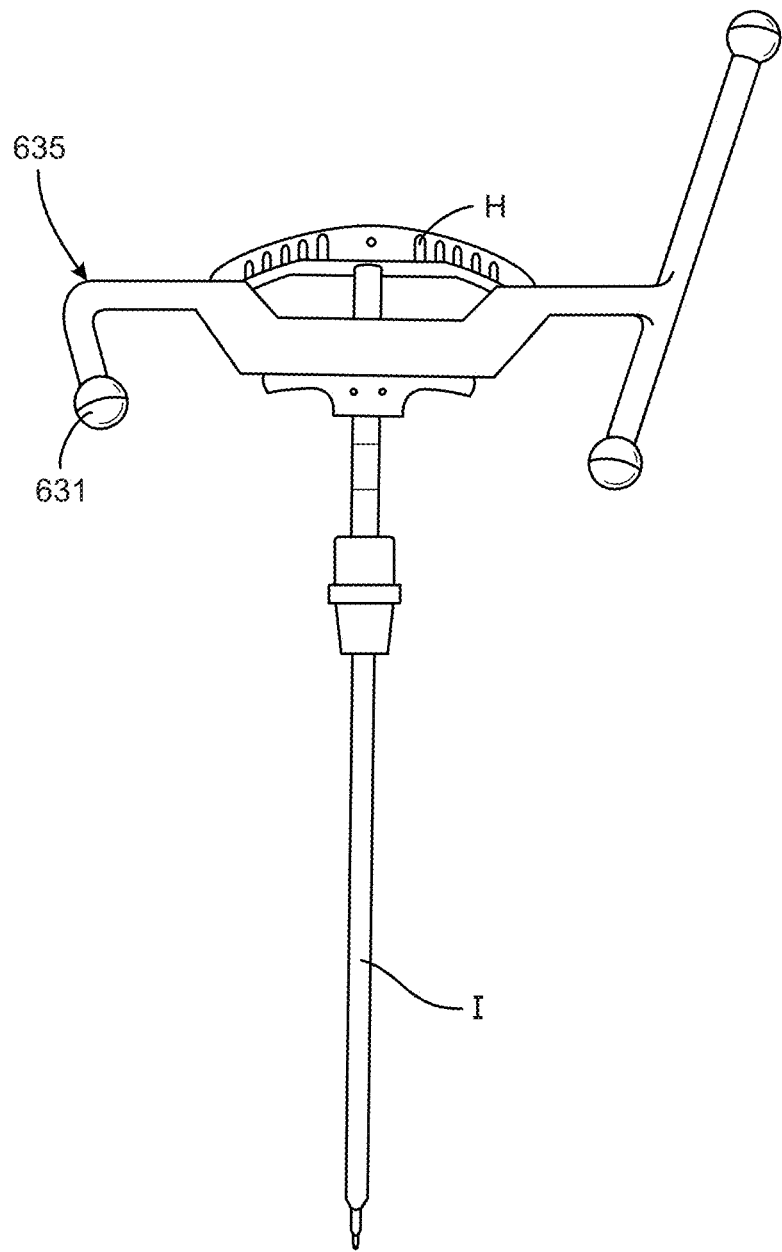
FIG. 55 is a side view of another tracking element mounted on an instrument.

FIGS. 53A, 53B show another three marker tracking element 620 that is configured to be mounted to the proximal end of an instrument. The tracking element 620 includes three arms 621, 622 and 623 with detectable cylindrical markers 624 affixed to the arms. Arms 622 and 623 are aligned along a common axis and arm 621 is oriented perpendicular to that common axis. This configuration allows the same tracking element 620 to be used in a 6 DOF mounting orientation, as shown in FIG. 53A, or in a 5 DOF orientation, as shown in FIG. 53B. In the 6 DOF orientation, the arm 621 includes a tang 625 that can engage a flat F at the end of the instrument I, as illustrated in FIG. 53A. This engagement allows the tracking element 620 to rotate with the instrument, thus providing the sixth (roll) degree of freedom. On the other hand, in the 5 DOF orientation, the arm 623 is provided with a cylindrical bore 626 that is seated on the end of the instrument I shown in FIG. 53B but without the tang. The tracking element 620 is thus free to rotate apart from the instrument. It can be appreciated that in either configuration there is at least one cylindrical tracking marker that is off-axis from the longitudinal axis of the tool/instrument on which the tracking element 620 is mounted.

Alternative 3-marker snap tracking elements 630 (FIGS. 53A-53D), 635 (FIG. 55) are provided for mounting on various instruments to provide 5 and 6 DOF tracking of the instrument. It can be noted that the tracking elements can support spherical markers, such as markers 631 shown in FIG. 54B and FIG. 55, or cylindrical, such as markers 632 shown in FIGS. 54C-54D. The tracking elements 630 and 635 are configured to be mounted on a handle H of an instrument. When mounted on the instrument the markers are off-axis relative to the longitudinal axis, thereby adding degrees of freedom of detection of the markers.

Figure 56A:
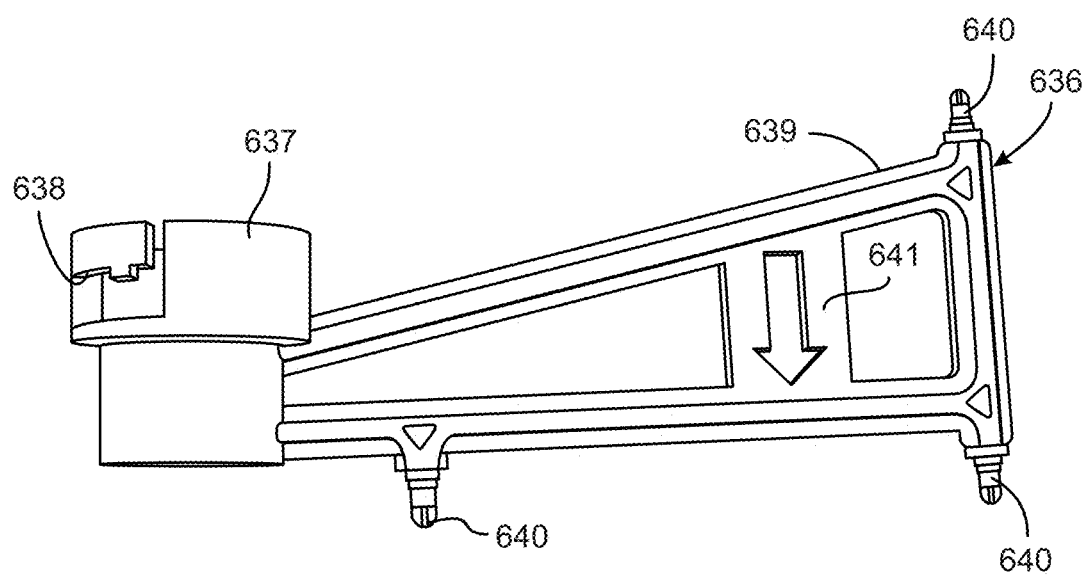
FIGS. 56A-56B are views of a further embodiment of a tracking element, including a view mounted on an instrument.
Figure 56B:
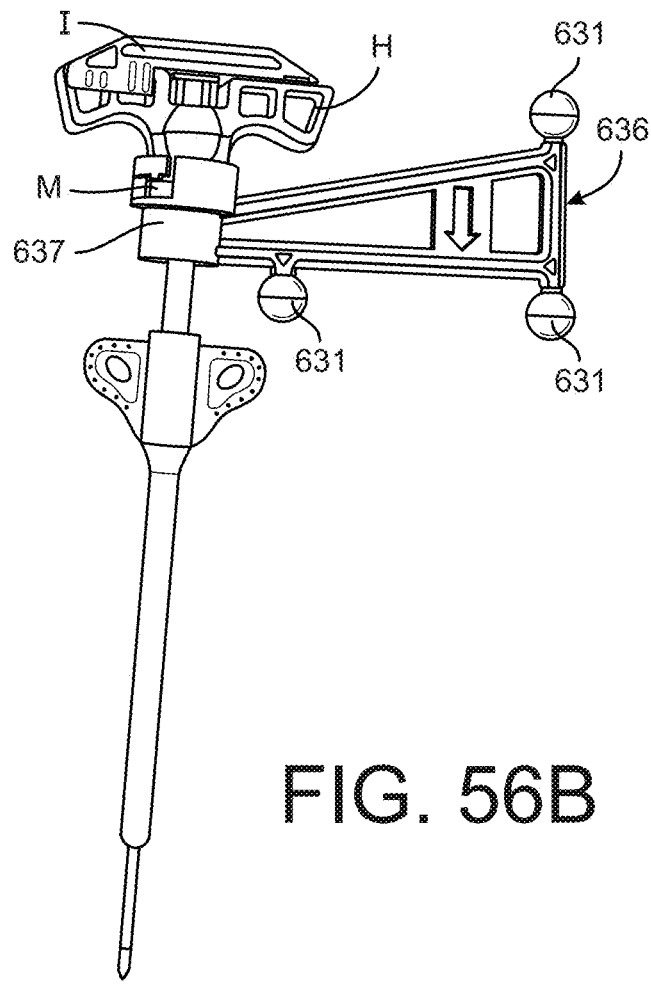

Tracking element 636 is configured to be engaged on the shaft of an instrument or instrument component that has a mating feature, as shown in FIGS. 56A-56B. The tracking element 636 includes a collar 637 configured to be received on the shaft of a handle H for instrument I, as shown in FIG. 56B. The collar 637 includes an engagement feature 638, which can be a bayonet mount, which is configured to engage a mating feature M on the shaft of the handle H. The tracking element 637 includes a frame 639 that supports three posts 640 at predefined orientations relative to the collar, in a manner similar to the tracking elements described above. Like the tracking element 630, the posts 640 of tracking element 636 are configured to support the spherical markers 631. The frame 639 is further configured with a positioning arrow 641 that is intended to point downward toward the working end of the instrument when the tracking element is properly installed on the instrument or handle.

The tracking element 642 shown in FIGS. 57A-57C is also configured to be engaged on the handle H of an instrument I. The tracking element 642 includes a pair of clips 643 that are configured to clip onto the base B of the handle H, as best seen in FIG. 57C. The element includes a frame 644 that supports posts 645 that are configured like the posts 640 to support spherical markers 631, as well as the mounting direction arrow 646.

Figure 58D:
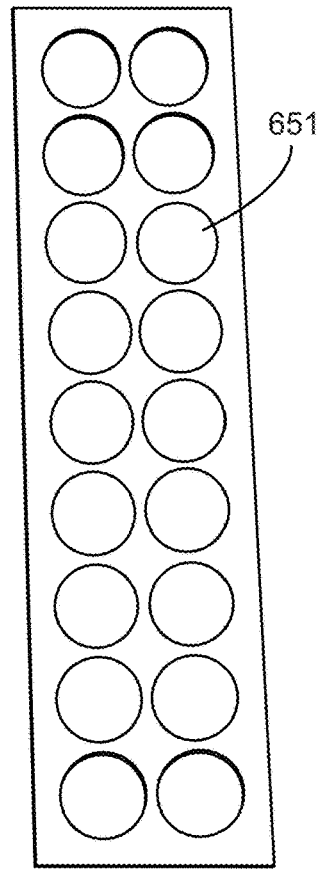
FIG. 58D is a top view of a sheet of disc-type tracking components used with the tracking element of FIG. 58A.
Figures 58B, 58C:
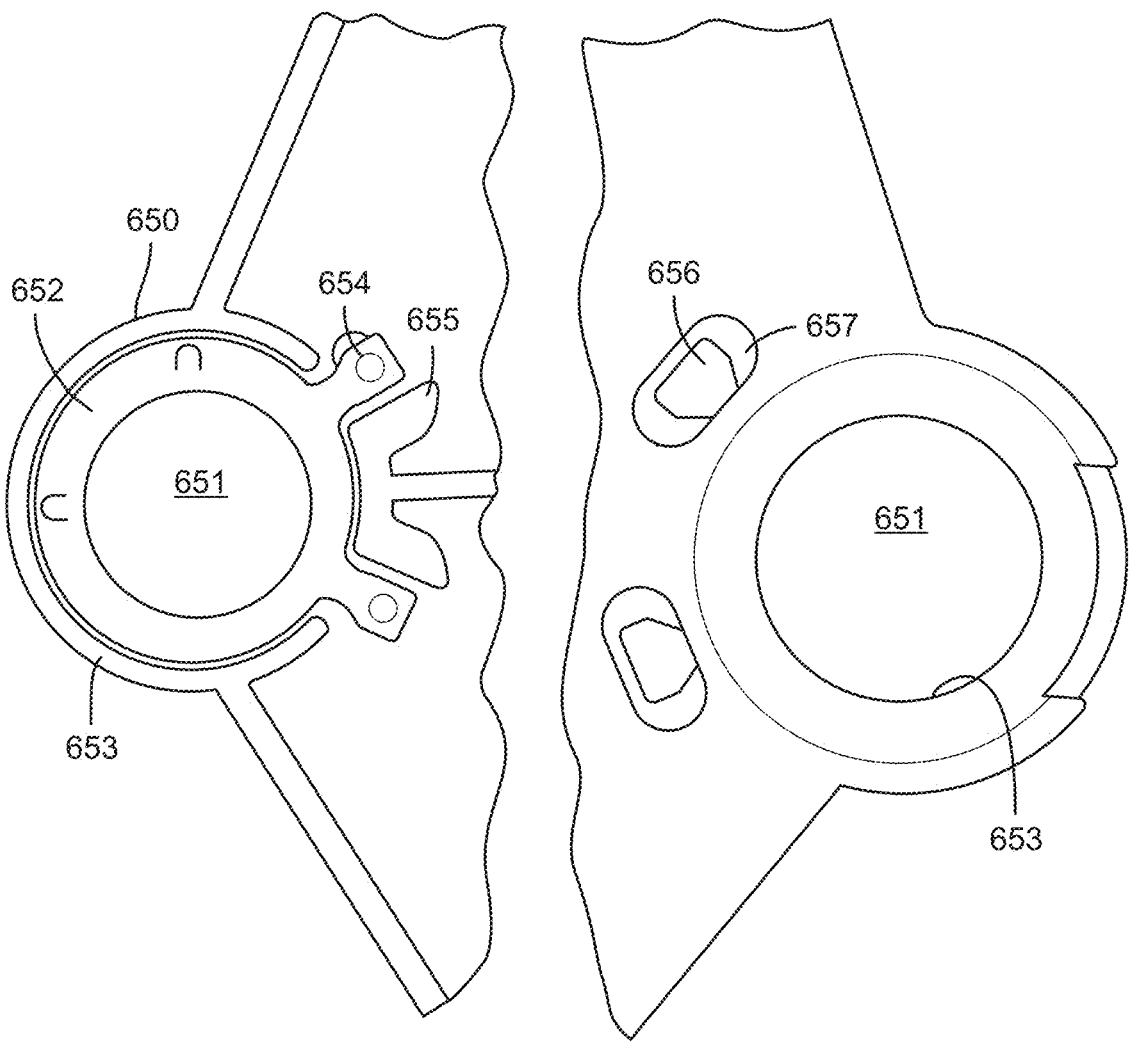
FIGS. 58B-58C are enlarged views of a disc mounting component of the tracking element of FIG. 58A.

The tracking element 647 shown in FIGS. 58A-58D supports disc-type markers 651. The tracking element includes a collar 648 similar to the collar 637 of the tracking element 636 (FIG. 56A) and a frame 649 that supports disc mounts 650 at predefined positions relative to the collar. The disc mounts, shown in detail in FIGS. 58B-C, include a circular clip 652 that is configured to be seated within a circular recess 653 formed in the frame 649. The recess 653 supports the disc marker 651 so that the marker is visible on both sides of the frame. The clip 652 is annular so that the disc is also visible through the clip. The clip 654 includes arms 654 that wedge between the recess 653 and a stop 655. Posts 656 on the ends of the arms 654 fit through holes 657 in the frame to engage the frame. The disc mounts 650 thus provide a means for inserting, removing and replacing the disc markers 651. It is contemplated that the disc markers 651 can be provided in a sheet, as shown in FIG. 58D, in which individual markers can be pressed out of the sheet and mounted in the tracking element 647.

As discussed above, calibration of the position of the tracking element is essential to proper determination of the position and orientation of the instrument and its working end. One approach is the calibration tool 580 shown in FIGS. 49-50. In another approach the tracking element is mounted at a pre-defined location on an instrument, for instance at the end of the instrument. The working end of the instrument is then tapped against a tracked surface, at which time the tracking device 130 (FIG. 1) is activated and the image processing device 122 is operated to measure the distance between the tracked surface and the tracking element. The measured distance corresponds to unique instruments, so when the image processing device identifies the distance it also identifies the instrument and the position and orientation of the tracking element on that instrument. With this approach, the same snap tracking element can be mounted on different instruments, all having a pre-defined mounting location, but the image processing device can still determine the instrument and tracking element relationship to be able to accurately track the working end of instrument throughout the image-guided procedure.

Figure 59B:
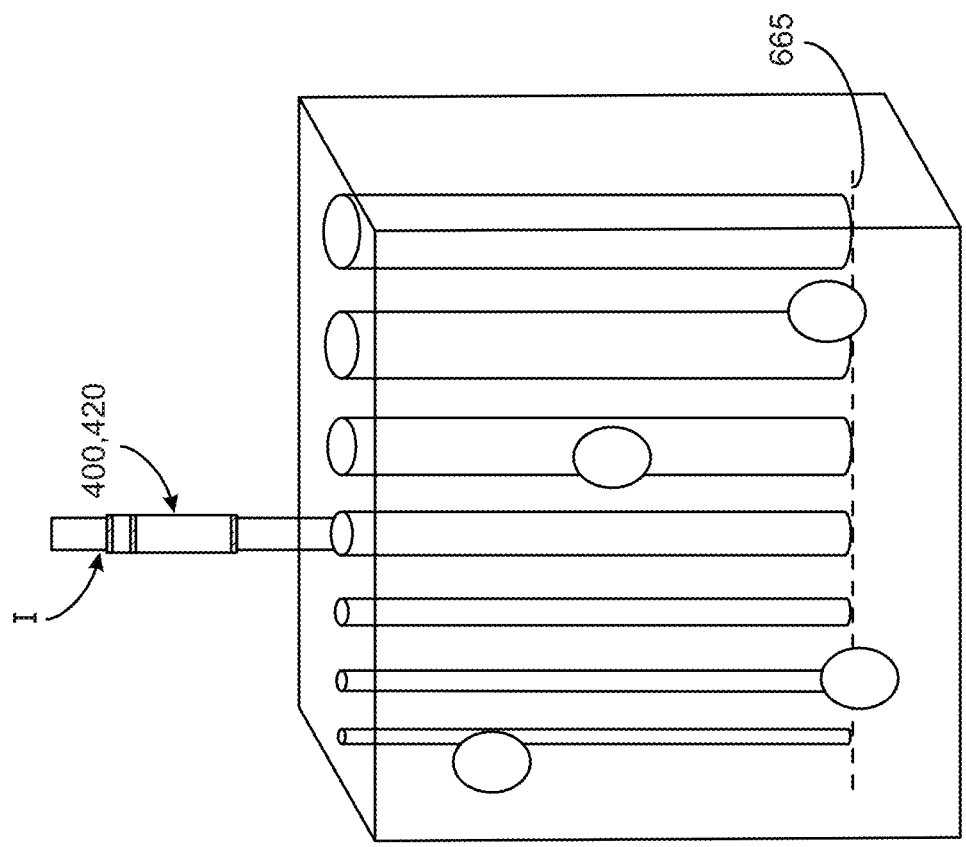
FIGS. 59A-59B are views of a calibration device for calibrating the position of an axial tracking element on an instrument.
Figure 59A:
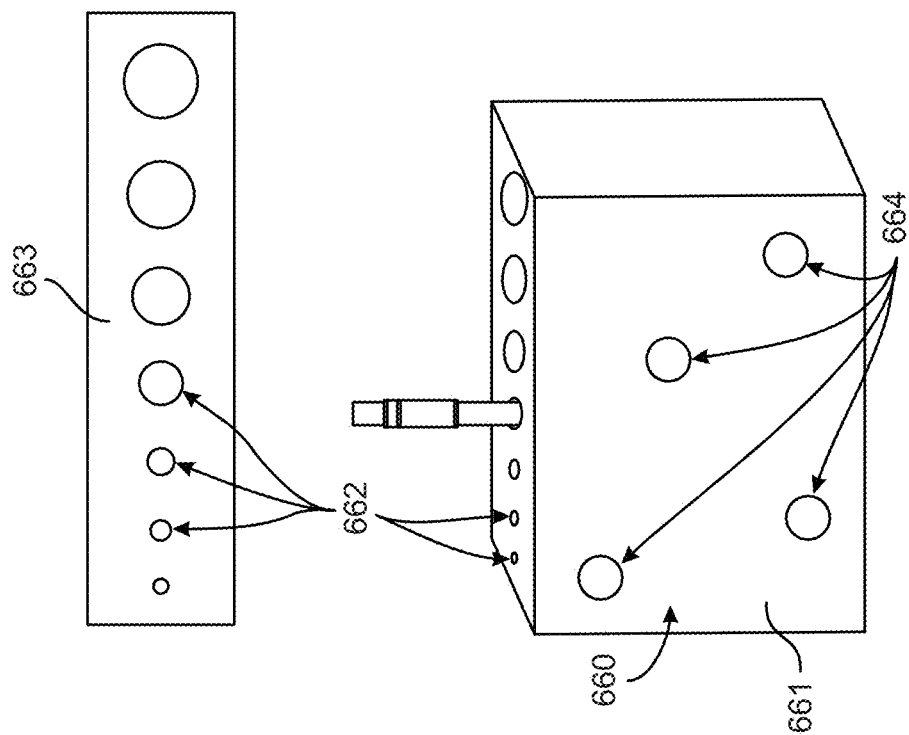

In another approach, a tracked calibrator 660 is provided as illustrated in FIGS. 59A, 59B. The tracked calibrator is a solid body 661 adapted to be seated on a tracked surface that can be visualized by the tracking device 130. The body defines a series of bores 662 extending downward from the upper face 663 of the body to a pre-defined depth 665 (FIG. 59B). The bores have different diameters to accommodate differently sized instruments, with the goal being to provide a snug fit for an instrument inserted into a particular bore, and more particularly to ensure that the instrument is vertically oriented within the tracked calibrator 660. This tracked calibrator is particular suited for calibrating an instrument with in-line tracking markers, such as the bands 44a, 44b, 44c of FIG. 8B, or the in-line tracking elements 400, 420 shown in FIGS. 37-39. As discussed above, the markers or bands define a vector along the length of the instrument so that the intersection of the axis of the instrument and the tracked calibrator 660 is automatically known. Fiducials 664 on the body 661 of the tracked calibrator can be detected by the tracking device 130 and used by the image processing device 122 to determine the location of the tracking device. The tracking device can also determine the location of the tracking elements on the instrument, and from this information the processing device can calculate the length of the instrument from the markers to the working end, which information can then be used to track the working end of the instrument during a procedure.

An X-ray based calibration process utilizes an image of the instrument with the tracking device mounted thereon. The image processing device with the tracking device mounted thereon. The image processing device 122 can detect the proximal and distal working ends of the instrument, such as by using edge detection techniques, and then determine a length of the instrument. This length can be a unique identifier of the particular instrument. The image processing device further detects the distance of the tracking element from the working end. This dimension coupled with the identification of the particular instrument is then used by the image processing device to track the movement and position of the working end of the instrument within the surgical site based on the movement and position of the tracking element outside the surgical site. In certain embodiments, a visual indicator, such as a brightly colored pointer, can be used by the image processing device as an overlay on the X-ray image to indicate the location of the instrument tip.

Figure 60:
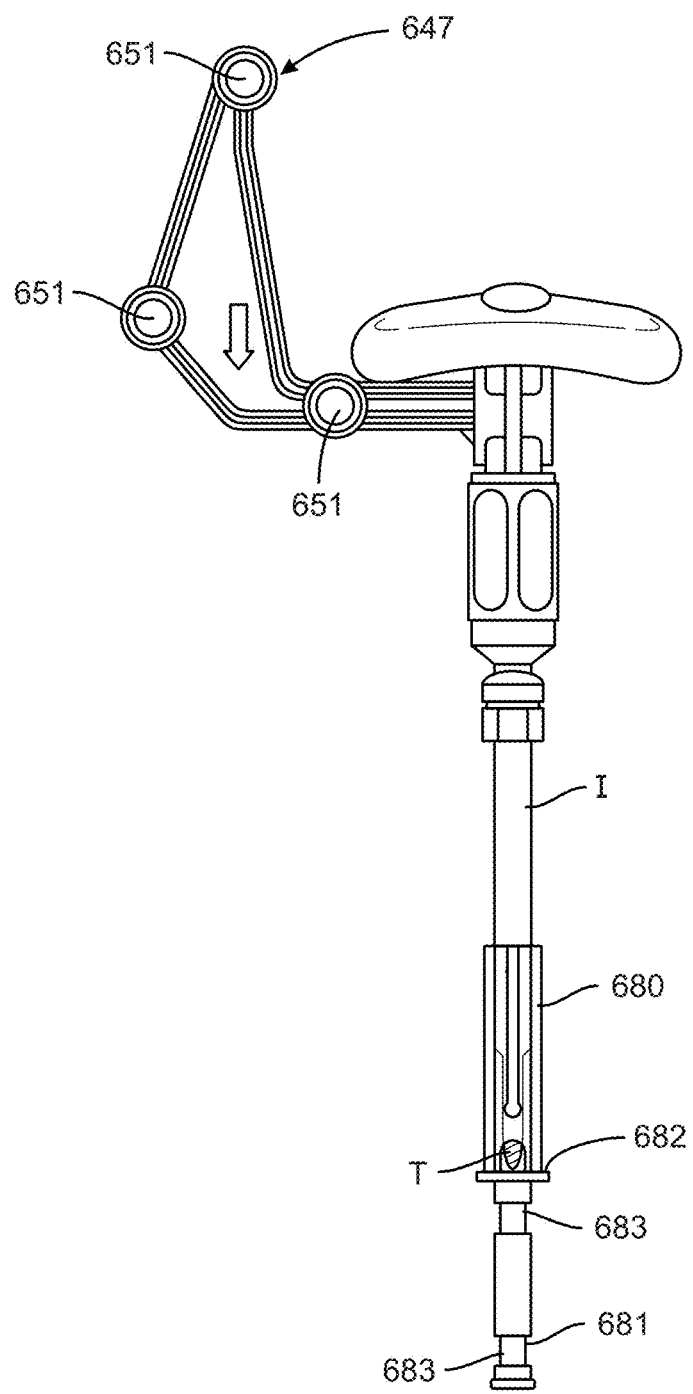
FIG. 60 is a side view of a tracking element mounted on an instrument with a length calibration tool.

One method for determining the length of an instrument I is depicted in FIG. 60. In this method, a cylindrical sleeve 680 is configured to be snugly mounted over the working end or tip T of the instrument. The sleeve 680 includes a base 682 against which the instrument tip T is positioned when the instrument is fitted within the sleeve. A pedestal 681 includes markers 683 that are detected by the system tracking device 130. The tracking device also tracks the position of the disc markers 651 of the tracking element 647. Based on the global positions of the pedestal markers 683 relative to the tracking element markers 651, the image processing device 122 can determine the length of the instrument I in relation to the tracking element 647. The sleeve 680 is removed and the instrument I is available for use in the surgical site, with the location of the working tip T known by the image processing software.

In some procedures, the surgeon is not interested in the alignment of the instrument itself, but rather the alignment of a hole through the instrument. In this instance, a calibration device 700 is used to calibrate the position of a hole H in an instrument I carrying a tracking element, as depicted in FIG. 61A. The calibration device is similar to the device 650 (FIG. 59A) in that the body 701 includes fiducials 702 used to establish the position of the device by a detector 130. In this device, an elongated probe 705 projects from the body 701 in a fixed relation to the fiducials 702. The probe 705 is sized to extend snugly through the hole H in the instrument I. The probe 705 defines a transverse vector V. This vector V is associated with the instrument I based on its relationship to the tracking element 710. Once this relationship is established, the image processing device 122 can detect the position and orientation of the tracking element 710 to know the location and orientation of the common axis of the hole H when the instrument is within the patient's body. A "universal" calibration device 700' can include a stepped probe 705', shown in FIG. 61B in which the cylindrical components 706a-706d have increasingly larger diameters to fit within standard-sized holes in conventional tools and instruments.

As mentioned above, the location of the markers on the effecter can be used to identify the nature of the effecter— i.e., as a tool, instrument, implant etc. The imaging software remembers what effecters are in the surgical field as well as the positions as they are moved within that field. Even if one of more of the markers are temporarily blocked from view of the localizer or tracking device, the imaging software can extrapolate the position of the effecter based on the position of the available markers.

In a further aspect of the invention, the image processing software can be configured to automate certain features of the system based on the type of effecter detected and the nature of the procedure. The software can permit the surgeon to identify the nature of the surgical procedure, and then this information together with the information regarding the effecter or effecters in use can be used to toggle certain display features. The toggled features can include metal enhancement (as discussed herein), the nature of the slugs displayed on the x-ray image, or the use of one or two adjacent views (such as AP and lateral at the same time).

Figure 11:
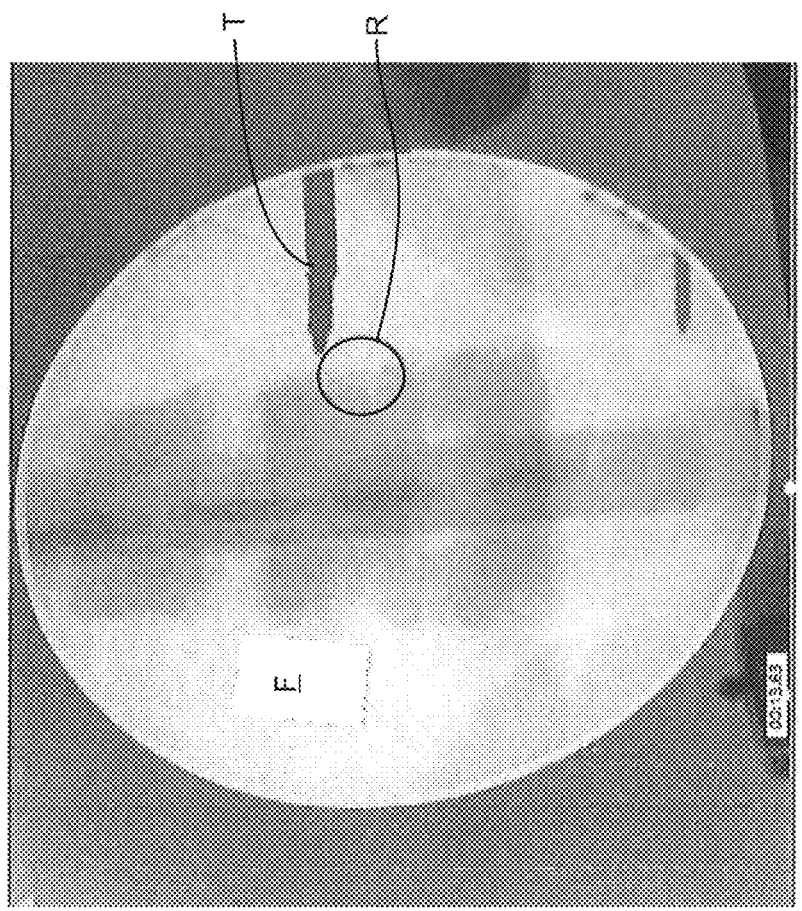
FIG. 11 is screen shot of an x-ray image of a surgical field with an effecter and a region of interest within the viewing field.

The system described above provides a method for tracking an effecter, such as a tool T within a displayed field F, as illustrated in FIG. 11. The present disclosure further contemplates imaging software implemented by the image processing device 22 (FIG. 1) that is activated only when the tracked radio-dense object, such as tool T, enters the surgical field F and a new image has been taken by the C-arm technologist or surgeon. When these two conditions occur, an object mask for the tool, such as the green mask 20, is displayed and the image may be manipulated by the surgeon based on manipulations of the effecter or other radio-dense object. The software remains activated until a new image is taken that does not include the tracked instrument. If the radio-dense object reappears in the field F, the software remembers the original location of the field and the tool and allows manipulation by the C-arm technologist or surgeon.

The software of the present disclosure thus provides a metal identification feature that is always running in the background of the imaging software execution. The software automatically identifies the presence of a radio-dense object in the surgical field without any operator intervention, and displays an image of the radio-dense object without operator intervention. The present disclosure thus contemplates a system for identifying a radio-dense object in an image field and enhancing the display of that object for the benefit of the surgeon attempting to navigate the object within the surgical field. The software disclosed herein thus identifies the nature and parameters of the radio-dense object without any input or intervention from the C-arm technologist or surgeon. The software analyzes the x-ray image to locate the radio-dense object or objects and then create a mask corresponding to the configuration of the object. When the object is moved, the software can move only the object mask without modifying the underlying image of the surgical field. In one approach, the software utilizes existing tracking data for the guided surgical tool to identify the region of the image field in which the tip of the instrument or tool can be found, and/or a general angle of projection of the tool on the x-ray obtained from the existing tracking data. The present disclosure thus provides a system that can locate a tool T even where the tracking data only identifies a region R within the viewing field F (FIG. 11).

Once the radio-dense object is located, the software and system of the present disclosure enhances or intensifies the image of the radio-dense object. As shown in FIG. 12A, some radio-dense objects M are difficult to see in a low dose image. As shown FIG. 12C, the problem is exacerbated when the low dose image is merged with a prior standard dose image (FIG. 12B), such as according to the techniques described U.S. Pat. No. 8,526,700, which issued on Sep. 3, 2013, the entire disclosure of which is incorporated herein by reference. The present disclosure contemplates software executed by the image processing device 22 (FIG. 1) that identifies the location of the radio-dense object(s) M, even in an image field as shown in FIG. 12A, and then intensifies the radio-dense objects M' in a composite image shown in FIG. 12C so that the radio-dense objects are sufficiently visible to the surgeon. The software can locate the radio-dense object directly from the image FIG. 12A, or can use angle of projection and/or location data provided by an image guidance component, to speed up the process of identifying the location of the radio-dense object(s) M. The system and software disclosed herein thus provides means for locating and enhancing incredibly faint objects within the viewing field, even when the image is a low dose image. Once the radio-dense object(s) M' are located and enhanced, only the enhanced radio-dense object is moved while the underlying baseline or composite x-ray image can remain stationary since only the object is being tracked. It is further contemplated that the tracked objects can be limited to only select ones of the radio-dense objects that may appear in a particular field of view. The non-tracked radio-dense objects can remain un-enhanced and left stationary even as the image moves with the tracked radio-dense objects M'. Moreover, any one or multiples of radio-dense objects in an image can be identified, enhanced and moved independently as independent masks overlying a baseline or composite x-ray image. With this feature, multiple physicians can work simultaneously and together to position radio-dense objects necessary for the surgical procedure, all working from the same underlying stationary baseline or composite x-ray image.

Figure 13C:
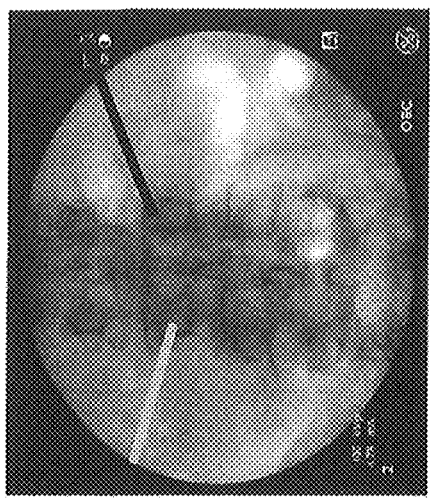
FIGS. 13A-F are screen shots of x-ray images of multiple radio-dense effecters in a surgical field with images of the effecters isolated and represented by metal masks overlaid onto the image of the anatomy.
Figure 13F:
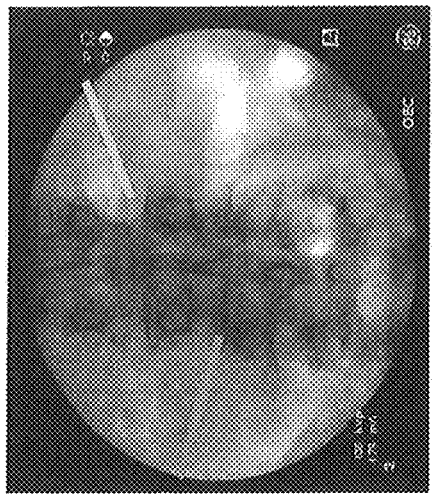
Figure 13B:
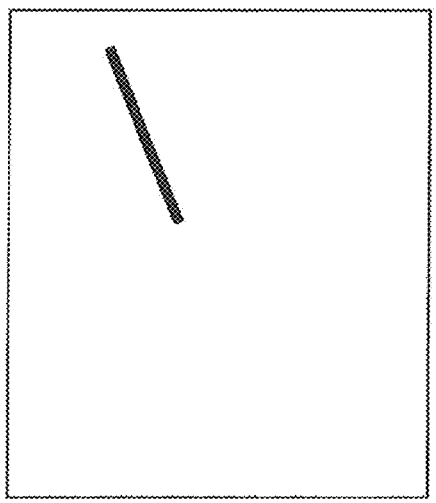
Figure 13E:
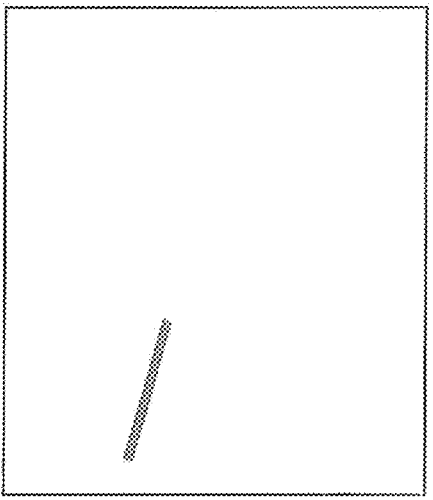
Figure 13A:
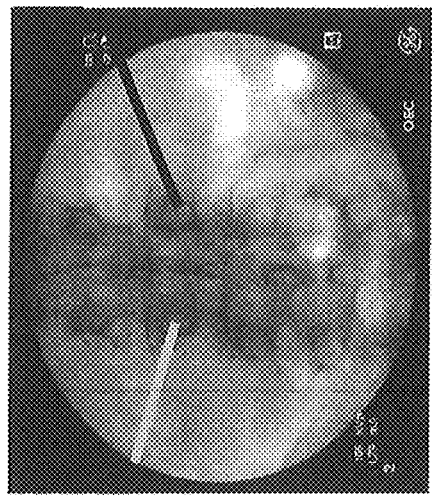
Figure 13D:
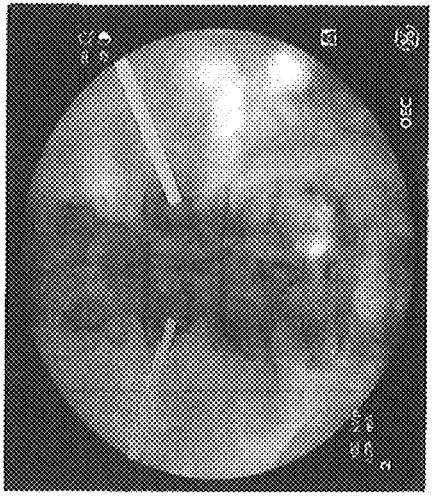

The system and software of the present disclosure allows isolation of a radio-dense object within an image, such as the image FIG. 13A and the isolated image in FIG. 13B. The isolated image can be used to guide movement of the radio-dense object which can then be reintegrated with the x-ray image at a new location as shown in FIG. 13C. This process can be performed with any radio-dense object, once it has been identified, as illustrated in FIGS. 13D-F. The radio-dense objects can be represented by a mask, with the masks for multiple objects being color-coded, as shown in FIG. 13F.

FIGS. 14A-F shows a series of screen shots of displays generated by the present system and software. The first image in FIG. 14A, shows a faint object M in a low radiation image. It is apparent from this image that the radio-dense object M is too faint for a surgeon to reliably manipulate the instrument or tool. In the composite image of FIG. 14B the radio-dense object is even fainter. FIG. 14C shows an image of one step in the metal identification algorithm implemented by the software of the present disclosure which relies on identifying linear edges that are indicative of a non-anatomic feature. When tracking information for the particular effecter or object is added, as shown in FIG. 14D, the correct linear edge is identified as the radio-dense object, which is then enhanced and displayed in the image of FIG. 14E.

Figure 15D:
FIGS. 15B-D are screen shots of an x-ray image showing the movement of the image corresponding to the movement of the c-arm in FIG. 15A.
Figure 15C:
Figure 15B:
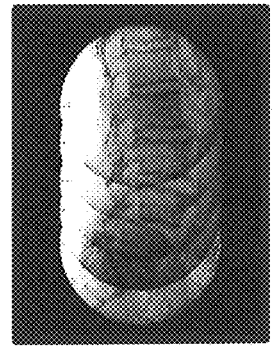
Figure 15A:
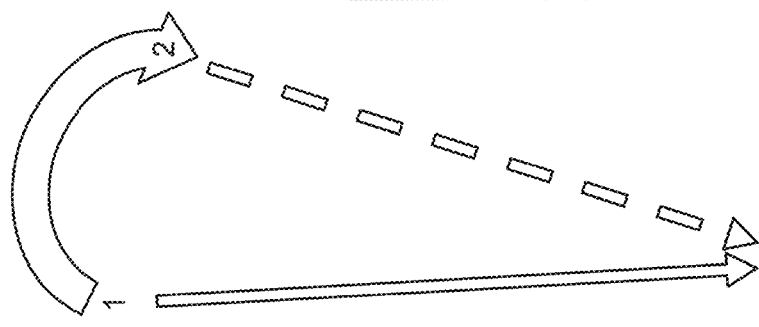
FIG. 15A is a representation of a movement of the x-ray device or c-arm during a surgical procedure.

The system and software further provides two ways to view movement of a tracked radio-dense object within a surgical field. The system described in U.S. Pat. No. 8,526,700, incorporated by reference above, provides a system for orienting a view as the x-ray device or C-arm is angled, as depicted in FIG. 15A. In this system, when the C-arm is moved from position 1 to position 2, the displayed images move from the position in FIG. 15B to the position shown in FIG. 15C. In FIG. 15D, grid lines are added that can ultimately be used to orient the C-arm to a perfect alignment for a Ferguson (flat endplate) view of a spinal field from the orthogonal x-ray image. The grid lines are parallel to the orientation of the effecter or radio-dense object.

Figure 16C:
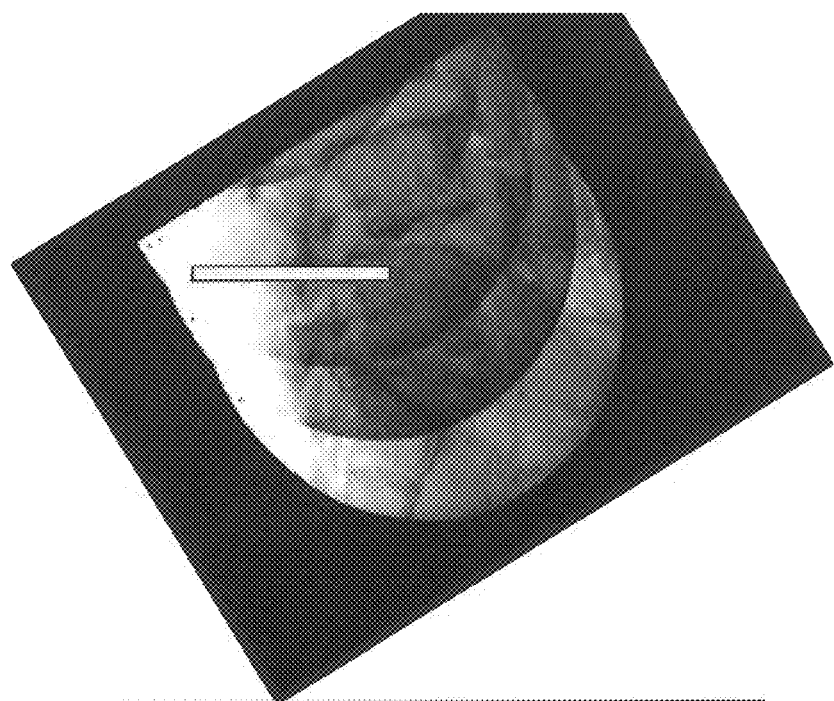
FIGS. 16B-C are screen shots of an x-ray image showing the movement of the image corresponding to the movement of the radio-dense effecter in FIG. 16A with the position of effecter remaining stationary.
Figure 16B:
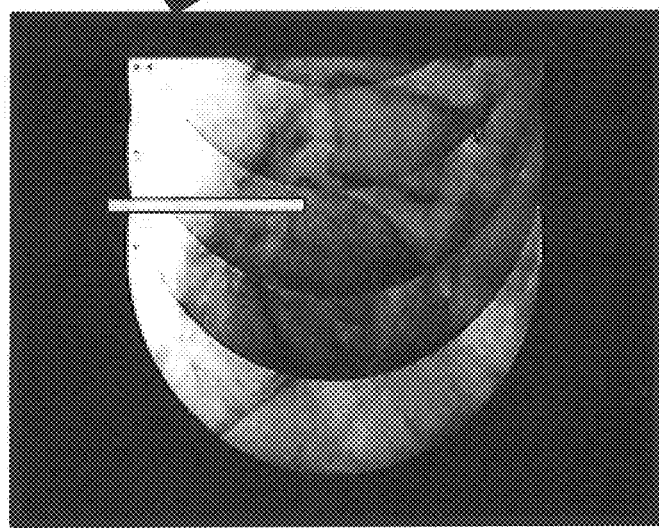
Figure 16A:
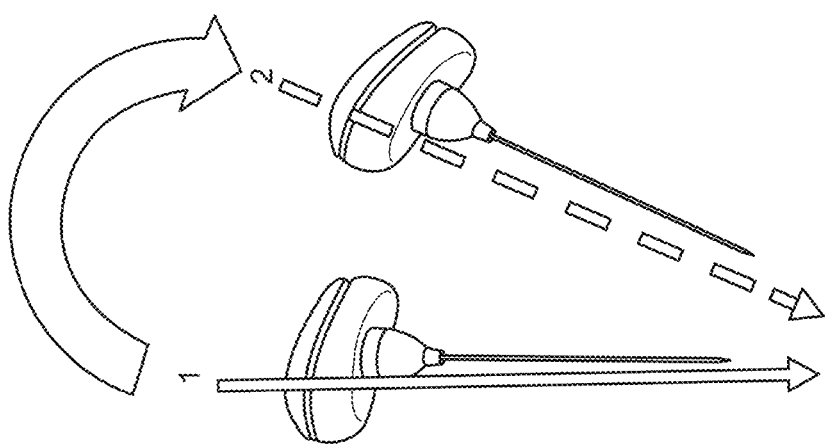
FIG. 16A is a representation of a movement of a radio-dense effecter during a surgical procedure.

In accordance with the present disclosure, when the radio-dense effecter or tool is moved, as shown in FIGS. 16-17, the tracked object controls the angle of the displayed image. The tracked object shown in FIG. 16A is maintained in a constant orientation (such as vertical in FIG. 16B) and the x-ray image itself is rotated commensurate with the movement of the tracked object, as shown in FIG. 16C. It can be appreciated that the change in angular orientation of the image between FIG. 16*b* and FIG. 16C is the same as the change in angular orientation of the effecter from position 1 to position 2 in FIG. 16A. In one feature, the working tip of the tracked object is identified and the image is rotated about the working tip, as shown in FIG. 16C. The x-ray image is also translated upon translation of the working tip of the effector, or translated and rotated when the working tip is translated and rotated. In other words, the physical movement of the effector is depicted by a commensurate movement of the x-ray image while the depiction of the effector remains stationary in the image.

As an adjunct to this feature, the image data for the rotated image of FIG. 16C can be used to identify a movement for the c-arm to produce a desired shot of the effecter and the surgical site. For instance, the image data can be used to identify a movement angle for the c-arm to generate an en face view down the shaft of the effecter. Similarly, the image data can be used to center the c-arm over the shaft of the effecter or angle the c-arm to shoot perpendicular to the effecter shaft and centered over the tip of the instrument.

For instance, as shown in FIG. 62A, an instrument I is at a desired fixed position relative to the anatomy, but the cone beam CB of the X-ray is offset. In particular, the central axis $A_{CB}$ of the cone beam is offset from the longitudinal axis L of the instrument, as shown in FIG. 62A. The desire is to align the two axes, as shown in FIG. 62B, by moving the X-ray so that the axis of the cone beam is aligned with the fixed axis of the instrument. To facilitate this alignment, a circle is superimposed on the X-ray image of the instrument at each of two locations on the instrument. Position P1 is situated at the tip or working end of the instrument and position P2 is offset toward the handle of the instrument (or toward the X-ray device). In the orientation shown in FIG. 62A in which the cone beam is angularly offset from the axis L of the instrument, the two circles are offset in the image, as depicted in FIG. 62C. The X-ray device is moved until the two circles overlap, as depicted in FIG. 62D, at which point the X-ray device is fixed.

These same procedures can be applied to an instrument shown in FIGS. 63A, 63B in which the axis of interest V extends through a feature of the instrument. As described above, the relationship between this vector or axis V to the instrument is known, and therefore the position of the axis V relative to the X-ray device is also known. The alignment circles at points P1, P2 described above can be situated at opposite sides of the instrument and used in the same way to align the axis $A_{CB}$ of the X-ray cone beam. The same procedure can be used to align the X-ray device relative to an instrument with a wide working end, such as the distraction tool shown in FIG. 64. In this instance, the points P1, P2 are positioned on opposite sides of the working end to define a vector V therebetween. The X-ray can thus be aligned with this vector V by moving the X-ray device until the circles at points P1, P2 overlap, as shown in FIG. 62D.

It is further contemplated that the depiction of the alignment circles can be manipulated by the image processing software. Since the location of the alignment circles P1, P2 are known by virtue of the knowledge of the position and orientation of the instrument, the orientation of the alignment circles can be manipulated to guide movements of the X-ray other than directly along the axis L or vector V. For instance, it may be desirable to align the X-ray device to obtain an image that is perpendicular to the enlarged working end of the instrument shown in FIG. 64. One approach is to align the X-ray device directly along the vector V, as described above, and then move the X-ray device exactly 90° to achieve the desired view. Another approach is to move the circles corresponding to the positions P1, P2 so that the circles are aligned or overlap when the X-ray device is at the desired 90° view. In this instance, the image processing software would determine the location of the points P1, P2 and rotate their angular position about the axis of the instrument to 90°. As the X-ray device is manipulated face on with the wide working end of the instrument the alignment circles move from the position shown in FIG. 62C to the aligned position shown in FIG. 62D.

Figure 17C:
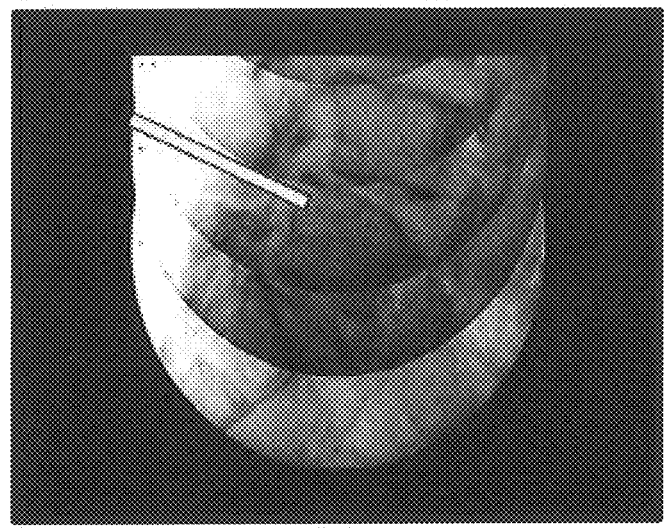
FIGS. 17B-C are screen shots of an x-ray image showing the movement of the image corresponding to the movement of the radio-dense effecter in FIG. 16A with the position of the image of the anatomy remaining stationary.
Figure 17B:
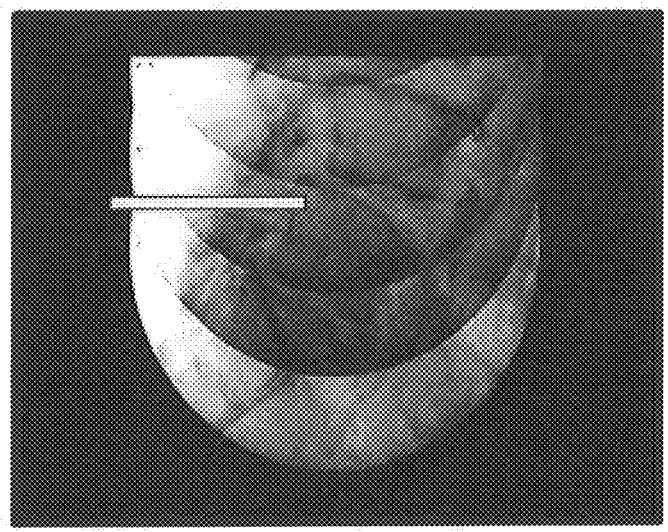
Figure 17A:
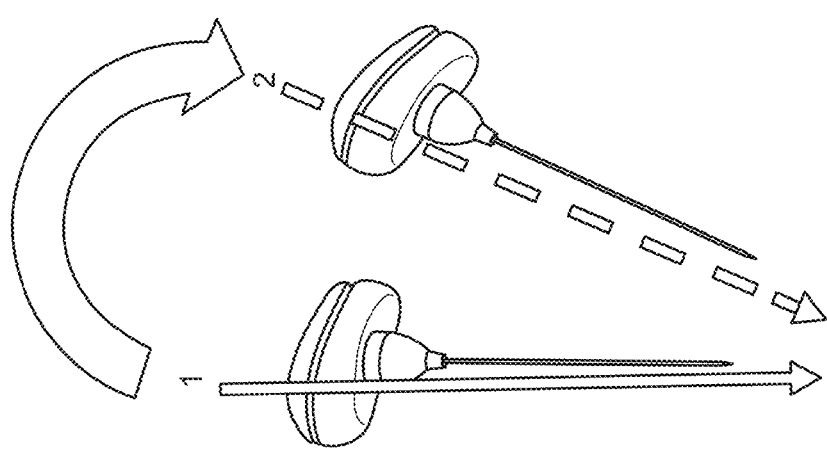
FIG. 17A is a representation of a movement of a radio-dense effecter during a surgical procedure.
Figure 18C:
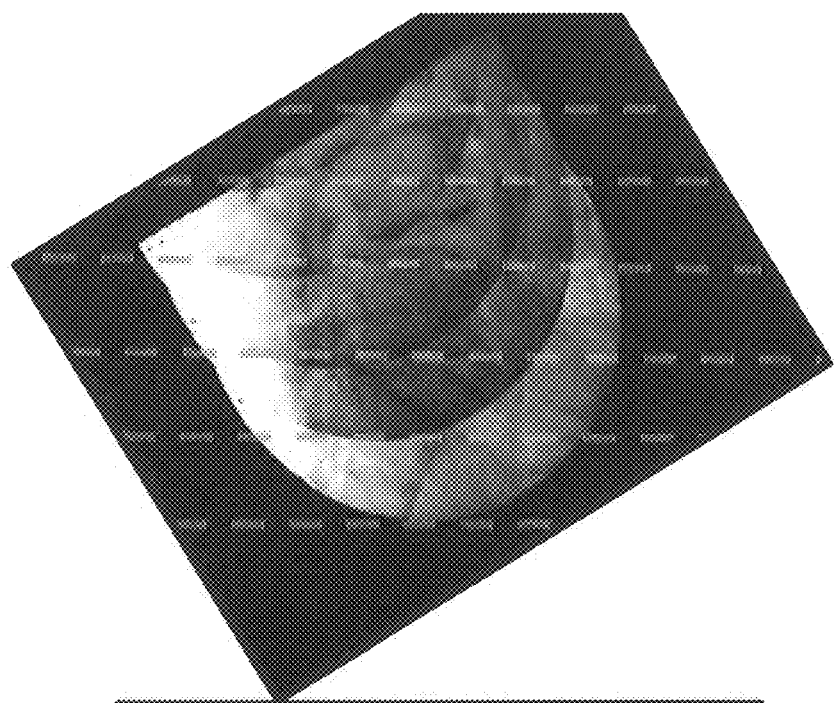
FIGS. 18B-C are screen shots of an x-ray image showing the movement of the image corresponding to the movement of the radio-dense effecter in FIG. 18A with the position of effecter remaining stationary and with grid lines superimposed on the image corresponding to the stationary orientation of the effecter.
Figure 18B:
Figure 18A:
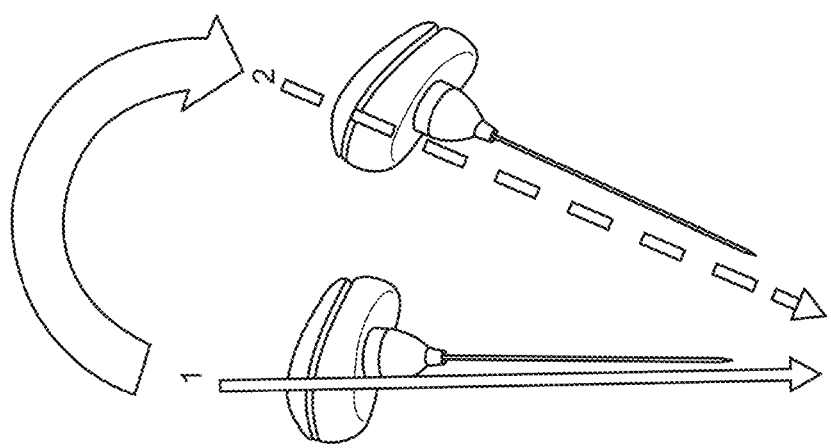
FIG. 18A is a representation of a movement of a radio-dense effecter during a surgical procedure.
Figure 19C:
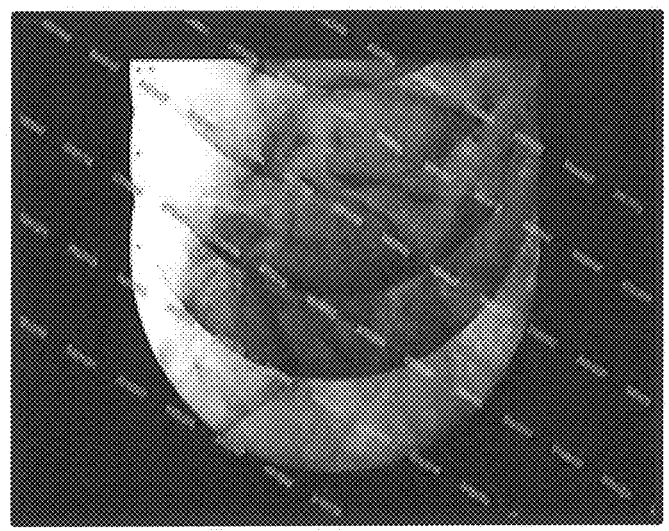
FIGS. 19B-C are screen shots of an x-ray image showing the movement of the image corresponding to the movement of the radio-dense effecter in FIG. 19A with the position of the image of the anatomy remaining stationary and with grid lines superimposed on the image corresponding to the different positions of the radio-dense effecter.
Figure 19B:
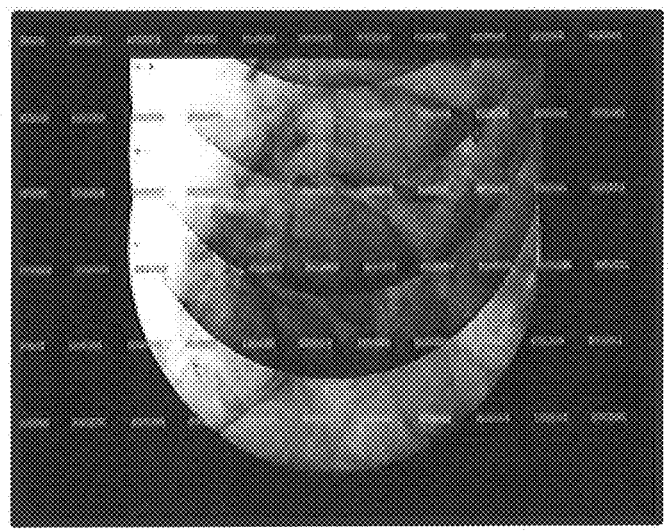
Figure 19A:
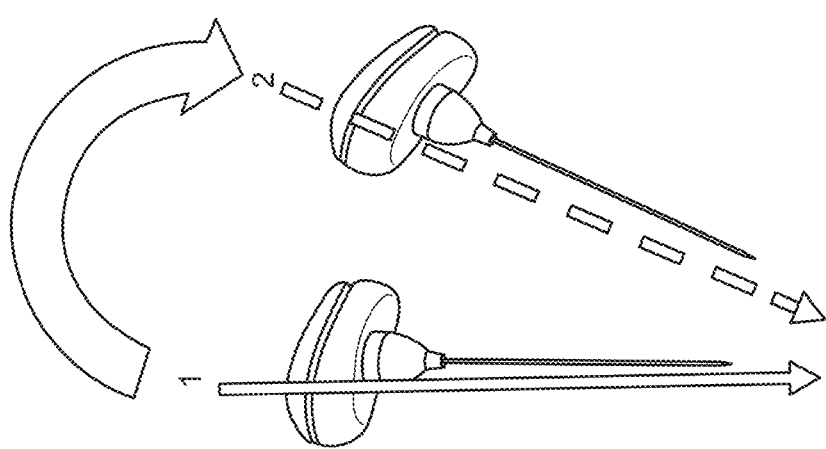
FIG. 19A is a representation of a movement of a radio-dense effecter during a surgical procedure.

Alternatively, as shown in FIGS. 17A-C, the x-ray image can remain stationary while the image or mask of the tracked radio-dense object is moved commensurate with the actual movement of the tracked radio-dense object. The depth of the radio-dense object can be further adjusted by moving the metal mask or image axially along its length. The grid lines can be added to the displays, whether the tracked object remains stationary in the field of view, as in FIGS. 18A-C, or the x-ray view remains stationary and the image or mask of the effecter is moved, as in FIGS. 19A-C.

As described above, the imaging software of the present system implements a method to detect the presence and location of tracked radio-dense objects and enhances the objects. The position and orientation of the radio-dense effecter, such as a tool or instrument, in space with respect to an X-ray device are measured by a tracker or localizer system associated with the effecter. This tracking information is used to translate an X-ray image of the effecter on the viewing screen that predicts where the effecter would appear if another X-ray image were acquired. The image of the tool can be merged with a previously acquired image of the patient's anatomy, with the previously acquired image remaining static. The resulting merged image informs the physician about the placement of the effecter relative to the anatomy.

Figure 20:
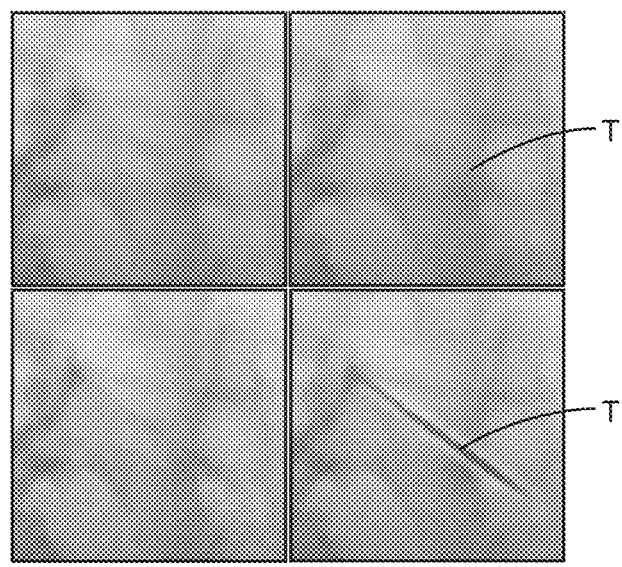
FIG. 20 are screen shots of x-ray images illustrating the low visibility of certain radio-dense effecters in a surgical site.

One problem with this approach is that certain commonly used surgical tools T can be difficult to see in an X-ray image, especially if this image was acquired at a low X-ray dosage, as depicted in the screen shot images of FIG. 20. The visibility of the surgical tool is further diminished by the merging of a baseline image with a subsequent low dose image. Consequently, the present disclosure contemplates a method for enhancing the visibility of a tracked surgical tool in a merged X-ray image.

Figure 21:
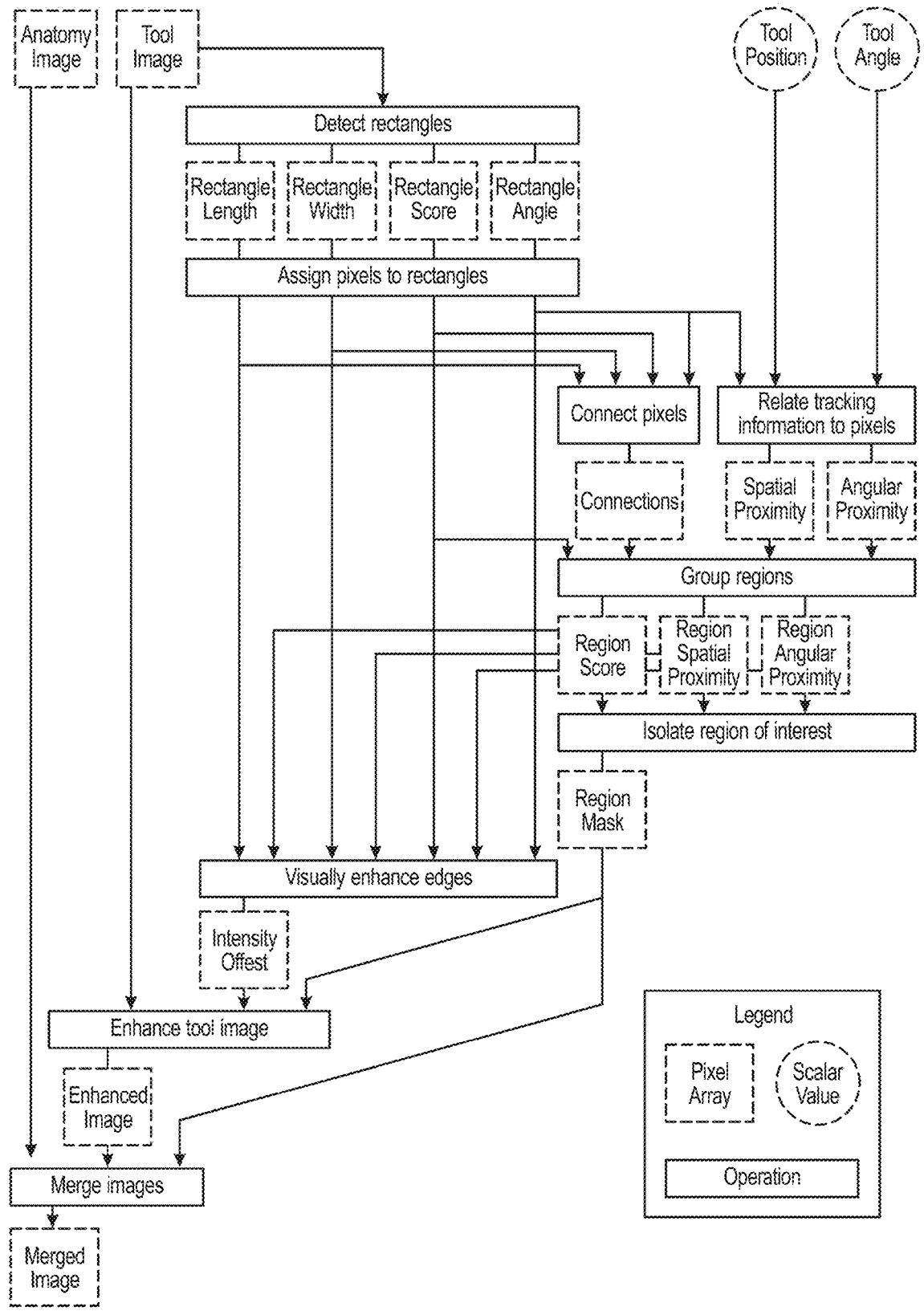
FIG. 21 is a flow chart for detecting the presence and location of a radio-dense effecter in an image of a surgical site.

The steps of one method implemented by the imaging software are shown in the chart of FIG. 21. Several parameters are available to optimize the method for particular classes of surgical tools. All steps have been designed to be straightforward to implement on a graphics processing unit, such as the GPU of the image processing device 122 (FIG. 1), which performs optimally when the same computational operation can be performed at all pixels in an image simultaneously. In the present implementation, the entire operation can be applied to a standard size image in half a second with a consumer-grade graphics card, which suffices for most usage patterns.

Figure 22:
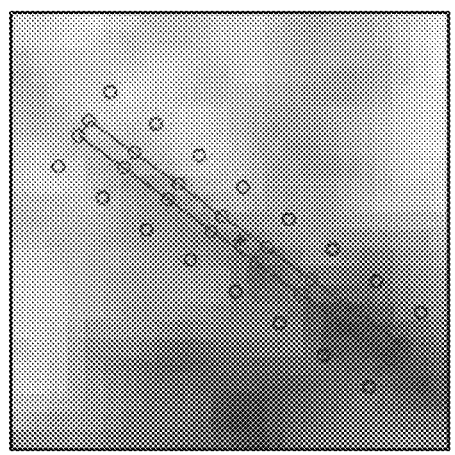
FIG. 22 is a screen shot of an x-ray image of an effecter in a surgical site illustrating one step of the detection method in the flow chart of FIG. 21.

One step of the method is to detect rectangles within the x-ray image. Each pixel is assigned a score that represents how well a dark rectangular pattern can be fitted to the neighborhood centered on the pixel. A rectangle is defined by its angle, width, and length. The score for a particular rectangle is the sum of the differences in the intensity values between points along the inside of the long edges of the rectangle and points along the outside (FIG. 22). This score calculation is performed for many different possible rectangles over a range of angles, widths, and lengths, and the highest score is reported, along with the corresponding angle, width, and length.

When tracking a metal tool that is especially thick, the difference calculation can also be performed at multiple depths in the interior of the rectangle. This ensures that the rectangle has a homogeneous interior. The intensity difference formula can be clamped to a narrow range of possible values, and scaled by a fractional exponent, so that especially large intensity differences will not have a disproportionate influence on the final score.

Figure 23:
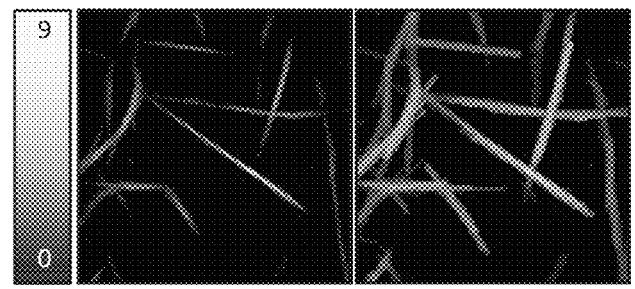
FIG. 23 is a screen shot of an x-ray image of an effecter in a surgical site illustrating a further step of the detection method in the flow chart of FIG. 21.

In a next step, pixels of the x-ray image are assigned to the rectangles. This step extends the results from rectangle detection. For each pixel, the neighborhood around the pixel is searched for the highest-scoring rectangle that overlaps it (FIG. 23). This score is reported, along with the corresponding angle, width, and length. This step is needed because rectangles have corners and intersections, and the pixels at these locations are not centered on the rectangle that best contains them.

Figure 24:
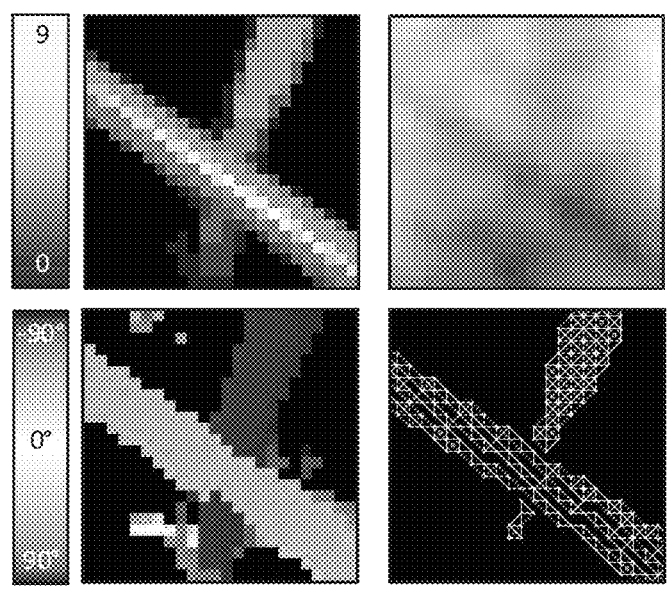
FIG. 24 is a screen shot of an x-ray image of an effecter in a surgical site illustrating another step of the detection method in the flow chart of FIG. 21.

In an X-ray image, a surgical tool may comprise multiple connected rectangles, so it is preferable to join the multiple rectangles together into a single contiguous region. In order to determine whether or not pixels belong to the same region, for two adjacent pixels, each of which has been assigned a rectangle score, angle, width, and length from the previous steps, the connection criterion is the sum of the differences in the rectangle scores, angles, widths, and lengths (FIG. 24). If the connection criterion falls below a threshold, the pixels share a connection. The relative contributions of the scores, angle, widths, and lengths can be weighted in order to control their influence on the criterion. Each pixel has 8 neighbors to which it might potentially be connected. This operation is performed at each pixel for all 8 directions. To reduce computation time, connections between pixels with very low rectangle scores can be ignored.

Figure 25:
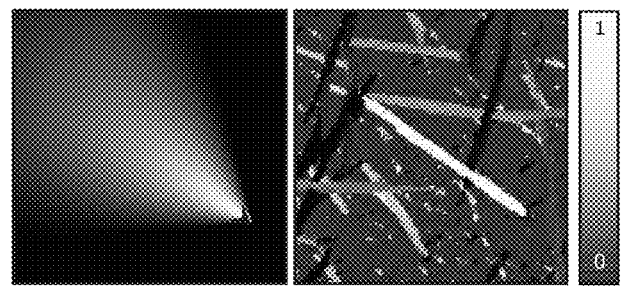
FIG. 25 is a screen shot of an x-ray image of an effecter in a surgical site illustrating a subsequent step of the detection method in the flow chart of FIG. 21.

In the next step the tracking information obtained from the localizer or tracking device for the tool is related to the pixels. The tracking device provides data for the position and orientation of the tip of the surgical tool in space. This tip can be virtually projected onto the surface of the X-ray camera and related to a point and an angle within the X-ray image, as described above. For enhancement purposes, the primary interest is in rectangular image features that have a position and angle that are close to the projected tool tip. For each pixel, the distance to the projected tool tip is calculated, and the difference between the angle of the tool tip and the angle of the rectangle at the pixel is calculated. These values can be clamped and scaled with an exponent to yield weights that quantify the spatial proximity and angular proximity of the pixel to the tool tip (FIG. 25). A tool is typically a long thin object, and pixels behind the tip belong to the object while pixels in front of the tip do not. This prior knowledge can be encoded by including orientation information into the calculation of spatial proximity.

The pixels are then grouped into contiguous regions. Each region will have a unique index, a rectangle score, a spatial proximity, and an angle proximity. These values will be accessible at each pixel in the region. There are various algorithms available for this task. The algorithm used here was chosen because it can be performed at each pixel in parallel. The region growing algorithm proceeds iteratively. At each iteration, for each of 8 possible directions, each pixel looks at its neighbor in that direction. If the pixel shares a connection with its neighbor, then they compare rectangle scores. If the neighbor has a higher score, then the pixel receives the score and the index of its neighbor. Otherwise, if the scores are equal, and the neighbor has a higher index, then the pixel receives the index of its neighbor. If the pixel shares a connection with its neighbor and the neighbor has a higher spatial proximity, then the pixel receives the spatial proximity of its neighbor. If the pixel shares a connection with its neighbor and the neighbor has a higher angular proximity, then the pixel receives the angular proximity of its neighbor. At the end of the iteration, if the index, score, spatial proximity or angular proximity have changed for any pixel in the image, then another iteration is performed. Otherwise, the algorithm halts.

When the algorithm has finished, each pixel has been assigned to a region. Each region has a unique index, and each region has the best rectangle score, spatial proximity, and angular proximity out of all the pixels in the region. These values are stored at each pixel in the region.

Figure 26:
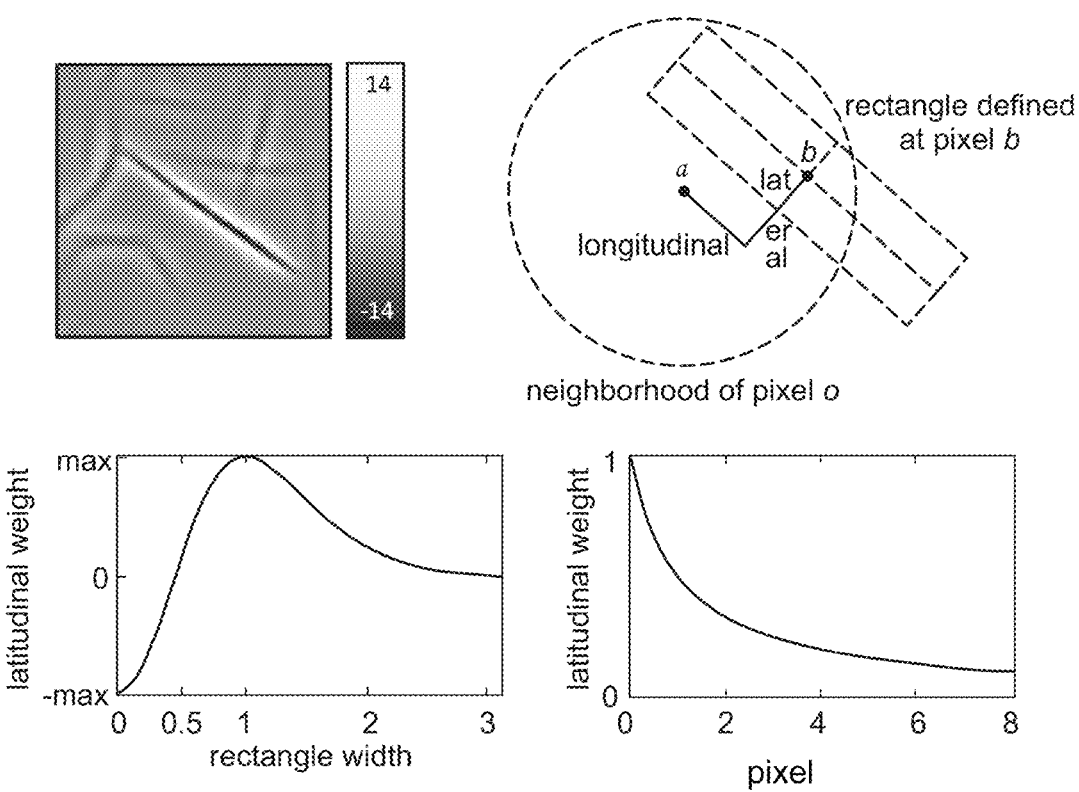
FIG. 26 is a screen shot of an x-ray image of an effecter in a surgical site illustrating yet another step of the detection method in the flow chart of FIG. 21.

Next, the regions are visually enhanced. In an X-ray image, a surgical tool should appear darker than the surrounding area. To enhance visibility, the pixels inside the region can be made darker, and the pixels outside the region lighter (FIG. 26). The changes to intensity should be smooth so that no spurious textures are introduced into the image, and so that the enhancement is robust in the presence of potential errors from the previous steps. Each pixel looks at each other pixel in the neighborhood. The score, angle, width, and length of the rectangle centered at the neighbor are found, as well as the score, spatial proximity, and angular proximity of the region to which the neighbor belongs.

The latitudinal and longitudinal axes of the neighboring rectangle are determined. The distance between the pixel and its neighbor is expressed as a sum of a latitudinal component and a longitudinal component. The latitudinal component is passed to a difference-of-Gaussians model that returns a negative value for pixels within the interior of the rectangle and a positive value in the exterior. The longitudinal component is passed to a hyperbolic model that returns a fraction that approaches 0 as the longitudinal distance grows. The offset to the pixel contributed by this neighbor is a product of the rectangle score, region score, spatial proximity, angular proximity, latitudinal weight, and longitudinal weight. The offsets from all neighboring pixels are added together. This step yields an intensity offset that can be used in the image merging step.

Figure 27:
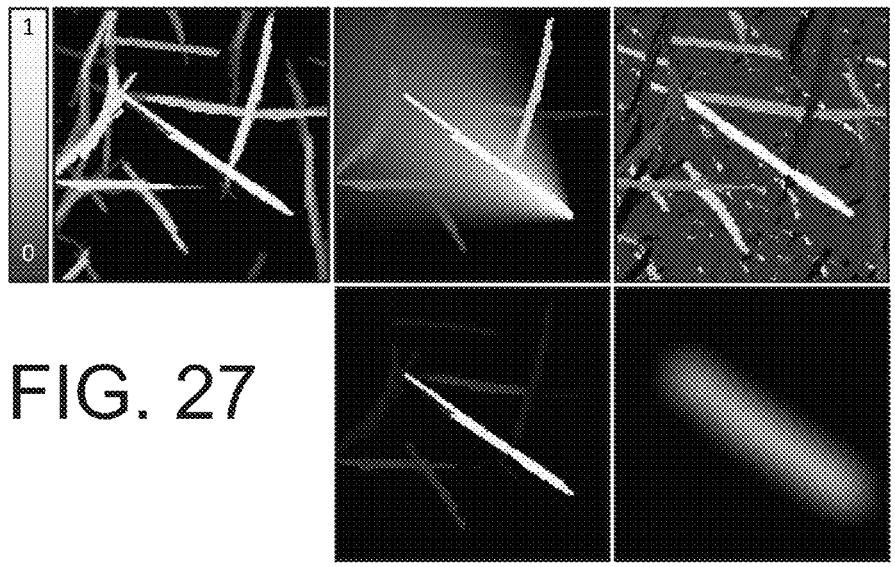
FIG. 27 is a screen shot of an x-ray image of an effecter in a surgical site illustrating one step of the detection method in the flow chart of FIG. 21.

The tracking information is then used to isolate the region of interest. The tracking information is used to weight the regions according to their proximity to the tool tip. This will generate a mask that can be used to selectively weight different parts of the image when the image is merged (FIG. 27). For each pixel, the mask value is the product of the region score, spatial proximity, and angle proximity. This value can be thresholded and scaled with an exponent to suppress irrelevant regions of the image. The edges of the regions are often jagged and do not exactly correspond to the tool. It is thus necessary to expand the region and smooth the boundaries so that the final merged image will not have any visually unpleasant discontinuities. This is accomplished with morphological dilation, followed by convolution with a Gaussian kernel. The values of the pixels in the mask are clamped to between 0 and 1. A value of 0 indicates that the pixel does not belong to the region of interest; a value of 1 indicates that the pixel fully belongs to the region of interest.

Figure 28:
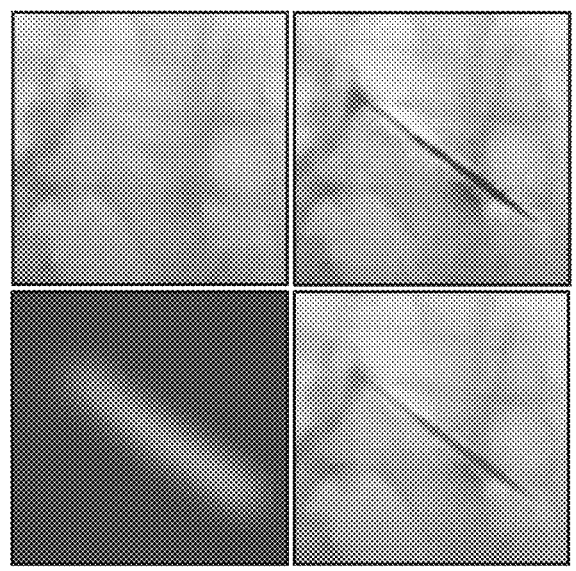
FIG. 28 is a screen shot of an x-ray image of a surgical site in which the effecter has been detected and the metal mask of the effecter enhanced within the image.

In the next step, the entire tool image is enhanced. The intensity offset image is added to the original image of the tool. The resulting sum may now have pixels outside the acceptable intensity range of 0 to 255. To bring the intensities back to an acceptable range, and to further improve the contrast around the metal edges, the histogram of the intensities within the mask region of the image sum is constructed in order to determine low and high quantiles. All intensities in the sum are scaled linearly so that the low quantile is now 0 and the high quantile is now 255. This yields an enhanced tool image. Finally, the enhanced tool image is added to the anatomical image. At pixels where the mask value is high, the enhanced tool image predominates, while at pixels where the mask value is low, the anatomical image predominates. The maximum and minimum ratios of the two images are chosen so that neither image is ever completely suppressed. This final merged image is displayed to the user as depicted in the screen shot of FIG. 28.

In one aspect of the present invention, the effecter tracking feature described above is used in connection with a system and method for providing updated images of the surgical field and patient anatomy without the requirement for full dose imaging. The image processing device 122 is thus further configured to provide high quality real-time images on the displays 123, 124 that are derived from lower detail images obtained using lower doses (LD) of radiation. By way of example, FIG. 29A is a "full dose" (FD) x-ray image, while FIG. 29B is a low dose and/or pulsed (LD) image of the same anatomy. It is apparent that the LD image is too "noisy" and does not provide enough information about the local anatomy for accurate image guided surgery. While the FD image provides a crisp view of the surgical site, the higher radiation dose makes taking multiple FD images during a procedure highly problematic. Using the steps described herein, the surgeon is provided with a current image shown in FIG. 29C that significantly reduces the noise of the LD image, in some cases by about 90%, so that surgeon is provided with a clear real-time image using a pulsed or low dose radiation setting. This capability allows for dramatically less radiation exposure during the imaging to verify the position of instruments and implants during the procedure.

Figure 30:
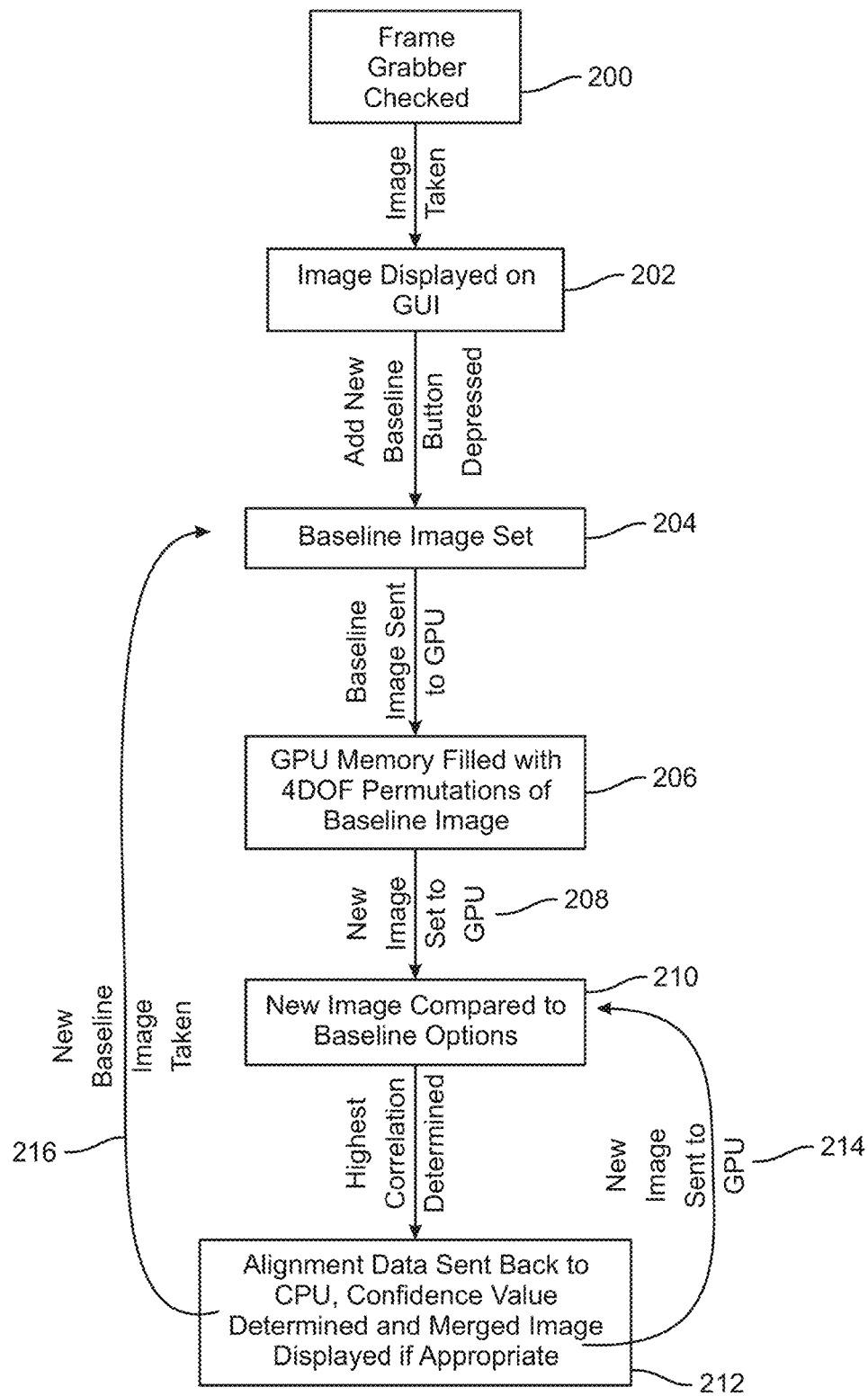
FIG. 30 is a flowchart of graphics processing steps undertaken by the image processing device shown in FIG. 1.

The flowchart of FIG. 30 illustrates steps of the method for generating the current image shown in FIG. 29C. In a first step 200, a baseline high resolution FD image is acquired of the surgical site and stored in a memory associated with the image processing device. In some cases where the C-arm is moved during the procedure, multiple high resolution images can be obtained at different locations in the surgical site, and then these multiple images "stitched" together to form a composite base image using known image stitching techniques). Movement of the C-arm, and more particularly "tracking" the acquired image during these movements, is accounted for in other steps described in more detail herein. For the present discussion it is assumed that the imaging system is relatively fixed, meaning that only very limited movement of the C-arm and/or patient are contemplated, such as might arise in an epidural pain procedure, spinal K-wire placement or stone extraction. The baseline image is projected in step 202 on the display 123 for verification that the surgical site is properly centered within the image. In some cases, new FD images may be obtained until a suitable baseline image is obtained. In procedures in which the C-arm is moved, new baseline images are obtained at the new location of the imaging device, as discussed below. If the displayed image is acceptable as a baseline image, a button may be depressed on a user interface, such as on the display device 126 or interface 125. In procedures performed on anatomical regions where a substantial amount of motion due to physiological processes (such as respiration) is expected, multiple baseline images may be acquired for the same region over multiple phases of the cycle. These images may be tagged to temporal data from other medical instruments, such as an ECG or pulse oximeter.

Once the baseline image is acquired, a baseline image set is generated in step 204 in which the original baseline image is digitally rotated, translated and resized to create thousands of permutations of the original baseline image. For instance, a typical two dimensional (2D) image of 128×128 pixels may be translated ±15 pixels in the x and y directions at 1 pixel intervals, rotated ±9° at 3° intervals and scaled from 92.5% to 107.5% at 2.5% intervals (4 degrees of freedom, 4D), yielding 47,089 images in the baseline image set. (A three-dimensional (3D) image will imply a 6D solution space due to the addition of two additional rotations orthogonal to the x and y axis. An original CT image data set can be used to form many thousands of DRRs in a similar fashion.) Thus, in this step, the original baseline image spawns thousands of new image representations as if the original baseline image was acquired at each of the different movement permutations. This "solution space" may be stored in a graphics card memory, such as in the graphics processing unit (GPU) of the image processing device 122, in step 206 or formed as a new image which is then sent to the GPU, depending on the number of images in the solution space and the speed at which the GPU can produce those images. With current computing power, on a free standing, medical grade computer, the generation of a baseline image set having nearly 850,000 images can occur in less than one second in a GPU because the multiple processors of the GPU can each simultaneously process an image.

During the procedure, a new LD image is acquired in step 208, stored in the memory associated with the image processing device, and projected on display 123. Since the new image is obtained at a lower dose of radiation it is very noisy. The present invention thus provides steps for "merging" the new image with an image from the baseline image set to produce a clearer image on the second display 124 that conveys more useful information to the surgeon. The invention thus contemplates an image recognition or registration step 210 in which the new image is compared to the images in the baseline image set to find a statistically meaningful match. A new "merged" image is generated in step 212 that may be displayed on display 124 adjacent the view of the original new image. At various times throughout the procedure, a new baseline image may be obtained in step 216 that is used to generate a new baseline image set in step 204.

Step 210 contemplates comparing the current new image to the images in the baseline image set. Since this step occurs during the surgical procedure, time and accuracy are critical. Preferably, the step can obtain an image registration in less than one second so that there is no meaningful delay between when the image is taken by the C-arm and when the merged image is displayed on the device 126. Various algorithms may be employed that may be dependent on various factors, such as the number of images in the baseline image set, the size and speed of the computer processor or graphics processor performing the algorithm calculations, the time allotted to perform the computations, and the size of the images being compared (e.g., 128×128 pixels, 1024× 1024 pixels, etc). In one approach, comparisons are made between pixels at predetermined locations described above in a grid pattern throughout 4D space. In another heuristic approach, pixel comparisons can be concentrated in regions of the images believed to provide a greater likelihood of a relevant match. In yet another approach, a principal component analysis (PCA) is performed, which can allow for comparison to a larger number of larger images in the allotted amount of time than is permitted with the full resolution grid approach. Further details of these approaches are disclosed in U.S. Pat. No. 8,526,700, incorporated by reference above.

In the image guided surgical procedures, tools, implants and instruments will inevitably appear in the image field. These objects are typically radiodense and consequently block the relevant patient anatomy from view. The new image obtained in step 210 will thus include an artifact of the tool T that will not correlate to any of the baseline image set. The image registration steps may be modified to account for the tool artifacts on the new image. In one approach, the new image may be evaluated to determine the number of image pixels that are "blocked" by the tool. In another approach, the image recognition or registration step 210 may include steps to measure the similarity of the LD image to a transformed version of the baseline image (i.e., a baseline image that has been transformed to account for movement of the C-arm, as described below relative to FIG. 34) or of the patient. Further details of these approaches are disclosed in U.S. Pat. No. 8,526,700, incorporated by reference above.

As previously explained, non-anatomical features may be present in the image, such as radio-dense effecters in the form of tool, instruments or implants. The effecters may be tracked according to the processes described above. During a surgical procedure it is still desirable to display an image of the entire surgical site, including of anatomy that is blocked by the radio-dense effecter. Thus, in a further aspect of the image manipulation steps, a mask image can be generated that identifies whether or not a pixel is part of an anatomical feature. Once the non-anatomical features are obtained, the baseline image of the anatomy obscured by the non-anatomical features can be merged into the image to show the surgical site without the radio-dense effecter.

In one aspect, an anatomical pixel may be assigned a value of 1 while a non-anatomical pixel is assigned a value of 0. This assignment of values allows both the baseline image and the LD image to be multiplied by the corresponding mask images before the similarity function is computed as described above In other words, the mask image can eliminate the non-anatomical pixels to avoid any impact on the similarity function calculations. To determine whether or not a pixel is anatomical, a variety of functions can be calculated in the neighborhood around each pixel. These functions of the neighborhood may include the standard deviation, the magnitude of the gradient, and/or the corresponding values of the pixel in the original grayscale image and in the filtered image. The "neighborhood" around a pixel includes a pre-determined number of adjacent pixels, such as a 5×5 or a 3×3 grid. Additionally, these functions can be compounded, for example, by finding the standard deviation of the neighborhood of the standard deviations, or by computing a quadratic function of the standard deviation and the magnitude of the gradient. One example of a suitable function of the neighborhood is the use of edge detection techniques to distinguish between bone and radio-dense instruments. Metal presents a "sharper" edge than bone and this difference can be determined using standard deviation or gradient calculations in the neighborhood of an "edge" pixel. The neighborhood functions may thus determine whether a pixel is anatomic or non-anatomic based on this edge detection approach and assign a value of 1 or 0 as appropriate to the pixel.

Once a set of values has been computed for the particular pixel, the values can be compared against thresholds determined from measurements of previously-acquired images and a binary value can be assigned to the pixel based on the number of thresholds that are exceeded. Alternatively, a fractional value between 0 and 1 may be assigned to the pixel, reflecting a degree of certainty about the identity of the pixel as part of an anatomic or non-anatomic feature. These steps can be accelerated with a GPU by assigning the computations at one pixel in the image to one processor on the GPU, thereby enabling values for multiple pixels to be computed simultaneously. The masks can be manipulated to fill in and expand regions that correspond to non-anatomical features using combinations of morphological image operations such as erosion and dilation.

Figure 31A:
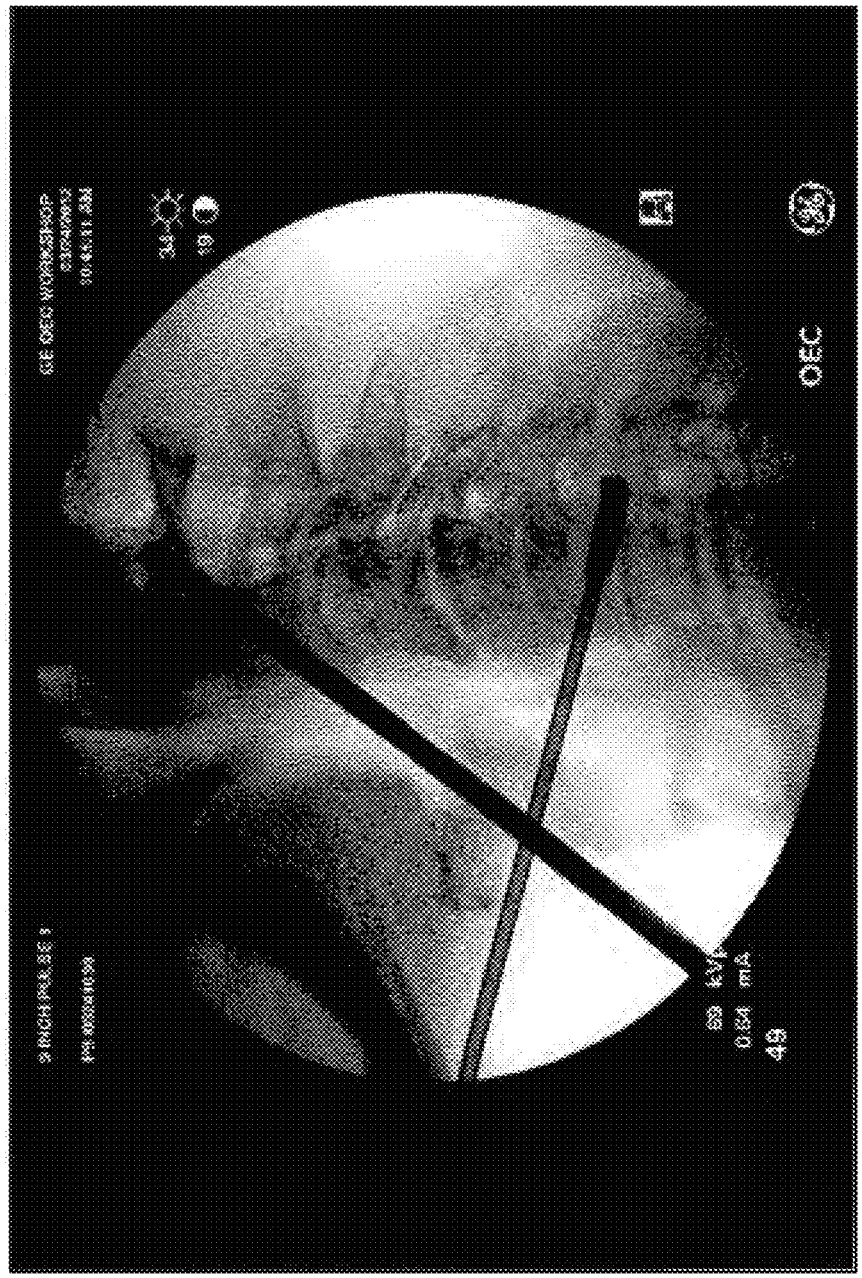
FIG. 31A is an image of a surgical field including an object blocking a portion of the anatomy.
Figure 31B:
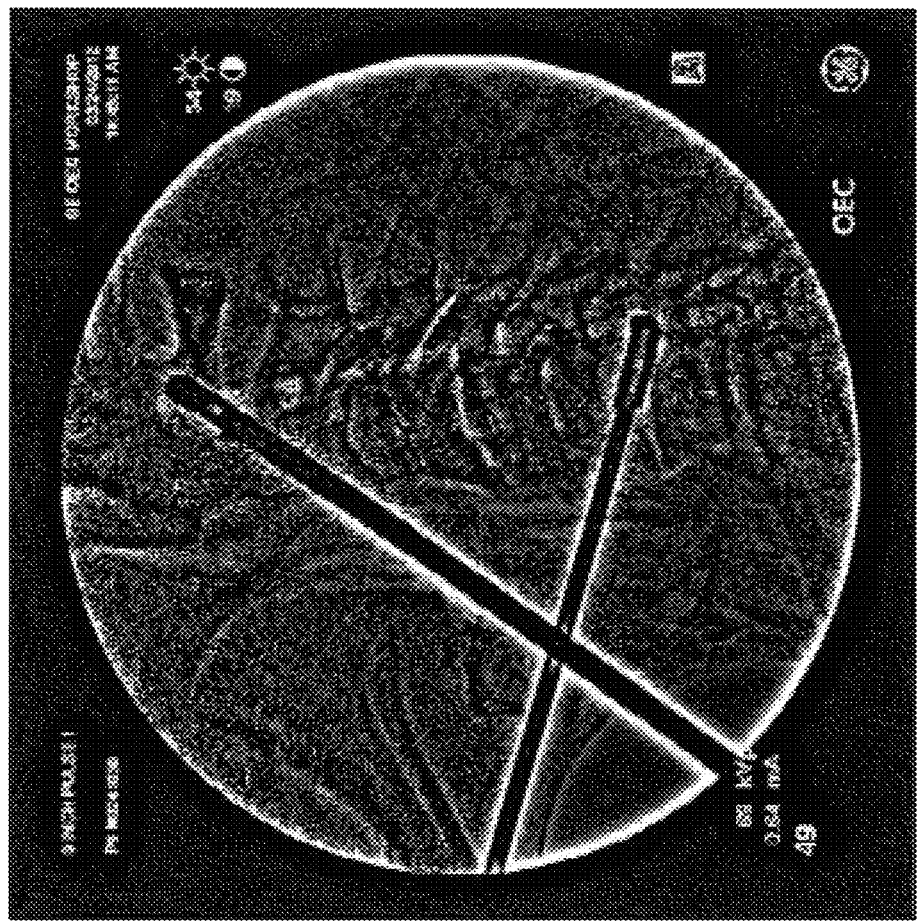
FIG. 31B is an image of the surgical field shown in FIG. 31A with edge enhancement.
Figure 31C:
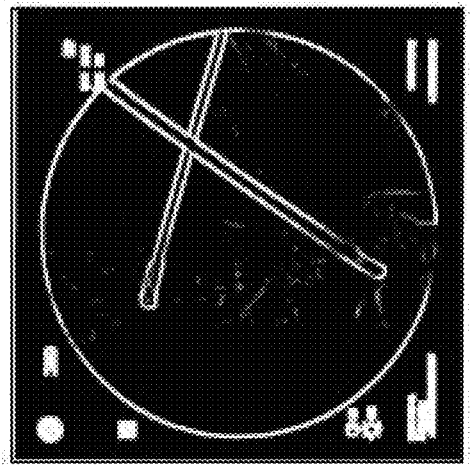
FIGS. 31C-31J are images showing the surgical field of FIG. 31B with different functions applied to determine the anatomic and non-anatomic features in the view.
Figure 31D:
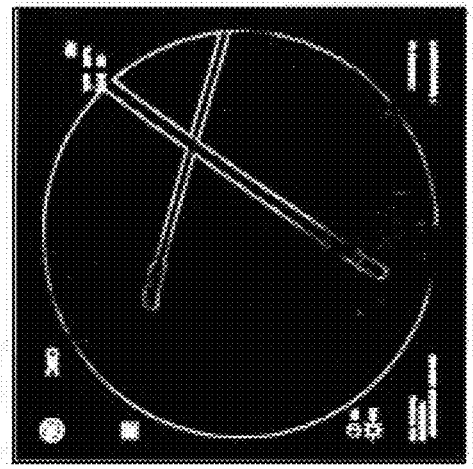
Figure 31E:
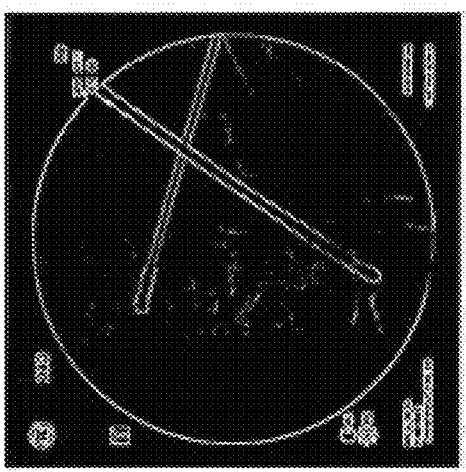
Figure 31F:
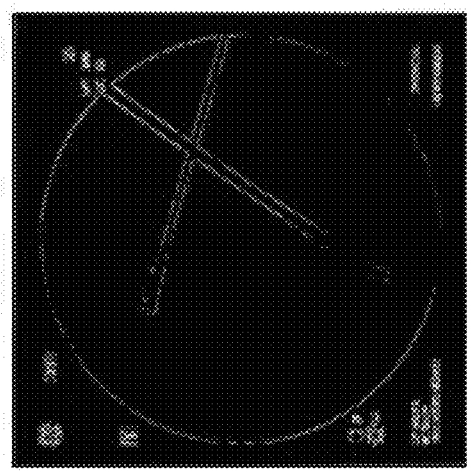
Figure 31G:
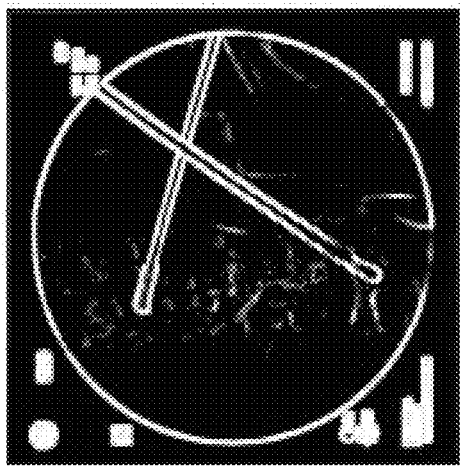
Figure 31H:
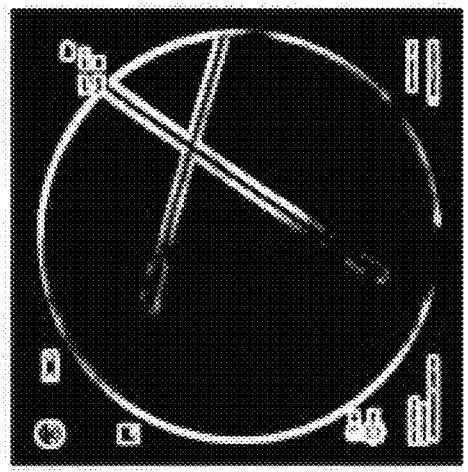
Figure 31I:
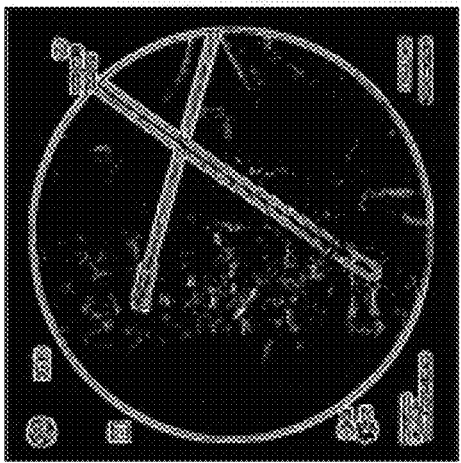
Figure 31J:
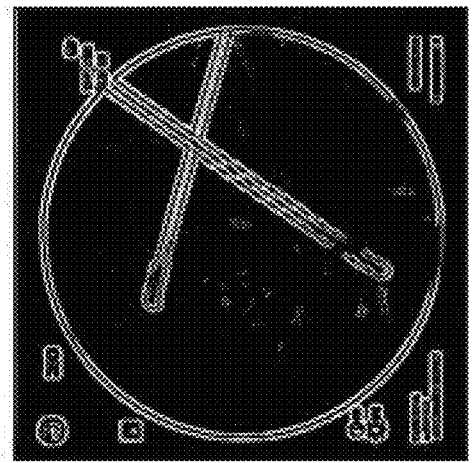
Figure 31L:
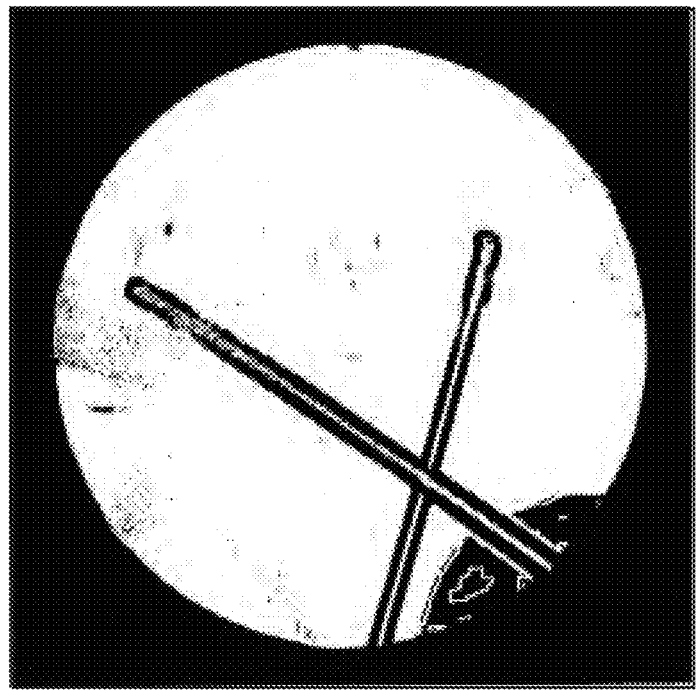
FIGS. 31K-31L are images of a mask generated using a threshold and a table lookup.
Figure 31K:
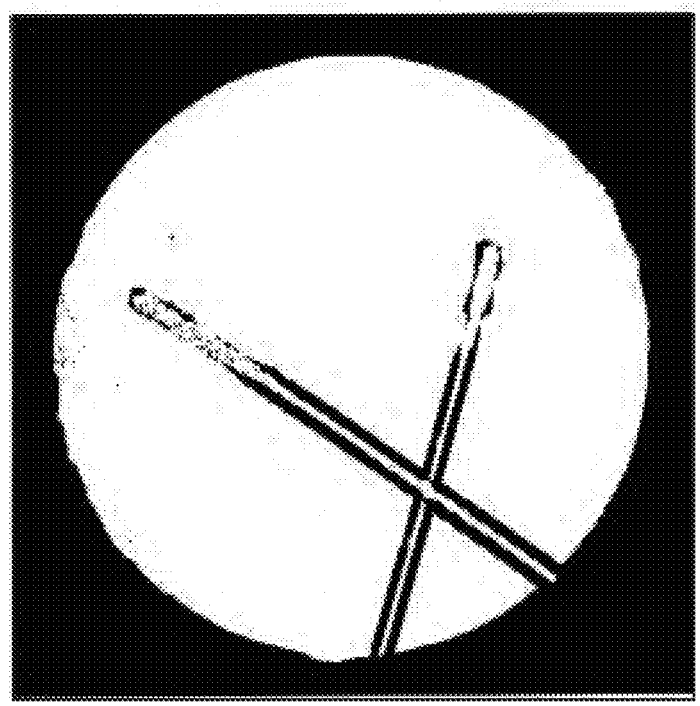
Figure 31N:
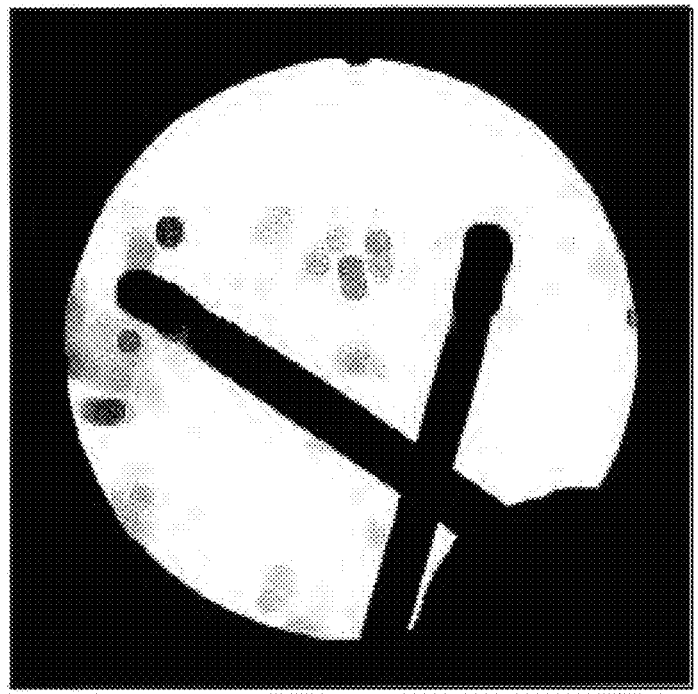
FIGS. 31M-31N are images of the masks shown in FIGS. 31K-31L respectively, after dilation and erosion.
Figure 31M:
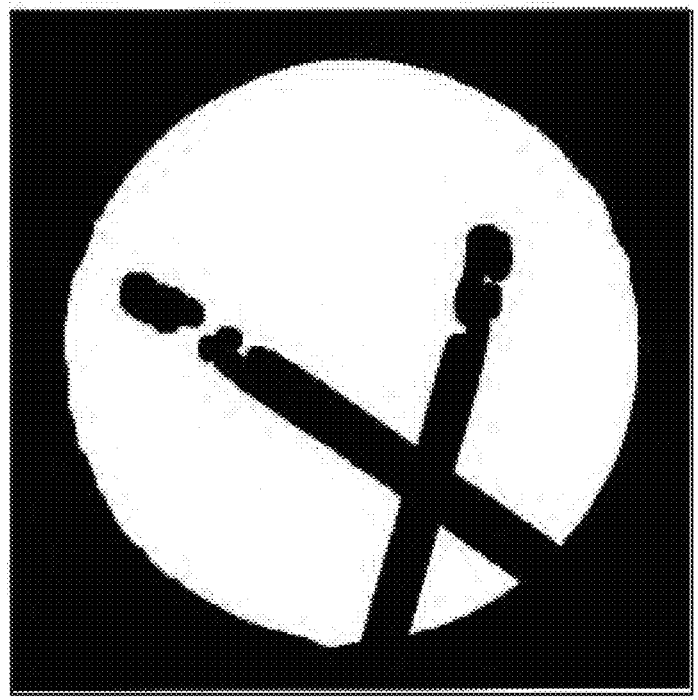
Figure 31P:
FIGS. 31O-31P are images prepared by applying the masks of FIGS. 31M-31N, respectively, to the filter image of FIG. 31B to eliminate the non-anatomic features from the image.

An example of the steps of this approach is illustrated in the images of FIGS. 31A-31P. In FIG. 31A, an image of a surgical site includes anatomic features (the patient's spine) and non-anatomic features (such as a clamp). The image of FIG. 31A is filtered for edge enhancement to produce the filtered image of FIG. 31B. It can be appreciated that this image is represented by thousands of pixels in a conventional manner, with the intensity value of each pixel modified according to the edge enhancement attributes of the filter. In this example, the filter is a Butterworth filter. This filtered image is then subject to eight different techniques for generating a mask corresponding to the non-anatomic features. Thus, the neighborhood functions described in U.S. Pat. No. 8,526,700 (namely, standard deviation, gradient and compounded functions thereof) are applied to the filtered image FIG. 31B to produce different images FIGS. 31C-31J. Each of these images is stored as a baseline image for comparison to and registration with a live LD image.

Figure 31O:

Each of the images of FIGS. 31C-31J is used to generate a mask. The mask generation process may be by comparison of the pixel intensities to a threshold value or by a lookup table in which intensity values corresponding to known non-anatomic features is compared to the pixel intensity. The masks generated by the threshold and lookup table techniques for one of the neighborhood function images is shown in FIGS. 31K-31L. The masks can then be manipulated to fill in and expand regions that correspond to the non-anatomical features, as represented in the images of FIGS. 31M-31N. The resulting mask is then applied to the filtered image of FIG. 31B to produce the "final" baseline images of FIGS. 31O-31P that will be compared to the live LD image. As explained above, each of these calculations and pixel evaluations can be performed in the individual processors of the GPU so that all of these images can be generated in an extremely short time. Moreover, each of these masked baseline images can be transformed to account for movement of the surgical field or imaging device and compared to the live LD image to find the baseline image that yields the highest Z score corresponding to the best alignment between baseline and LD images. This selected baseline image is then used in manner explained below.

Once the image registration is complete, the new image may be displayed with the selected image from the baseline image set in different ways. In one approach, the two images are merged, as illustrated in FIGS. 32A, B. The original new image is shown in FIG. 32A with the instrument T plainly visible and blocking the underlying anatomy. A partially merged image generated in step 212 (FIG. 30) is shown in FIG. 32B in which the instrument T is still visible but substantially mitigated and the underlying anatomy is visible. The two images may be merged by combining the digital representation of the images in a conventional manner, such as by adding or averaging pixel data for the two images. In one embodiment, the surgeon may identify one or more specific regions of interest in the displayed image, such as through the user interface 125, and the merging operation can be configured to utilize the baseline image data for the display outside the region of interest and conduct the merging operation for the display within the region of interest. The user interface 125 may be provided with a "slider" that controls the amount the baseline image versus the new image that is displayed in the merged image.

As described in U.S. Pat. No. 8,526,700, an image enhancement system can be used to minimize radio-opaque instruments and allow visualization of anatomy underlying the instrumentation. Alternatively, the system can be operable to enhance selected instrumentation in an image or collection of images. In particular, the masks describe above used to identify the location of the non-anatomic features can be selectively enhanced in an image. The same data can also be alternately manipulated to enhance the anatomic features and the selected instrumentation. This feature can be used to allow the surgeon to confirm that the visualized landscape looks as expected, to help identify possible distortions in the image, and to assist in image guided instrumentation procedures. Since the bone screw is radio-opaque it can be easily visualized under a very low dose x-ray a low dose new image can be used to identify the location of the instrumentation while merged with the high dose baseline anatomy image. Multiple very low dose images can be acquired as the bone screw is advanced into the bone to verify the proper positioning of the bone screw. Since the geometry of the instrument, such as the bone screw, is known (or can be obtained or derived such as from image guidance, 2-D projection or both), the pixel data used to represent the instrument in the x-ray image can be replaced with a CAD model mapped onto the edge enhanced image of the instrument.

As indicated above, the present invention also contemplates a surgical navigation procedure in which the imaging device or C-arm 103 is moved. The position of the C-arm can be tracked, rather than or in addition to tracking the position of the surgical instruments and implants, using commercially available tracking devices or the DICOM information from the imaging device. Tracking the C-arm requires a degree of accuracy that is much less than the accuracy required to track the instruments and implants. In this embodiment, the image processing device 122 receives tracking information from the tracking device 130. Tracking the position of the C-arm can account for "drift", which is a gradual misalignment of the physical space and the imaging (or virtual) space. This "drift" can occur because of subtle patient movements, inadvertent contact with the table or imaging device and even gravity. This misalignment is often visually imperceptible, but can generate noticeable shifts in the image viewed by the surgeon. These shifts can be problematic when the surgical navigation procedure is being performed (and a physician is relying on the information obtained from this device) or when alignment of new to baseline images is required to improve image clarity. The use of image processing eliminates the inevitable misalignment of baseline and new images. The image processing device 122 further may incorporate a calibration mode in which the current image of the anatomy is compared to the predicted image. The difference between the predicted and actual movement of the image can be accounted for by an inaccurate knowledge of the "center of mass" or COM, described below, and drift. Once a few images are obtained and the COM is accurately established, recalibration of the system can occur automatically with each successive image taken and thereby eliminating the impact of drift.

A display with two view finder images can be utilized by the radiology technician to orient the C-arm to acquire a new image at the same orientation as a baseline image. In this embodiment, the two view finder images are orthogonal images, such as an anterior-posterior (AP) image (passing through the body from front to back) and a lateral (LAT) image (passing through the body shoulder to shoulder). The technician seeks to align both view finder images to corresponding AP and LAT baseline images. As the C-arm is moved by the technician, both images are tracked simultaneously, similar to the single view finder described above. It can be appreciated that the two view navigation images may be derived from a baseline image and a single shot or X-ray image at a current position, such as a single AP image. As the view finder for the AP image is moved to position the view at a desired location, the second view finder image displays the projection of that image in the orthogonal plane (i.e., the lateral view). The physician and x-ray technician can thus maneuver the C-arm to the desired location for a lateral view based on the projection of the original AP view. Once the C-arm is aligned with the desired location, the C-arm can then actually be positioned to obtain the orthogonal (i.e., lateral) x-ray image.

The present invention can also be used with a feature that enhances the communication between the surgeon and the radiology technician. During the course of a procedure the surgeon may request images at particular locations or orientations. One example is what is known as a "Ferguson view" in spinal procedures in which an AP oriented C-arm is canted to align directly over a vertebral end plate with the end plate oriented "flat" or essentially parallel with the beam axis of the C-arm. Obtaining a Ferguson view requires rotating the C-arm or the patient table while obtaining multiple AP views of the spine, which is cumbersome and inaccurate using current techniques, requiring a number of fluoroscopic images to be performed to find the one best aligned to the endplate. The present invention allows the surgeon to overlay a grid onto a single image or stitched image and provide labels for anatomic features that can then be used by the technician to orient the C-arm. Thus, as shown in FIG. 33A, the image processing device 122 is configured to allow the surgeon to place a grid 245 within the tracking circle 240 overlaid onto a Lateral image. The surgeon may also locate labels 250 identifying anatomic structure, in this case spinal vertebrae. In this particular example, the goal is to align the L2-L3 disc space with the center grid line 246. To assist the technician, a trajectory arrow 255 is overlaid onto the image to indicate the trajectory of an image acquired with the C-arm in the current position. As the C-arm moves, changing orientation off of pure AP, the image processing device evaluates the C-arm position data obtained from the tracking device 230 to determine the new orientation for trajectory arrow 255. The trajectory arrow thus moves with the C-arm so that when it is aligned with the center grid line 246, as shown in FIG. 33B, the technician can shoot the image knowing that the C-arm is properly aligned to obtain a Ferguson view along the L3 endplate. Thus, monitoring the lateral view until it is rotated and centered along the center grid line allows the radiology technician to find the AP Ferguson angle without guessing and taking a number of incorrect images.

Figure 34:
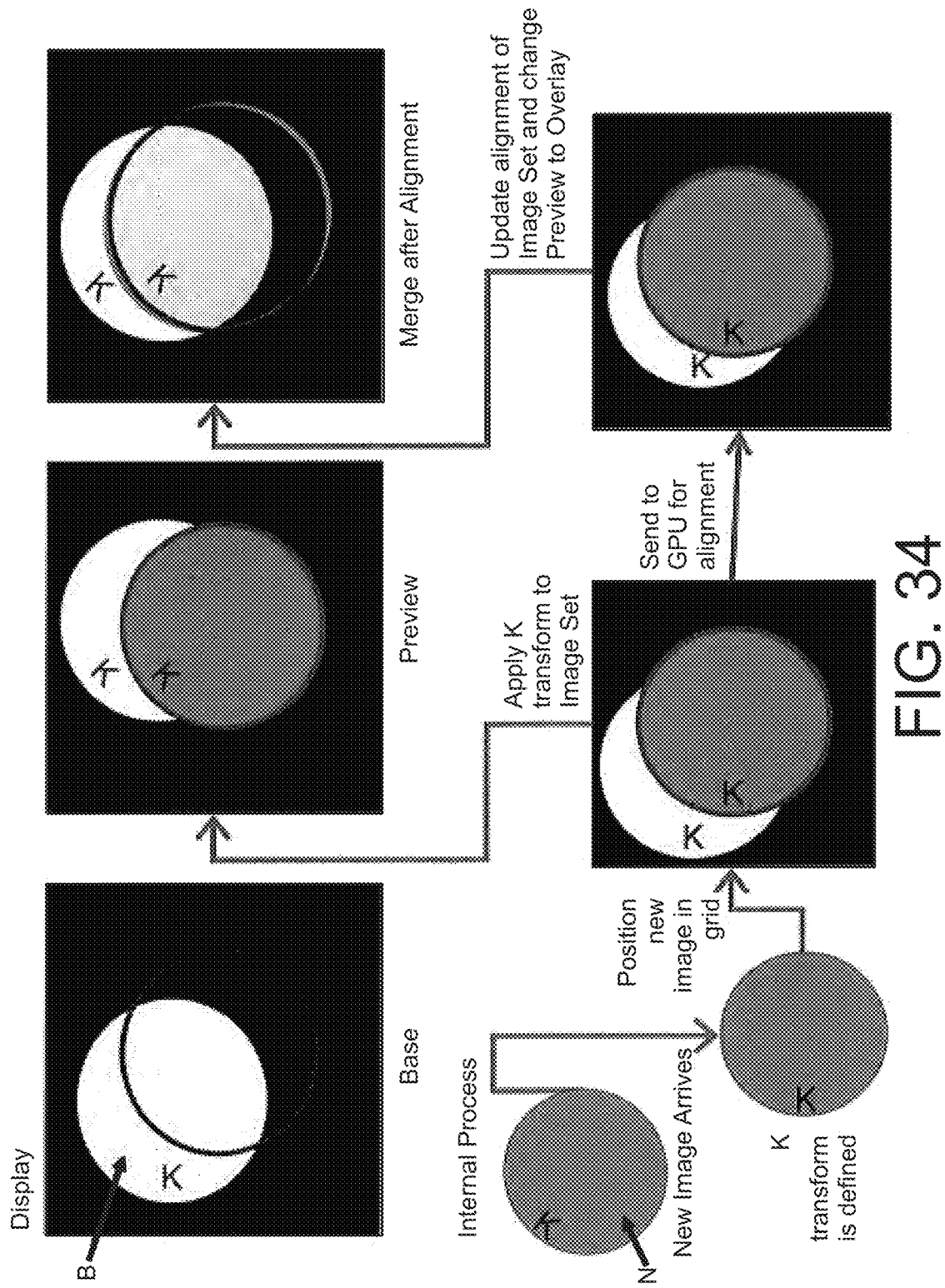
FIG. 34 is a graphical representation of an image alignment process according to the present disclosure.

In another feature, a radiodense asymmetric shape or glyph can be placed in a known location on the C-arm detector. This creates the ability to link the coordinate frame of the C-arm to the arbitrary orientation of the C-arm's image coordinate frame. As the C-arm's display may be modified to generate an image having any rotation or mirroring, detecting this shape radically simplifies the process of image comparison and image stitching. Thus, as shown in FIG. 34, the baseline image B includes the indicia or glyph "K" at the 9 o'clock position of the image. In an alternative embodiment, the glyph may be in the form of an array of radio-opaque beads embedded in a radio-transparent component mounted to a C-arm collar, such as in a right triangular pattern. Since the physical orientation and location of the glyph relative to the C-arm is fixed, knowing the location and orientation of the glyph in a 2D image provides an automatic indication of the orientation of the image with respect to the physical world. The new image N is obtained in which the glyph has been rotated by the physician or technologist away from the default orientation. Comparing this new image to the baseline image set is unlikely to produce any registration between images due to this angular offset. In one embodiment, the image processing device detects the actual rotation of the C-arm from the baseline orientation while in another embodiment the image processing device uses image recognition software to locate the "K" glyph in the new image and determine the angular offset from the default position. This angular offset is used to alter the rotation and/or mirror image the baseline image set. The baseline image selected in the image registration step 210 is maintained in its transformed orientation to be merged with the newly acquired image. This transformation can include rotation and mirror-imaging, to eliminate the display effect that is present on a C-arm. The rotation and mirroring can be easily verified by the orientation of the glyph in the image. It is contemplated that the glyph, whether the "K" or the radio-opaque bead array, provides the physician with the ability to control the way that the image is displayed for navigation independent of the way that the image appears on the X-ray screen used by the technician. In other words, the imaging and navigation system disclosed herein allows the physician to rotate, mirror or otherwise manipulate the displayed image in a manner that physician wants to see while performing the procedure. The glyph provides a clear indication of the manner in which the image used by the physician has been manipulated in relation to the X-ray image. Once the physician's desired orientation of the displayed image has been set, the ensuing images retain that same orientation regardless of how the C-arm has been moved.

The image processing device configured as described herein provides three general features that: (1) reduce the amount of radiation exposure required for acceptable live images, (2) provide images to the surgeon that can facilitate the surgical procedure, and (3) improve the communication between the radiology technician and the surgeon. With respect to the aspect of reducing the radiation exposure, the present invention permits low dose images to be taken throughout the surgical procedure to verify the position of an effecter, such as tool, instrument or implant, and/or to account for movements of the C-arm. The systems and methods herein fill in the gaps created by "noise" in the current image to produce a composite or merged image of the current field of view with the detail of a full dose image. In practice this allows for highly usable, high quality images of the patient's anatomy generated with an order of magnitude reduction in radiation exposure than standard FD imaging using unmodified features present on all common, commercially available C-arms. The techniques for image registration described herein can be implemented in a graphic processing unit and can occur in a second or so to be truly interactive; when required such as in CINE mode, image registration can occur multiple times per second. A user interface allows the surgeon to determine the level of confidence required for acquiring registered image and gives the surgeon options on the nature of the display, ranging from side-by-side views to fade in/out merged views.

With respect to the feature of providing images to the surgeon that facilitate the surgical procedure, several digital imaging techniques can be used to improve the user's experience. One example is an image tracking feature that can be used to maintain the image displayed to the surgeon in an essentially a "stationary" position regardless of any position changes that may occur between image captures. In accordance with this feature, the baseline image can be fixed in space and new images adjust to it rather than the converse. When successive images are taken during a step in a procedure each new image can be stabilized relative to the prior images so that the particular object of interest (e.g.— anatomy or instrument) is kept stationary in successive views. For example, as sequential images are taken as a bone screw is introduced into a body part, the body part remains stationary on the display screen so that the actual progress of the screw can be directly observed.

In another aspect of this feature, the current image including blocking effecters can be compared to earlier images without any blocking effecters. In the registration process, the image processing device can generate a merged image between new image and baseline image that deemphasizes the blocking nature of the object from the displayed image. The user interface also provides the physician with the capability to fade the blocking object in and out of the displayed view.

In other embodiments in which the effecter itself is being tracked, the image processing device can obtain position data from a tracking device following the position of the blocking object and use that position data to either move a full image including the effecter or to determine the proper location and orientation of a virtual object in the displayed image. The virtual object may be applied to a baseline image to be compared with a new current image to serve as a check step—if the new image matches the generated image (both tool and anatomy) within a given tolerance then the surgery can proceed. If the match is poor, the surgery can be stopped (in the case of automated surgery) and/or recalibration can take place. This allows for a closed-loop feedback feature to facilitate the safety of automation of medical intervention.

In the third feature—improving communication—the image processing device described herein allows the surgeon to annotate an image in a manner that can help guide the technician in the positioning of the C-arm as to how and where to take a new picture or help the surgeon in guiding the effecter (tool, instrument or implant) to a desired location relative to the patient's anatomy. The user interface 125 of the image processing device 122 provides a vehicle for the surgeon to add a grid to the displayed image, label anatomic structures and/or identify trajectories for alignment of the imaging device.

The same system and techniques described above may be implemented where a collimator is used to reduce the field of exposure of the patient. For instance, as shown in FIG. 35A, a collimator may be used to limit the field of exposure to the area 300 which presumably contains the critical anatomy to be visualized by the surgeon or medical personnel. As is apparent from FIG. 35A the collimator prevents viewing the region 301 that is covered by the plates of the collimator. Using the system and methods described above, prior images of the area 315 outside the collimated area 300 are not visible to the surgeon in the expanded field of view 310 shown in FIG. 35B.

The present disclosure contemplates am image guide surgical system that reduces time and radiation dosage during a surgical procedure that uses a C-arm fluoroscope. The system disclosed herein augments the X-ray image of the patient's anatomy in order to visualize the predicted location of a surgical tool, and substantiates that position with tracking elements associated with the surgical tools and instruments as they enter the X-ray viewing field. Predicting the location of the instrument and its working end/tip requires a tracking system which determines and reports the spatial position of the tracked object with respect to the tracking device 130 (FIG. 1), and an accurate model of the geometry of the entire system.

Figure 65:
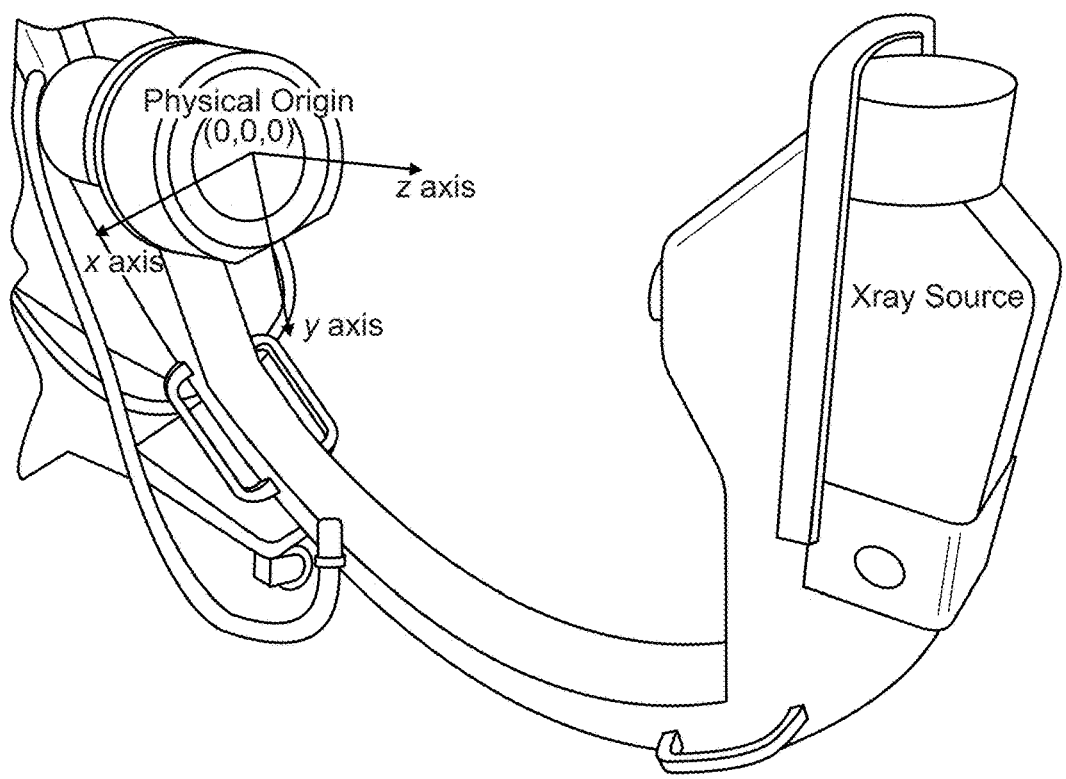
FIG. 65 is a perspective view of a conventional C-arm x-ray device showing the system coordinates superimposed thereon.
Figure 69:
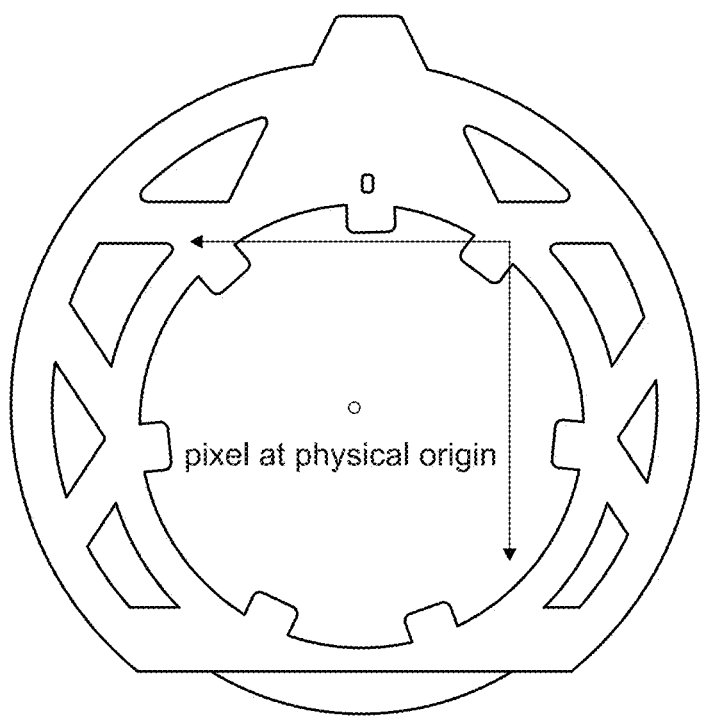
FIG. 69 is a bottom view of the calibration collar shown in FIG. 67 with the X-ray array coordinate system superimposed thereon.
Figure 70:
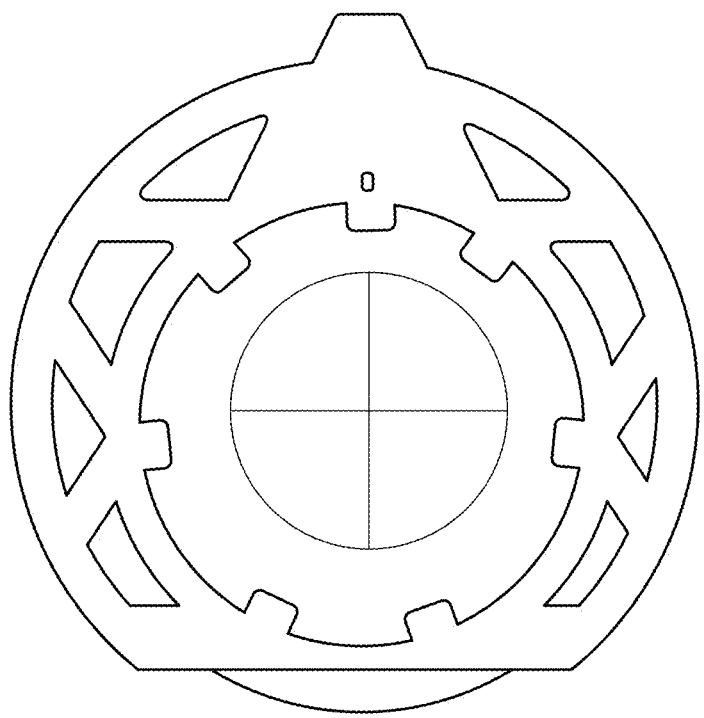
FIG. 70 is a bottom view of the calibration collar shown in FIG. 67 with an aspect ratio grid superimposed thereon.
Figure 71:
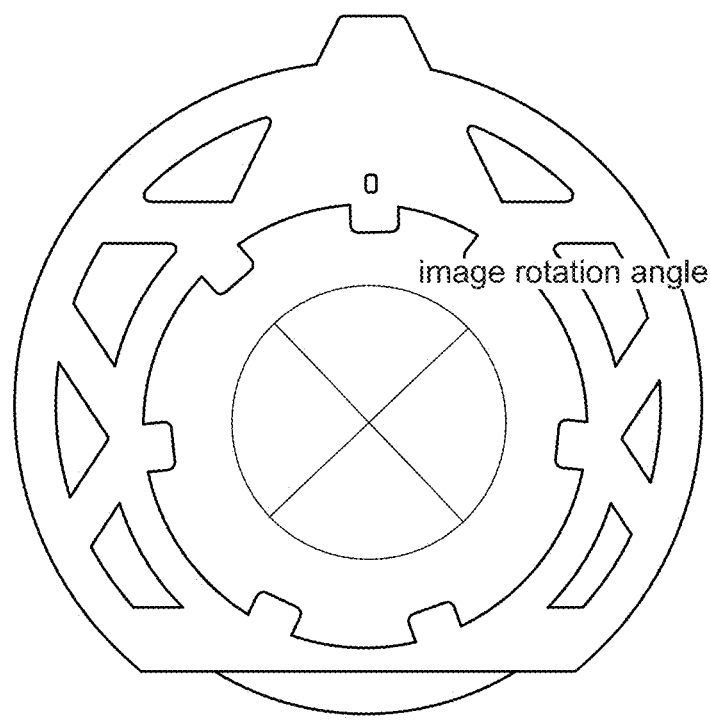
FIG. 71 is a bottom view of the calibration collar shown in FIG. 67 with an image rotation grid superimposed thereon.
Figure 72:
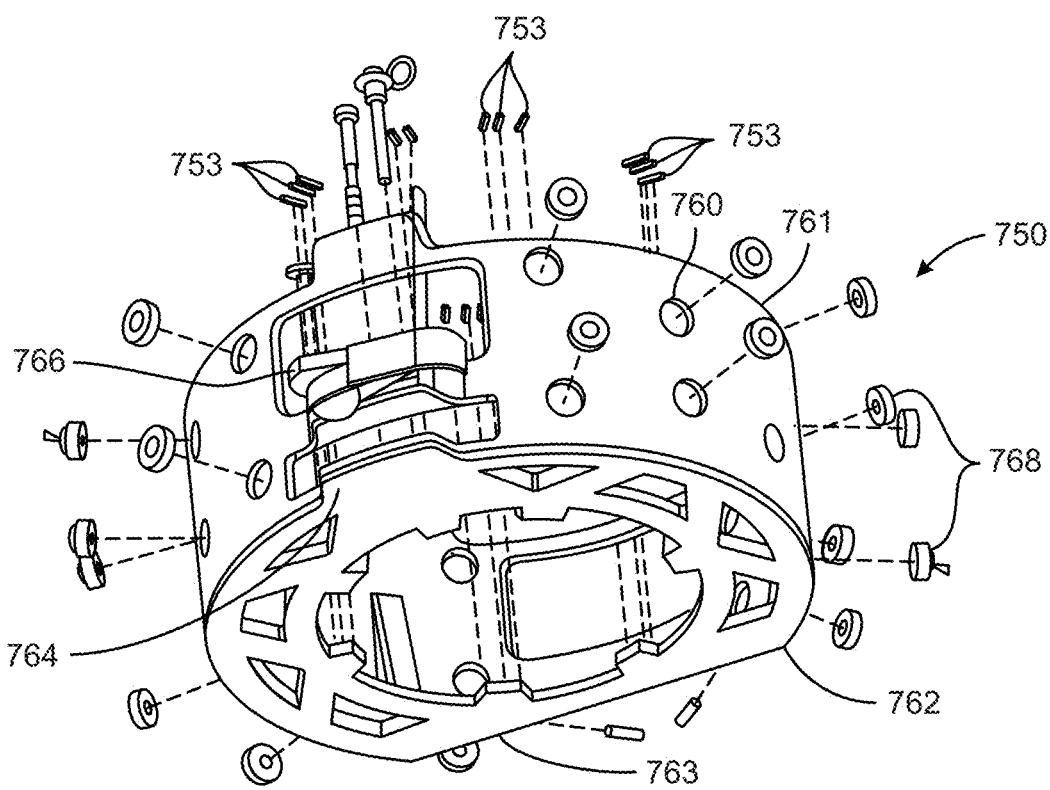
FIG. 72 is an exploded assembly view of the calibration collar shown in FIG. 67.
Figure 73:
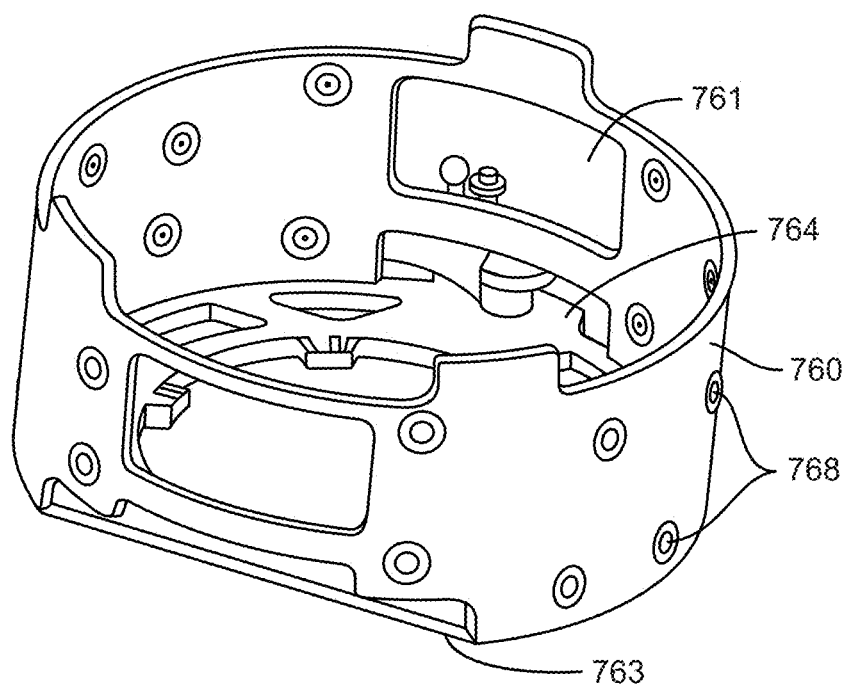
FIG. 73 is a perspective view of the calibration collar shown in FIG. 67.

A central component of the system geometry is the C-arm itself. As illustrated in FIG. 65, the C-arm includes an X-ray source that emits X-rays from a point source, which travel in straight line trajectories to a rectangular array of photoelectric sensors in the X-ray detector. The sensors transduce the X-rays into electrical signals which are recorded in a rectangular array of pixels. To predict the pixel coordinates to the tracked effector or tool it is essential to know the position in space of the point source, designated $x_s$, $y_s$, $z_s$ in FIG. 65, and each pixel of the detector. As reflected in FIG. 65, the center of the X-ray detector establishes the physical origin of the x, y and z axes. As shown in FIG. 69, the rectangular pattern of pixels defines u and v axes so that the physical origin (0,0,0) of the system corresponds to $u_0$, $v_0$ in the pixel coordinate system.

These coordinate systems provide the basis for mapping which pixels of a detected image correspond to the tracked surgical tool/instrument. In particular, Equation 1 below locates the pixel coordinates (u. v) in terms of the physical origin coordinate system, taking into account the spacing p between pixels, the aspect ratio r between the vertical pixel increment and the horizontal pixel increment, and the rotation angle α of the C-arm:

$$p\begin{bmatrix} r & 0 \\ 0 & 1 \end{bmatrix}\begin{bmatrix} \cos a & \sin a \\ -\sin a & \cos a \end{bmatrix}\begin{bmatrix} z_s\left(\frac{x-x_s}{z_s-z}\right)+x_s \\ z_s\left(\frac{y-y_s}{z_s-z}\right)+y_s \end{bmatrix} + \begin{bmatrix} u_0 \\ v_0 \end{bmatrix} = \begin{bmatrix} u \\ v \end{bmatrix} \quad (1)$$

This model can be augmented by considering that there may be distortion on the X-ray detector so that the pixels do not conform to a rectangular grid. This can be modeled by considering each pixel to have an angular offset $a_d$ and a radial offset $r_d$. The location of a pixel can then be modeled by Equations 2-4 below:

$$\begin{bmatrix} z_s\left(\frac{x-x_s}{z_s-z}\right)+x_s \\ z_s\left(\frac{y-y_s}{z_s-z}\right)+y_s \end{bmatrix} = \begin{bmatrix} x_d \\ y_d \end{bmatrix} \quad (2)$$

$$\sqrt{x_d^2 + y_d^2} = d \quad (3)$$

$$pe^{dr_d}\begin{bmatrix} r & 0 \\ 0 & 1 \end{bmatrix}\begin{bmatrix} \cos a & \sin a \\ -\sin a & \cos a \end{bmatrix}\begin{bmatrix} \cos da_d & \sin da_d \\ -\sin da_d & \cos da_d \end{bmatrix}\begin{bmatrix} x_d \\ y_d \end{bmatrix} + \begin{bmatrix} u_0 \\ v_0 \end{bmatrix} = \begin{bmatrix} u \\ v \end{bmatrix} \quad (4)$$

In an ideal case, the parameters of the model in Equations 1 or 4 can be inferred from the physical specifications of the C-arm. However, these parameters can vary between C-arms, between surgical procedures and even between images in the same surgical session as the C-arm bends under the influence of gravity. These perturbations can seriously impact the ability to accurately track the location of the working end/tip of a surgical instrument within the surgical site, particularly when a clear direct view of the instrument tip is not available. The present disclosure provides a method for calibrating the C-arm that can be implemented at any time before and during a surgical procedure. In particular, devices are provided that permit calibration of the X-ray source and the X-ray detector of the C-arm.

Figure 66:
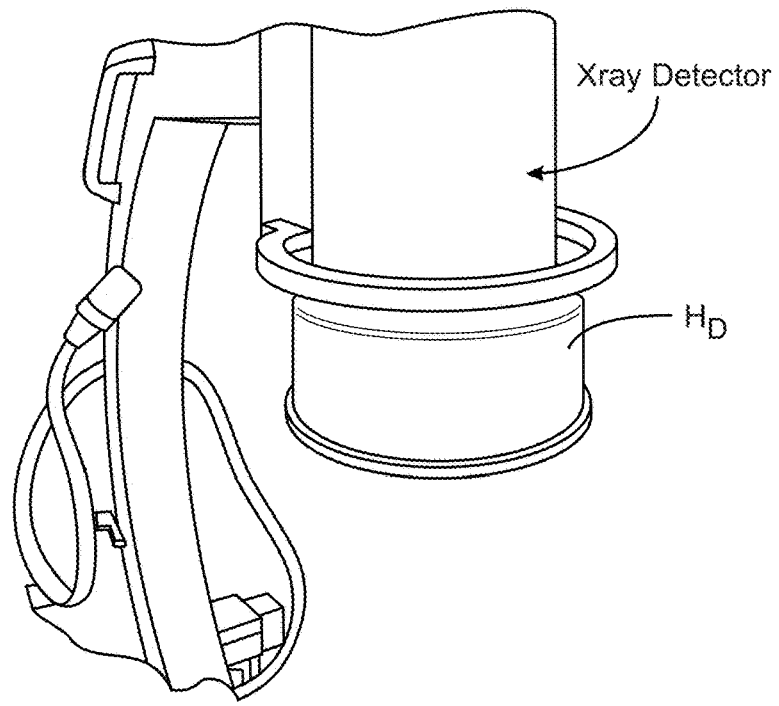
FIG. 66 is a perspective view of an X-ray detector of the C-arm device shown in FIG. 65.
Figure 67:
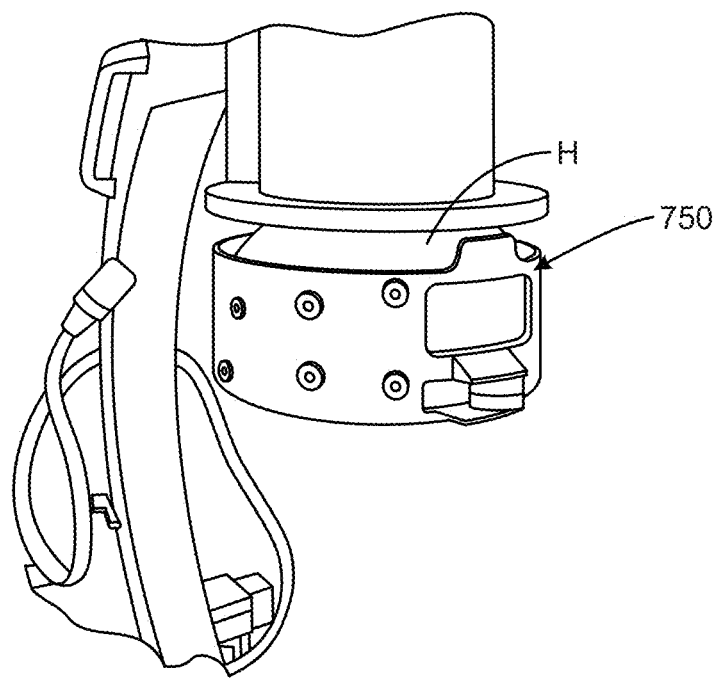
FIG. 67 is a perspective view of the X-ray detector shown in FIG. 66, with a calibration collar mounted thereto according to one aspect of the present disclosure.
Figure 68:
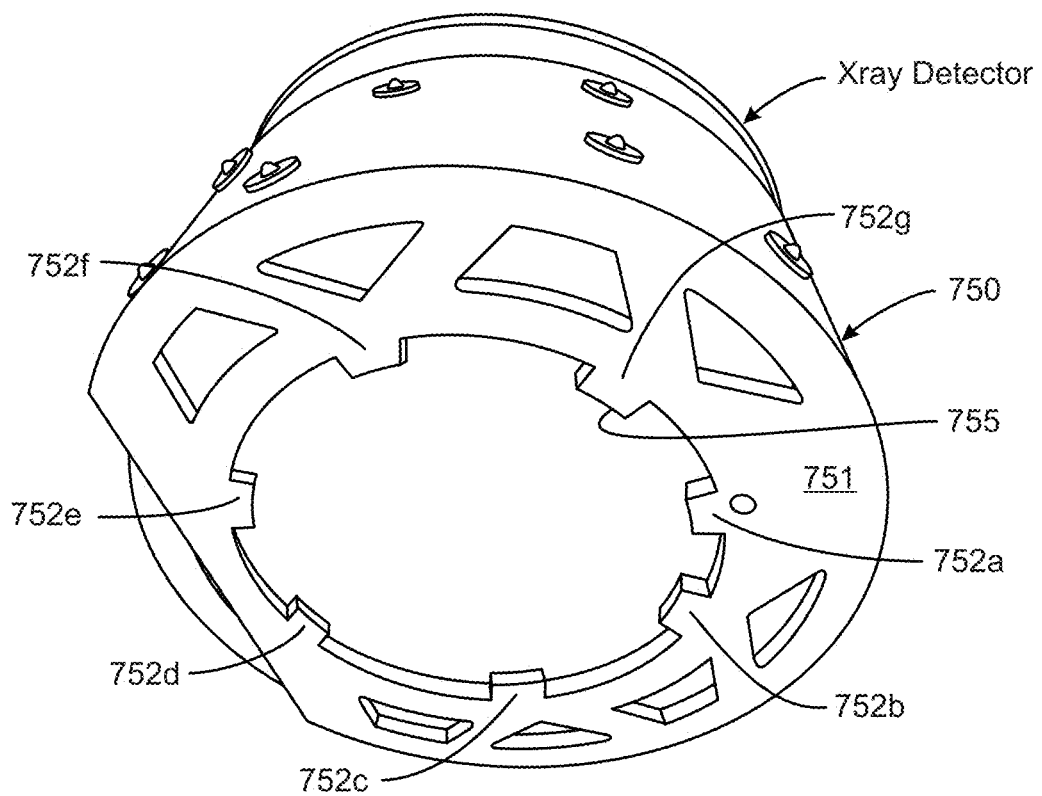
FIG. 68 is a bottom view of the calibration collar shown in FIG. 67.
Figure 74:
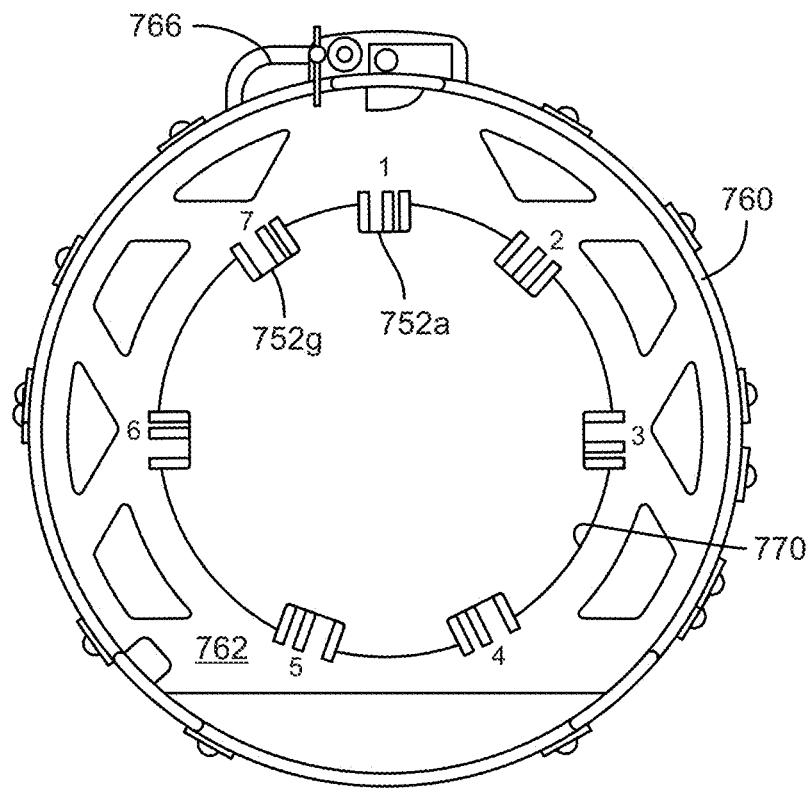
FIG. 74 is a bottom view of the calibration collar shown in FIG. 67.
Figure 75:
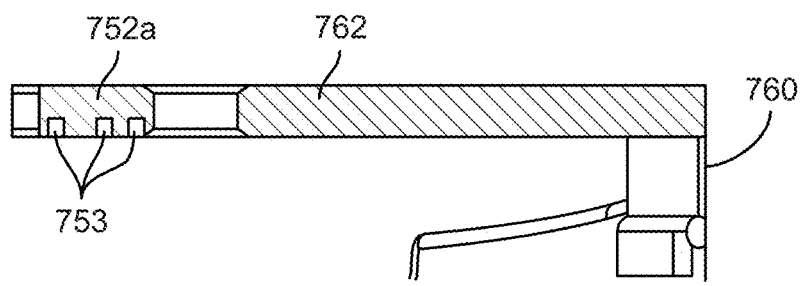
FIG. 75 is an enlarged cross-sectional view of a portion of the calibration collar shown in FIG. 74.

In one aspect of the disclosure, a calibration collar 750 is configured to be mounted on the detector housing $H_D$ of the C-arm (FIG. 66) with the end face 751 of the collar flat with the end face of the housing. The end face 751 includes a plurality of unique glyphs 752a-752g that allow the image processing software to determine the angular orientation of the x-ray detector. In the illustrated embodiment, seven such glyphs are provided, each with a unique radio-opaque pattern, as depicted in FIG. 74. In particular, each glyph includes three radial metallic bars 753 (FIG. 72) that are arranged in unique patterns with unique spacing between each of the three radial bars. The unique patterns thus allow the image processing software to determine the angular orientation of the collar 750 and thus the X-ray detector based on the angular deviation of the glyphs from the baseline orientation in which the first glyphs 752a is aligned along the system y-axis.

It can be noted that the when the objects being "tracked" are the glyphs the influence of the X-ray source in Equations 1-4 above is negligible because the glyphs are essentially at the same z-distance from the X-ray source as the rectangular pattern of pixels. Thus, the above equations reduce to Equation 5 for determining the angle α of the C-arm X-ray detector:

$$p \begin{bmatrix} r & 0 \\ 0 & 1 \end{bmatrix} \begin{bmatrix} \cos a & \sin a \\ -\sin a & \cos a \end{bmatrix} \begin{bmatrix} x \\ y \end{bmatrix} + \begin{bmatrix} u_0 \\ v_0 \end{bmatrix} = \begin{bmatrix} u \\ v \end{bmatrix} \quad (5)$$

Details of the calibration collar 750 are shown in FIGS. 72-75. The collar 750 includes a circumferential ring 760 that is open at one end 761 to be seated over the detector housing $H_D$, and closed at the opposite end by an end plate 762 that abuts the end face of the detector housing so that the end plate is as close to the detector elements as possible. The end plate 762 includes a flat edge 763 and an opposite tab 764 that help orient the collar 750 on the detector housing $H_D$. In particular, the collar is mounted on the housing with the flat edge 763 closest to the arm of the X-ray machine, and the tab 764 distal from the arm. The tab 764 is oriented along the system Y-axis. A latch mechanism 766 is configured to clamp the collar firmly to the detector housing.

The end plate 762 defines a central opening 770 at a diameter that matches the diameter of the detector array within the detector housing $H_D$. The glyphs 752a-g extend radially inward from the opening diameter so that the glyphs overlap the detector array. As shown in the cross-sectional view of FIG. 75, the metallic bars 753 are embedded within the end plate 762, either by over-molding the bars within the end plate when the plate is formed, or by mounting and adhering the bars within channels defined in the end plate. An array of Radix lens assemblies 768 can be positioned around the circumferential ring 760 for detection by the tracking device 130.

Figure 76:
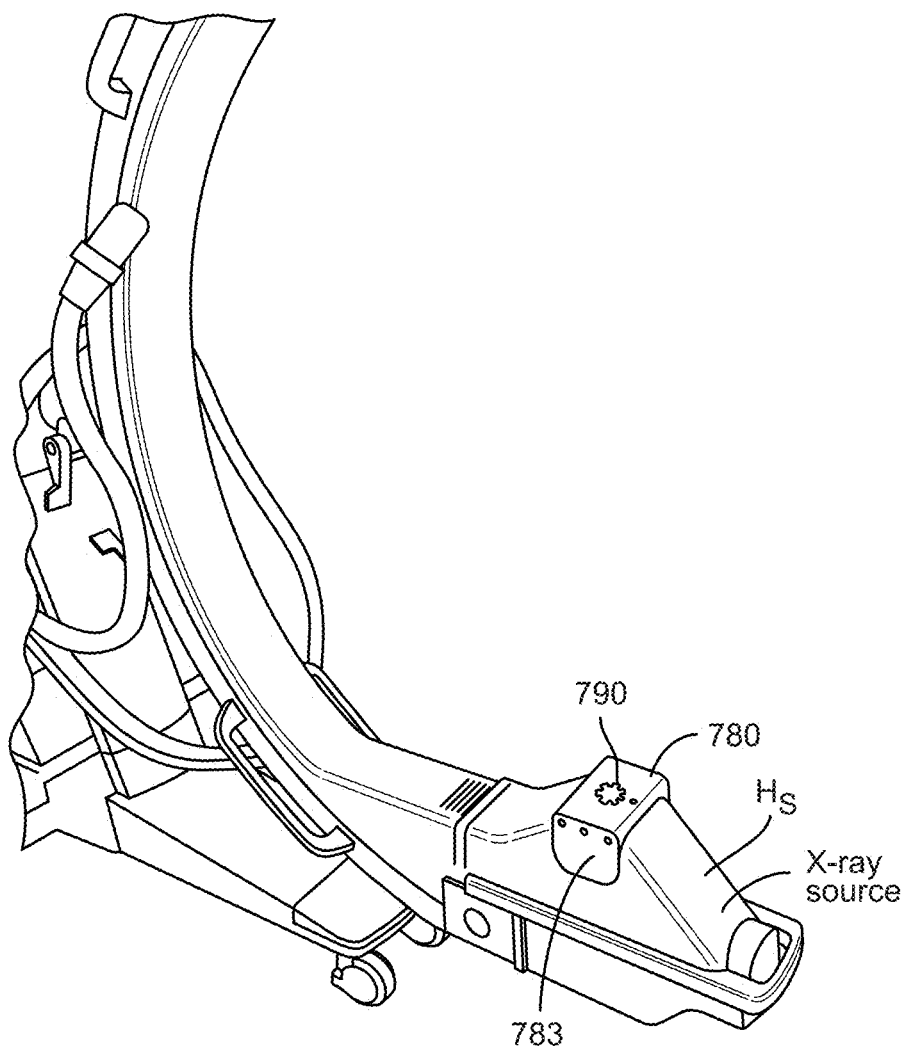
FIG. 76 is a perspective view of the X-ray source for the C-arm device shown in FIG. 65, shown with a source calibration device mounted thereto according to a further aspect of the present disclosure.
Figure 77:
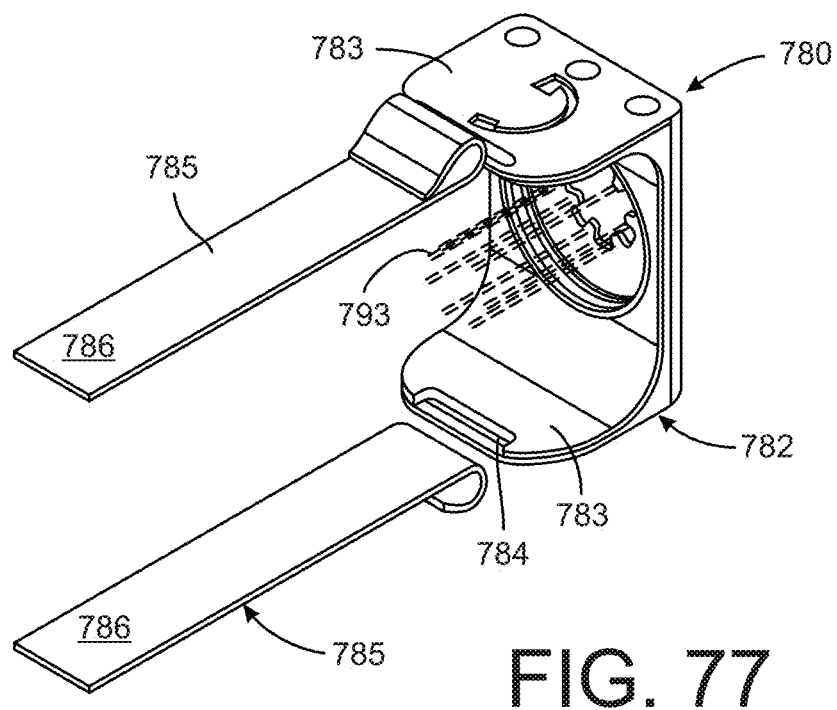
FIG. 77 is an exploded assembly view of a source calibration device according to one embodiment of the present disclosure.
Figure 79:
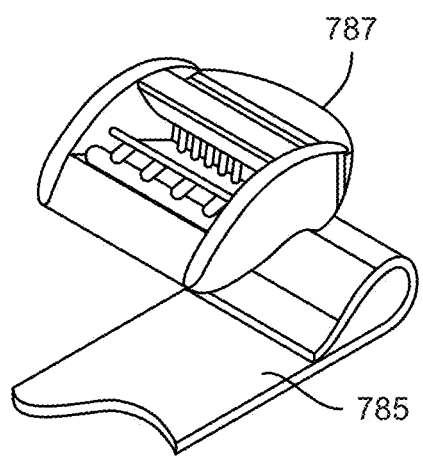
FIG. 79 is an enlarged view of a portion of the source calibration device shown in FIG. 77.

The C-arm calibration process can also involve calibration of the X-ray source, either separately from or together with calibration of the detector. To that end, the present disclosure provides a source cap 780 that is configured to be mounted over the housing $H_S$ as shown in FIG. 76. The cap includes a U-shaped body 782 that is sized to be seated on the output face of the source housing $H_S$. The body includes wings 783 that straddle the source housing, and that define end slots 784 for receiving mounting straps 785. The straps are sized to encircle the source housing $H_S$ to hold the U-shaped body on the source housing. The straps include engageable facing surfaces 786 that can include hook-and-loop fasteners. Alternatively, the straps 785 can be webbing-type straps that are engaged by a buckle assembly 787, as shown in FIG. 79.

Figure 78:
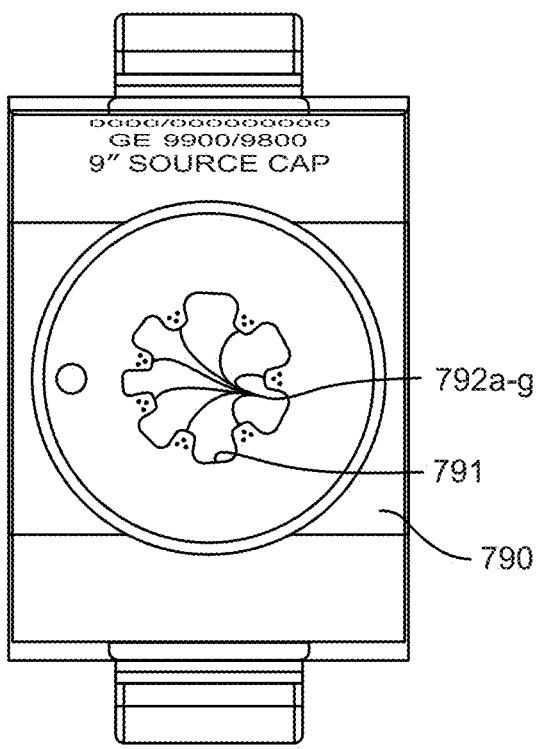
FIG. 78 is a top view of the source calibration device shown in FIG. 77.
Figure 80:
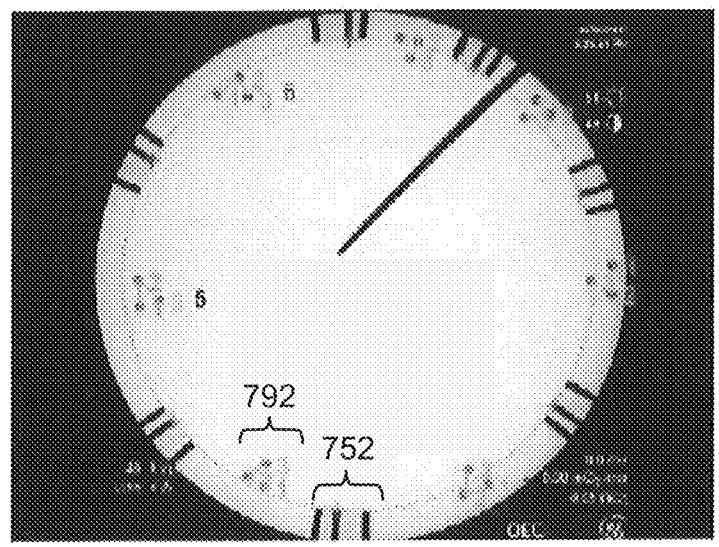
FIG. 80 is an x-ray image showing the glyphs associated with the calibration collar and source calibration device shown above.

The U-shaped body 782 includes a calibration plate 790 that is seated flush with the output face of the source housing $H_S$, as illustrated in FIG. 76. The plate defines an opening 791 that is aligned with the beam transmission path to the X-ray detector of the C-arm device. The plate further defines a plurality of glyphs 792a-g that extend radially into the opening 791 so that the glyphs intersect the beam transmitted by the X-ray source. As with the detector-side glyphs, the glyphs 792a-g for the source-side include a number of metallic beads 793 disposed within the calibration plate 790. The beads in each glyph define a unique pattern, as shown in FIG. 78. The glyphs 792a-g for the source cap 780 are positioned within the circumferential spaces between the glyphs 752a-g of the collar 750 so that the source beads 793 and the detector rods 753 do not interfere with each other in the calibration image, as shown in the x-ray image in FIG. 80.

In accordance with one aspect of the present disclosure, the image processing device 122 is configured to identify the glyphs 752, 792 in an x-ray image for calibrating the C-arm. In particular, the processing device executes software that finds the pixel locations in the X-ray detector pixel array corresponding to the metallic rods and beads forming the glyphs. For the beads in the glyphs 792a-g, the software searches the X-ray image for circular features within a range of known radii, and then evaluates the relative brightness of the pixels inside and outside that radius. The criteria for identifying a particular circular feature as a glyph bead can include raw pixel brightness values, relative brightness difference between inside and outside the circular feature, and/or the homogeneity of the pixels inside and outside the circle. The software can also be constrained to only search for circular features in a particular region of the image, such as in the outer circumferential band containing the glyphs shown in FIG. 80.

The image processing device executes software within a graphics processing unit (GPU) that assigns a detection score to each pixel in the searched region and then winnows out pixels that do not reach a detection score threshold. The software can identify the center of mass of the detected pixels to ascertain the center of the corresponding bead. Once beads have been detected in the image, their tracked positions can be determined based on the known position of the C-arm (and thus the known position of the pixel array of the X-ray detector). This known position can be compared a predicted position based on the location of the bead pixels as determined by Equations 1-5 above. The difference in actual vs. predicted position is a measure of the error of the model used by the image processing software. The image processing software then proceeds to optimize the parameters of the model used to identify the actual positions of all of the pixels in the detection array. One approach is essentially a brute force optimization process in which the parameters of the model are modified until they converge on a zero or minimal error. In another approach, a calibration look-up table can be maintained for the different parameters based on previous model calibrations. The calibration look-up tables can consider the known impact of the pose of the C-arm, such as pitch angle and orbital angle which can be affected by gravity.

The calibration collar 750 and source cap 780 can be used jointly or individually to calibrate the C-arm predicted position to the actual position of the C-arm. This calibration process can occur every time an x-ray image is taken of the surgical site to ensure that the model used to locate anatomy and surgical devices within the surgical field is accurate. Ideally, once the C-arm position is initially calibrated prior to the surgical procedure, no further calibration is necessary. However, the reality is that the actual position of the C-arm shifts from its expected position over time, however slightly. But even slight shifts in C-arm position can affect where a surgical instrument is used or an implant is positioned. Thus, the image processing system disclosed herein contemplates re-calibration of the C-arm—whether source, detector or both—at each new live image.

Figure 81:
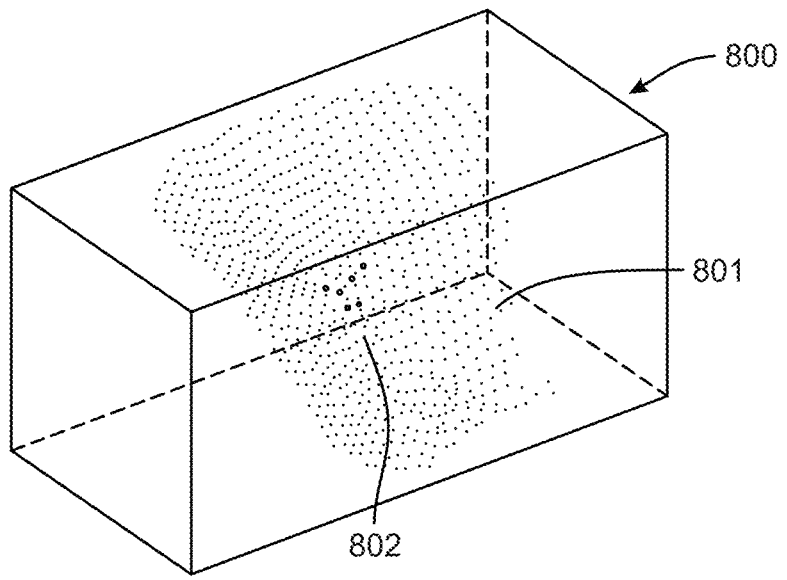
FIG. 81 is a perspective view of a calibration phantom used to calibrate the C-arm according to the methods shown above.
Figure 82A:
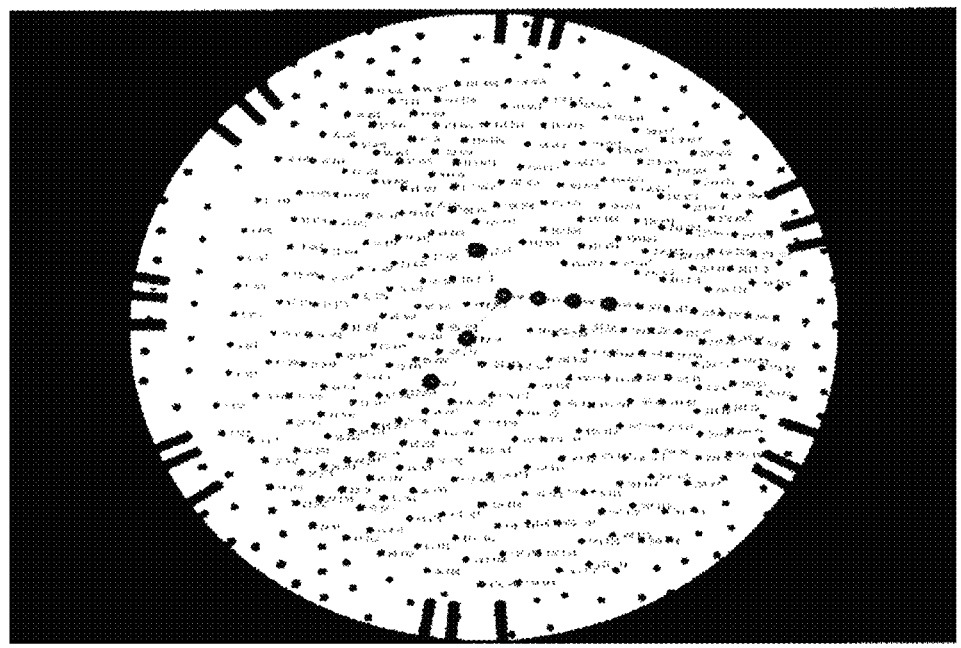
FIG. 82A is an X-ray image of a baseline position of the C-arm using the calibration phantom.
Figure 82B:
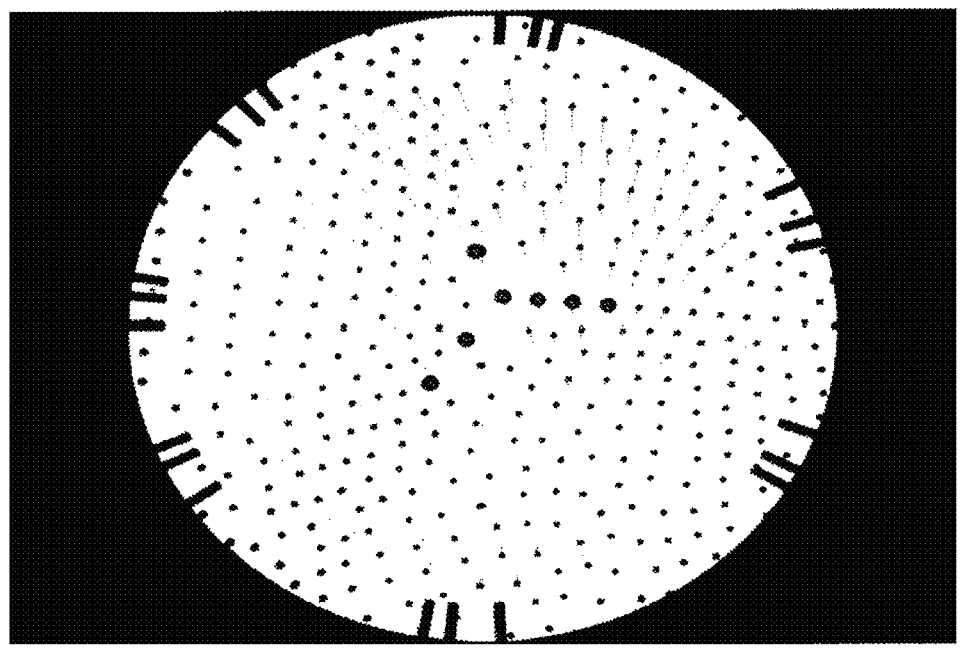
FIG. 82B is an X-ray image of a current C-arm position using the calibration phantom showing the offset from the baseline position.

In another aspect, a 3D calibration phantom 800, such as the phantom shown in FIG. 81, can be used to determine the calibration error in the C-arm. The phantom includes a plurality of beads 801 embedded within a radio-transparent block that can be imaged over a clinically relevant range of C-arm pitch and orbital angles. A predefined set of beads 802 are larger than the rest of the beads, with this predefined set forming a specific pattern, such as the Y-pattern shown in FIG. 81. The X-ray image of the phantom is shown in FIG. 82B, for comparison with the predicted bead positions shown in FIG. 82A. The image in FIG. 82B illustrates the offset between the actual bead position and the bead position predicted by the system model. The lines emanating from each bead pixel corresponds to the error, and it is this error that can be minimized as described above. The model can be calibrated to eliminate the errors in subsequent imaging steps. In particular, the tracking system can be registered to the X-ray image so that the actual system locations of all pixels in the image are known. These pixels include images of the instruments being guided in the image, which can be registered to the representations of the instrument and its path being displayed on the X-ray image.

Figure 84A:
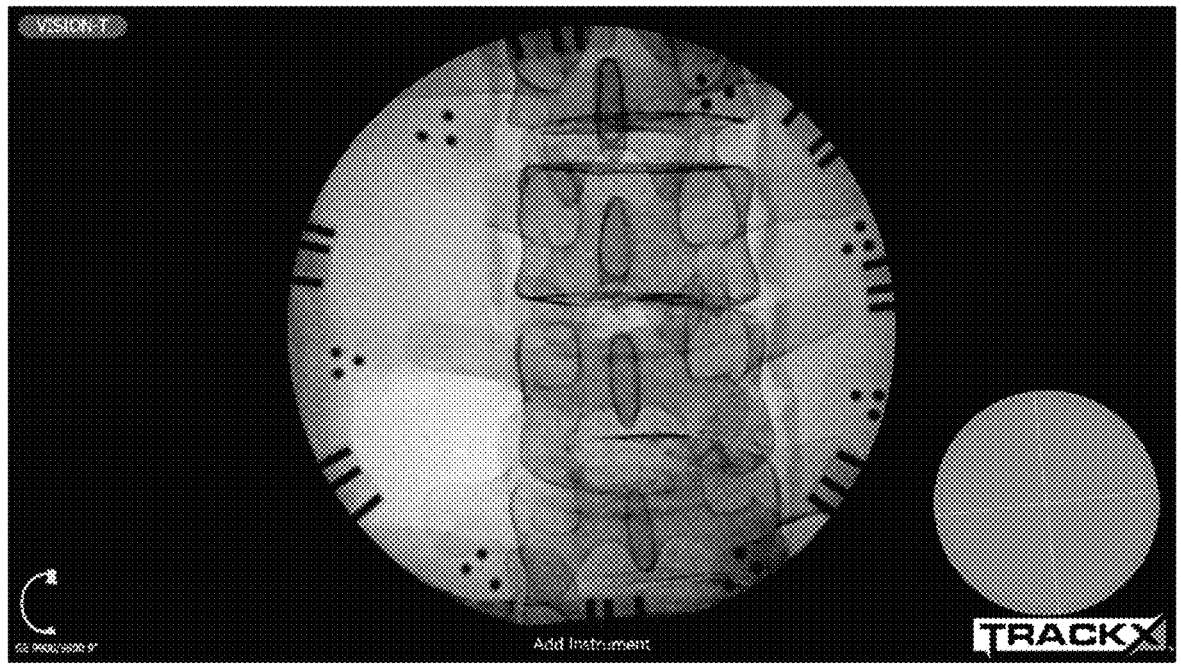
FIG. 84A is a screen shot of a display of an X-ray image of a surgical site prior to introduction of an instrument.
Figure 84B:
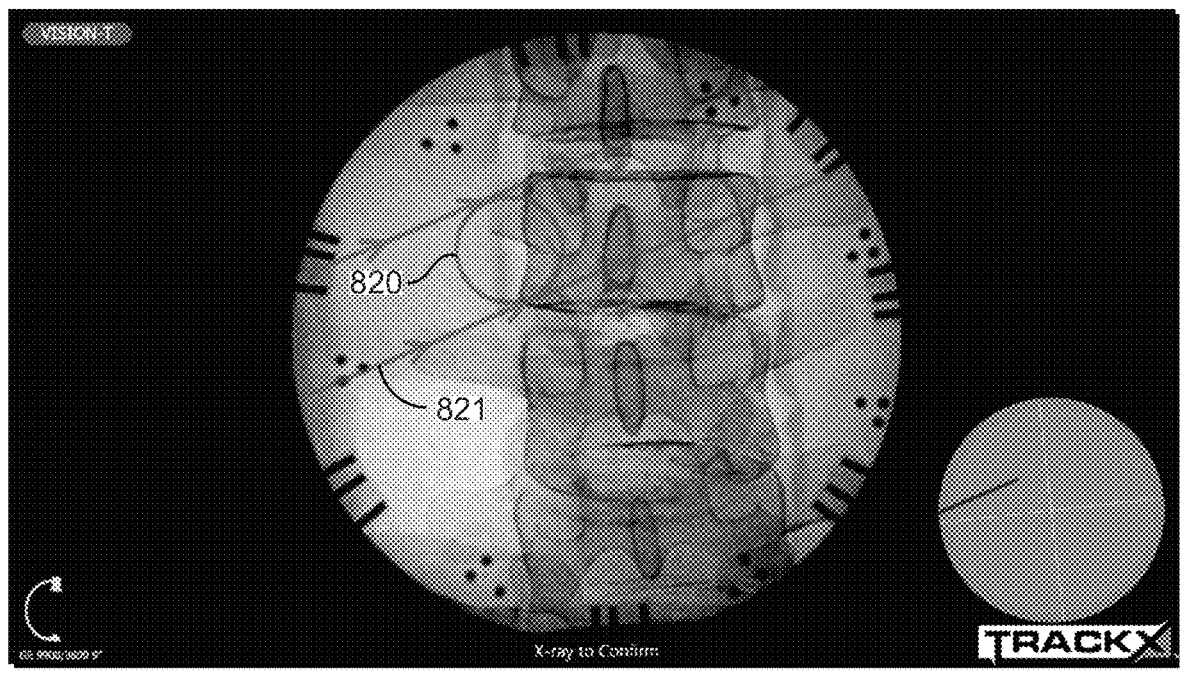
FIG. 84B is a screen shot of a display of the X-ray image of FIG. 84A with markings indicative of a surgical instrument overlaid thereon.

As described above, the present disclosure contemplates an imaging system that can detect metal objects—such as tool, instruments and implants—within an x-ray image of a surgical site and can enhance the depiction of that metal object in the image presented to the surgeon and/or x-ray technologist. In accordance with the method, an initial x-ray image is acquired of the surgical site, as shown in the screen shot of FIG. 84A. As reflected in the smaller image at the lower right of the screen shot, no metallic instrument has been introduced into the field of view. In the next step shown in the screen shot of FIG. 84B, an instrument is introduced into the field, as reflected in the smaller image in the screen shot. The image processing device and software can determine the alignment and orientation of the instrument using the methods described above. Since no new x-ray has been taken with the instrument in the field of view, the image processing device and software overlays a "train tracks" display on the x-ray image, with the depiction of the train tracks 820 coinciding with the orientation and direction of movement of the instrument as it enters the viewing field. A circle 821 within the train tracks, and particularly the center of that circle, identifies the location of the working end or tip of the instrument, which is known by the image processing device as described above. It is understood that the train tracks and circle can follow the instrument as it is moved within the viewing field because the instrument is being tracked by the optical tracking system and methods described above.

Figure 84C:
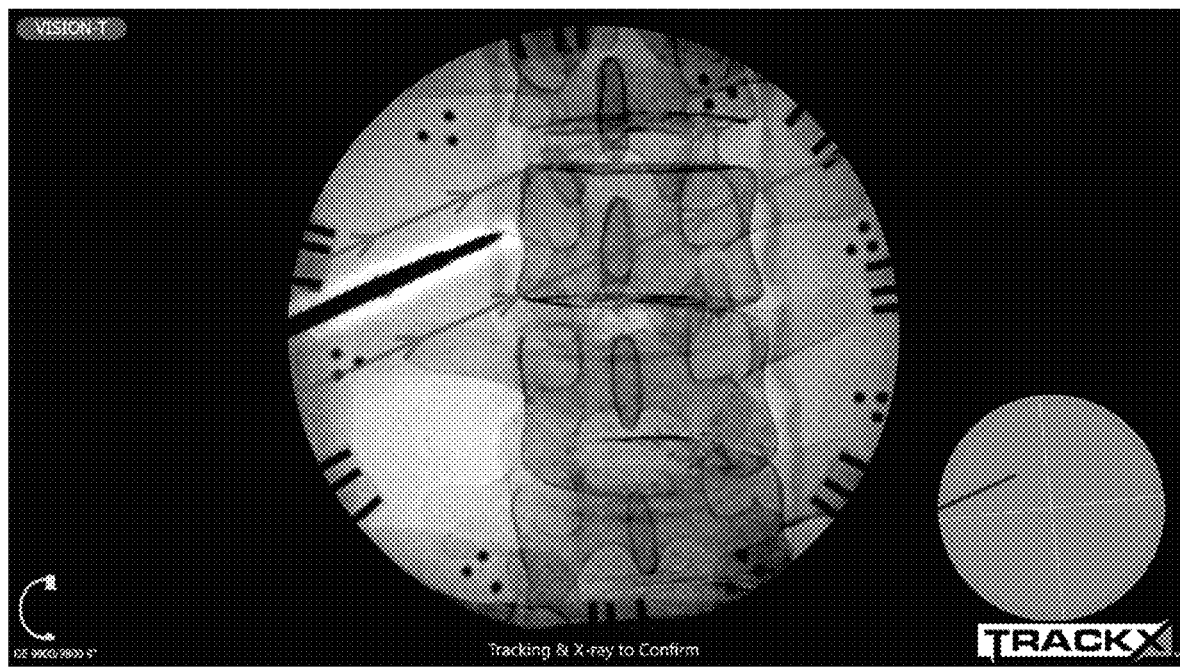
FIG. 84C is a screen shot of a display of the X-ray image of FIG. 84B with an X-ray of the instrument included in the field of view.

With the instrument in a first relevant position, an x-ray image of the surgical field is acquired so that the metallic instrument is now visible in the image, as shown in the screen shot of FIG. 84C. However, rather than simply show the actual x-ray appearance of the instrument, the image processing device of the present disclosure can enhance the appearance of the instrument. The image processing software determines which pixels of the x-ray image correspond to the metallic instrument using the techniques described above. The software then enhances the intensity of the pixels identified as the instrument and introduces a white "halo" for certain pixels around the instrument pixels. This halo not only enhances the clarity of the instrument in the x-ray image but also ensures that all of the instrument is visible to the surgeon. In one feature, the size of the halo around the instrument can be user-selected according to user preferences. As the surgeon moves the instrument, the train tracks, the enhanced image of the instrument and the halo all move with the instrument while the underlying x-ray image of the surgical field remains intact. In another aspect, the white halo is replaced with an essentially transparent "halo" in which the background anatomy is visible. More specifically, the image pixels corresponding to the location of the transparent "halo" are overlaid with the pixels of the underlying image of the anatomy at the location of the "halo" as the instrument moves across the anatomy.

In another feature, the opacity of the image of the instrument can be adjusted relative to the background image of the anatomy over which the instrument is moving. Since the display of the image is pixel-based, the intensity of the pixels identified as corresponding to the metallic instrument can be adjusted to the user's preference. This feature can be particularly useful when the instrument traverses anatomic landmarks. Reducing the opacity can allow the background image of the anatomy to be visible along with a low intensity image of the instrument. In a further feature, the opacity or intensity of the instrument can be varied along the length of the instrument so that the working tip, for instance, is opaque, whereas the body of the instrument can be less opaque so that anatomic landmarks can be visible beneath a low intensity depiction of the body of the instrument. Even more specifically, the pixels of the body of the instrument can be made transparent so that the stationary anatomy and the working tip are the only structure visible in the image. In certain embodiments, the change in instrument opacity can be "on the fly", meaning that the radiologist or surgeon can make an instrument transparent in an image in order to visualize the underlying anatomy and then increase the opacity so the image can be viewed on the anatomy as the instrument is moved relative to that anatomy.

Figure 85A:
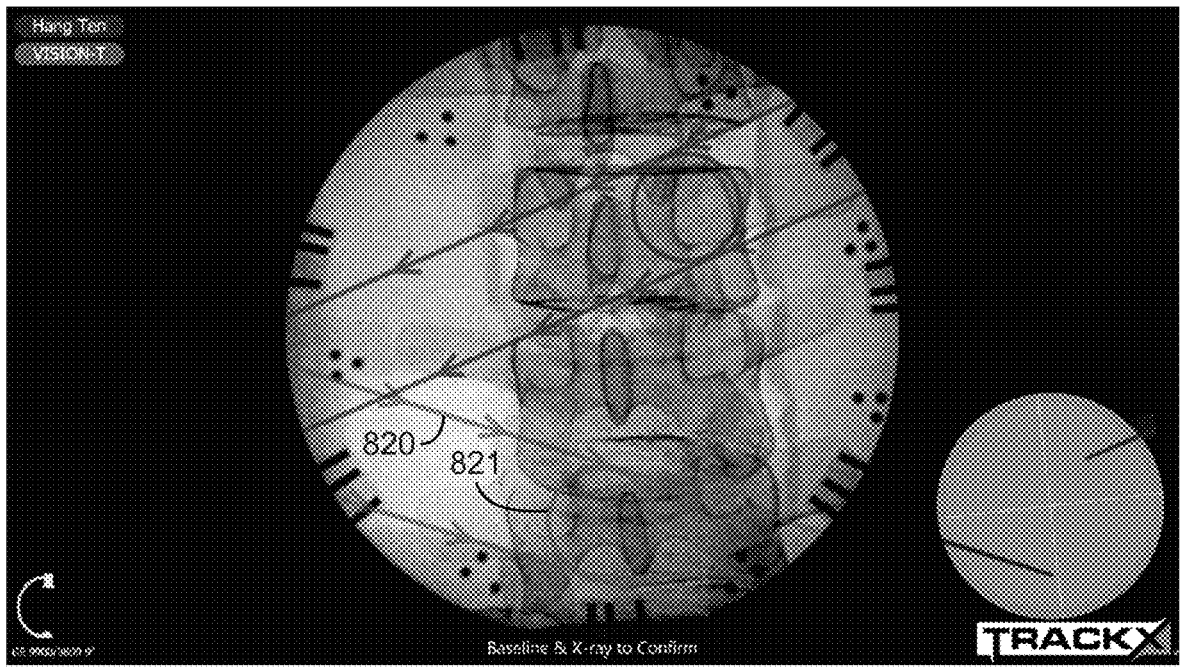
FIG. 85A is a screens shot of a display of an X-ray image with markings indicative of two instruments overlaid thereon.
Figure 85B:
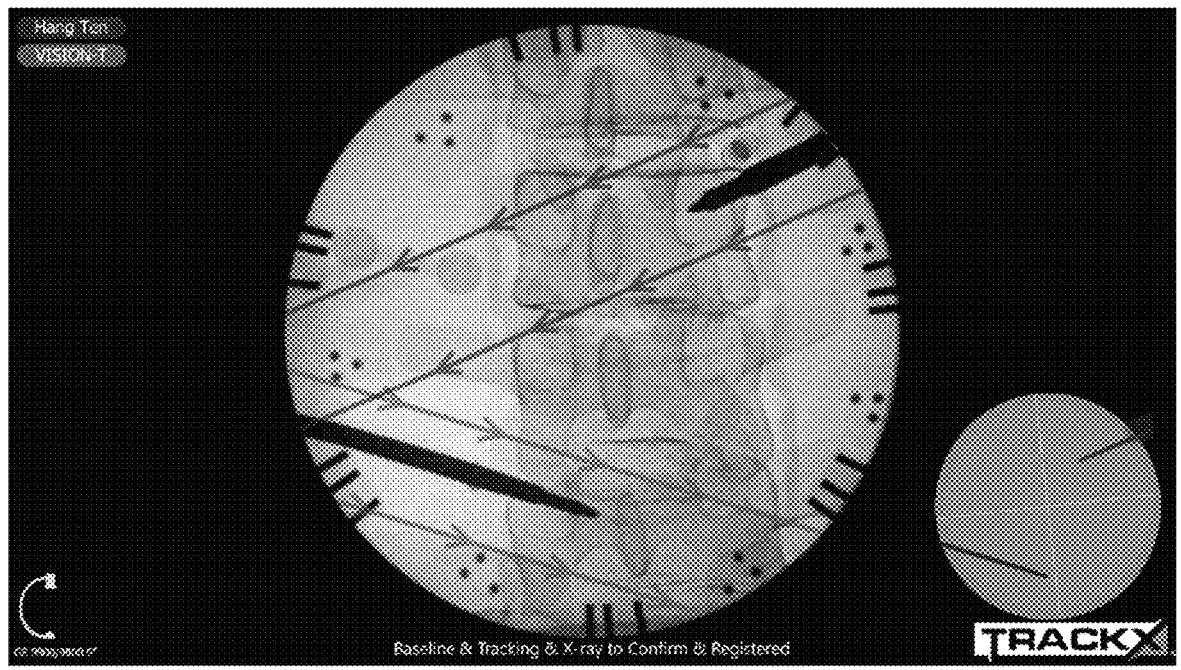
FIG. 85B is a screen shot of the image shown in FIG. 85A with an X-ray of the instruments included in the field of view.

As described above, new x-ray images can be acquired at various stages of the manipulation of the instrument to verify the actual position and to permit continuous calibration of the displayed image of the instrument in future movements. It is noted that this method can be applied to all metallic objects introduced into the surgical field. Thus, as shown in FIGS. 85A-85B two instruments are in the viewing field, with the position and tip location shown with the train tracks 820 and circle 821 in FIG. 85A and with the actual instruments shown in a subsequent x-ray in FIG. 85B. It can be appreciated that each of the images of the instruments in FIG. 85B can be enhanced as described above so that movement of any one instrument or both instruments do not disrupt the image of the underlying anatomy.

Figure 86A:
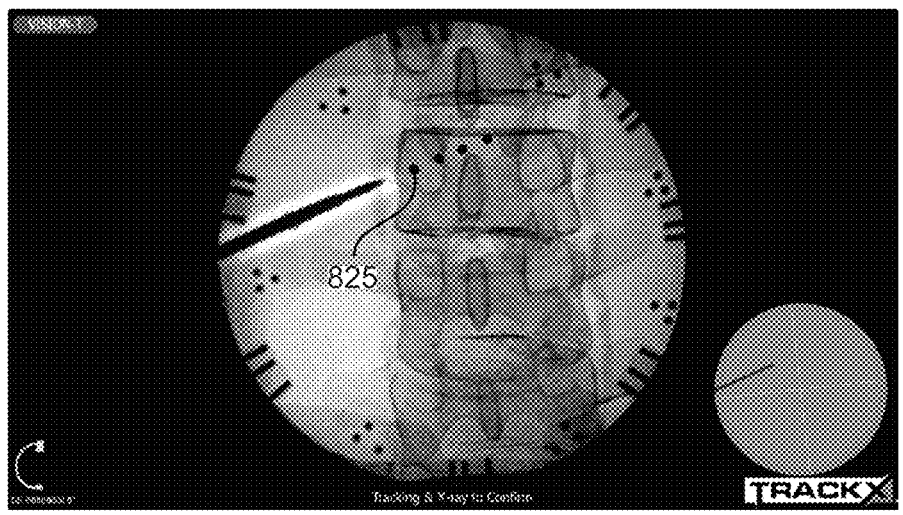
FIG. 86A is a screen shot of a display of an X-ray image of a surgical site showing an instrument in an initial position with reference indicators aligned with the axis of the instrument.

In another feature, reference indicators 825 can be projected in an image, such as the image shown in FIG. 86A. In this approach, the location of the instrument shown in the image is known from the tracking system 130 that detects the location of tracking elements carried by the instrument, and the tip of that instrument is known from calibration data and/or device data accessed by the tracking system. The trajectory of the instrument can then be determined, meaning the orientation of the longitudinal axis of the instrument and its direction of movement. The reference indicators 825 can be positioned relative to the known tip of the instrument and extended along the trajectory to show where the instrument will be when advanced along that trajectory. In one embodiment the reference indicators are in the form of uniformly spaced dots, with the dots spaced at 1 cm intervals from the known instrument tip in a specific embodiment.

Figure 86B:
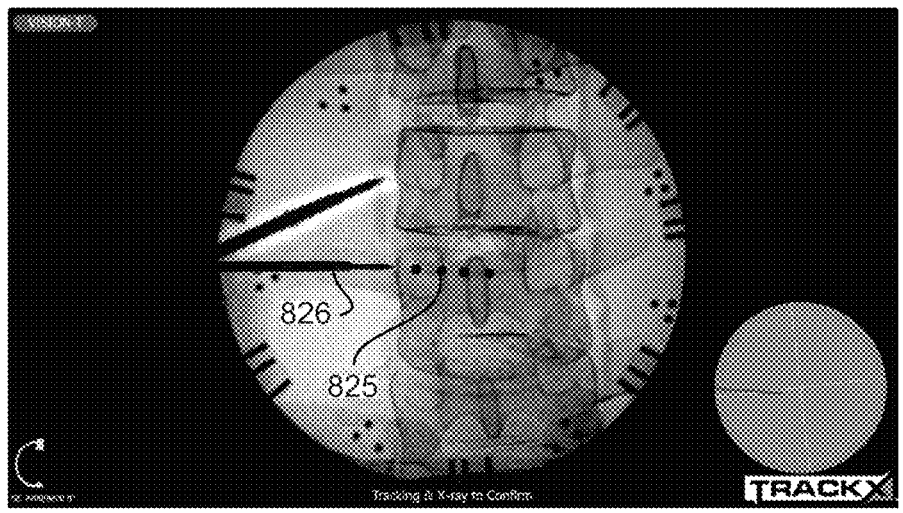
FIG. 86B is a screen shot of the display shown in FIG. 86A as the instrument is being moved, with the reference indicators moving with the instrument.
Figure 86C:
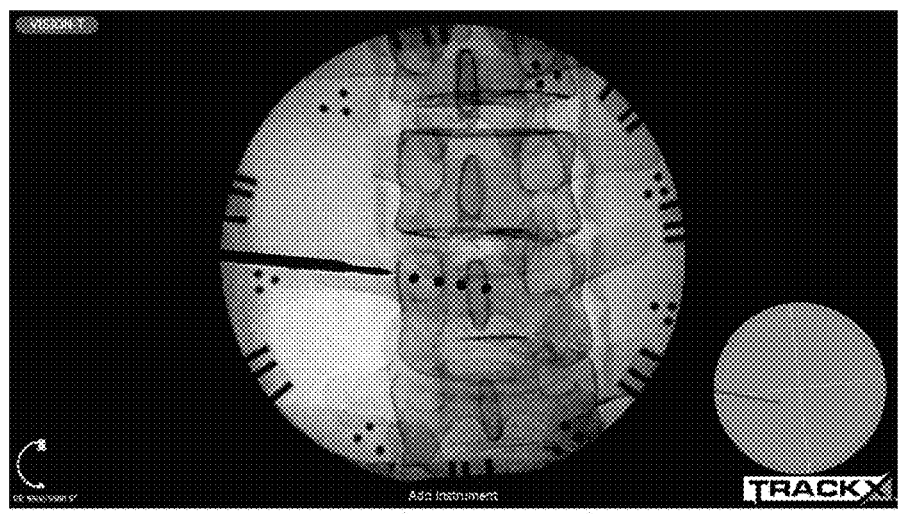
FIG. 86C is a screen shot of a display of a new X-ray image showing the instrument in its new orientation.

As shown in FIG. 86B, an image of the instrument as it is being moved is overlaid onto the current X-ray image showing the anatomy with the position of the instrument at the time of the X-ray shot. The moving instrument can be displayed as a "shadow" or translucent so that the underlying anatomy is visible beneath the image of the moving instrument. The moving instrument is also displayed in the smaller image at the lower right. The reference indicators 825 move with the instrument. The reference indicators thus provide the surgeon with a direct display of where the tip of the instrument will be if the instrument is advanced along its trajectory. When the instrument is generally aligned with a desired location and orientation, a new X-ray shot can be taken to produce a new image shown in FIG. 86C, again with the reference indicators 825 displayed. The surgeon can then advance the instrument along the trajectory indicated by the reference indicators and know that the instrument is exactly aligned for the procedure being performed.

Figure 87A:
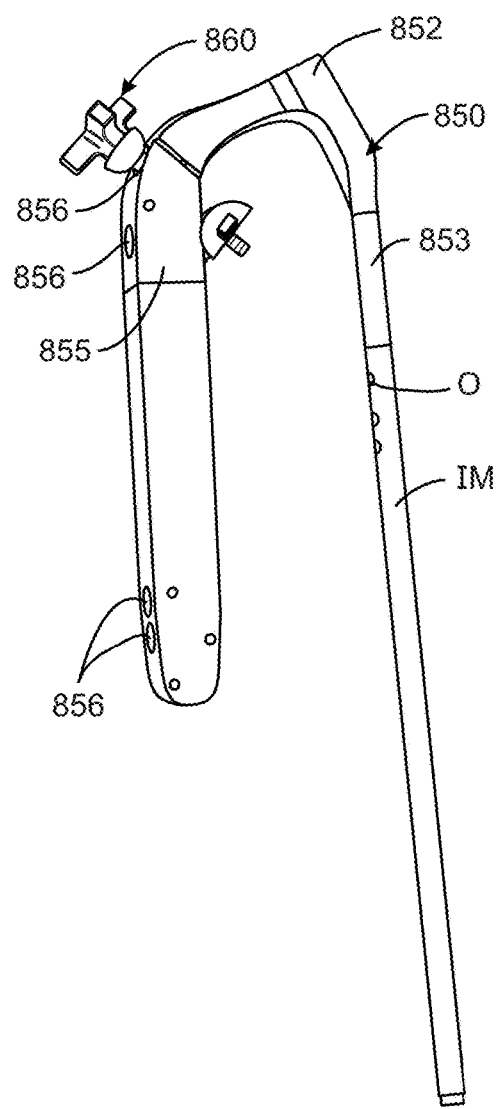
FIGS. 87A-87B are side views of an intramedullary nail and a nail guide incorporating a tracking element according to one aspect of the present disclosure.
Figure 87B:
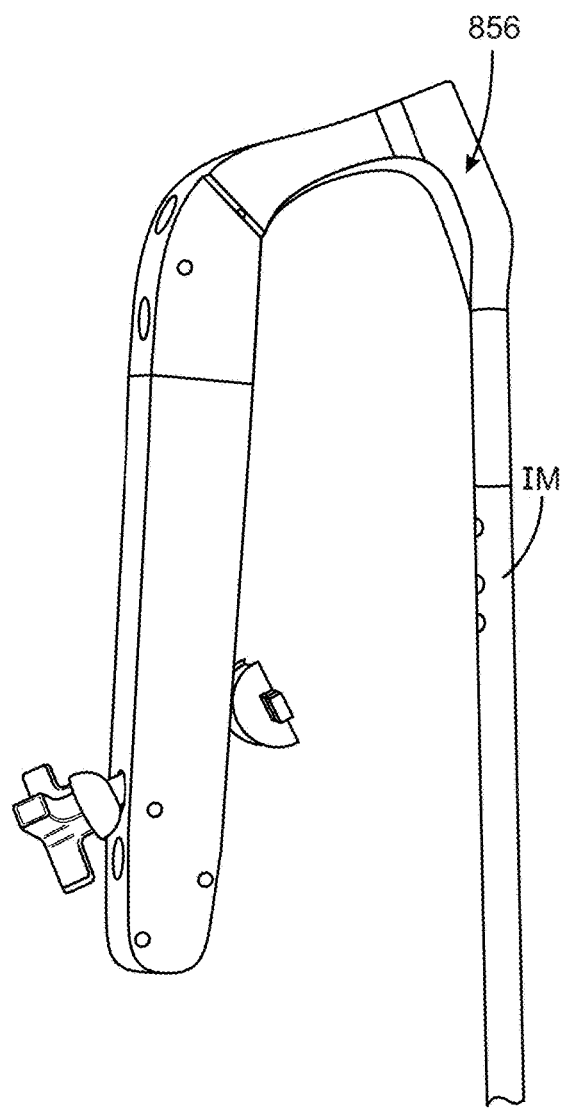

In another aspect of the present disclosure, an image guided intramedullary nail arrangement is provided that includes a drill guide 850 configured to align a drill with an intramedullary nail IM disposed within the intramedullary canal of a long bone, as shown in FIGS. 87A, 87B. The drill guide includes a U-shaped body 852 that includes an elongate stem 853 to which the intramedullary nail IM is engaged, and an alignment body 855 that defines a plurality of thru-holes 856 that are aligned with a corresponding plurality of openings O in the nail IM. Conventional fasteners, such as bone screws, are guided through the thru-holes 856 into the long bone and through the aligned opening O to fix the nail to the bone. With the nail IM properly engaged to the stem 853 of the drill guide 850, the thru-holes 856 are perfectly aligned with an associated opening O in the nail.

Figure 89A:
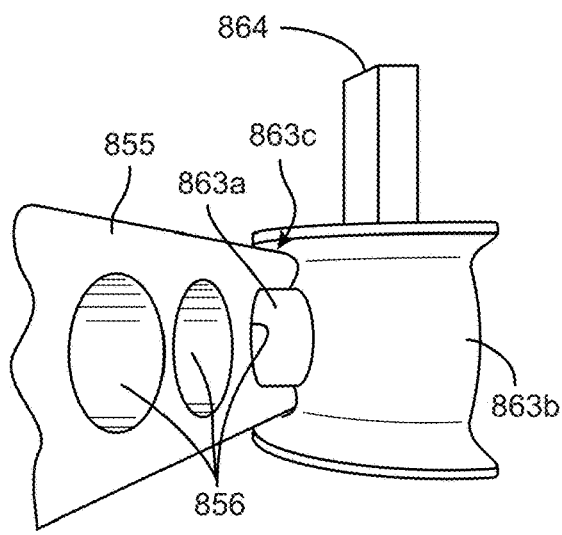
FIGS. 89A-89C are detail views of the engagement of the bolt assembly of FIGS. 88A-88B to the nail guide.
Figure 89B:
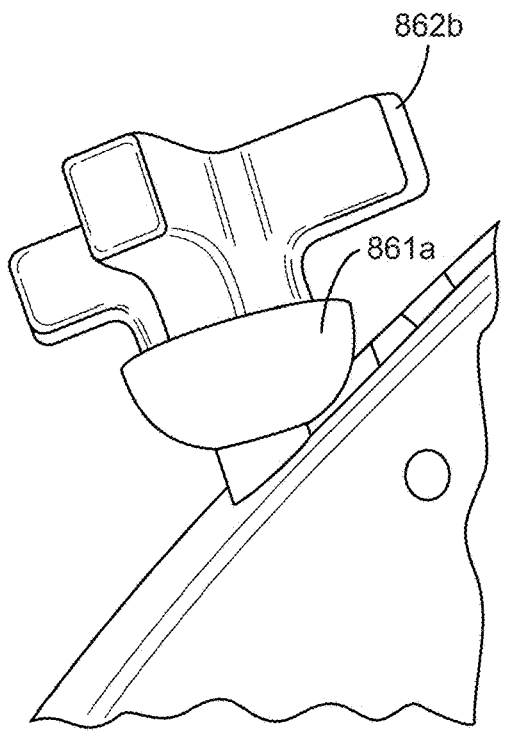
Figure 89C:
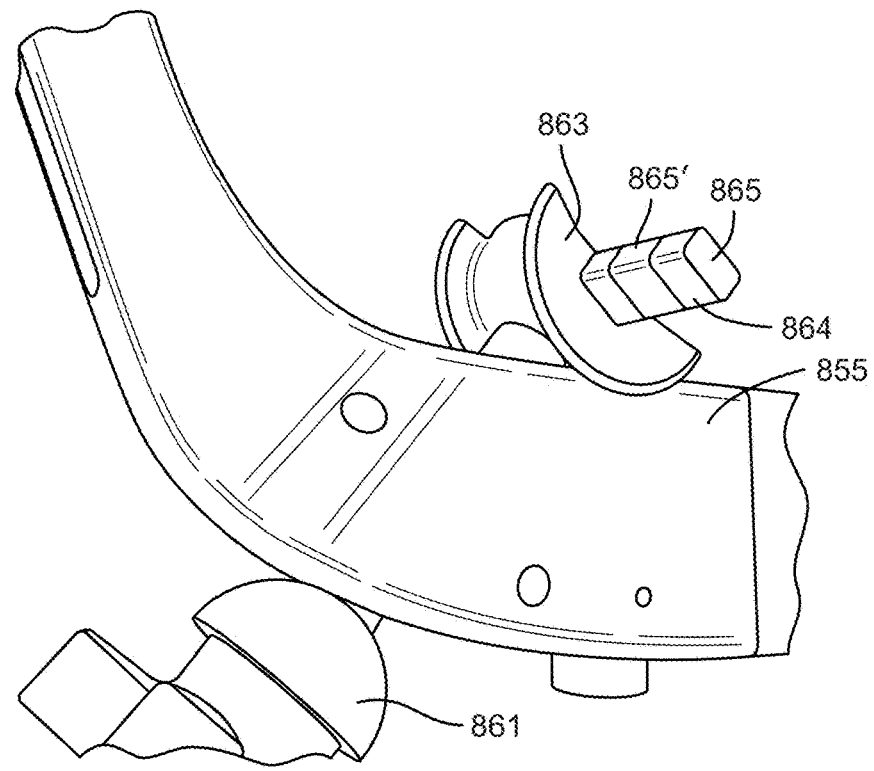

Since the intramedullary nail IM is necessarily embedded within the bone, its location cannot be easily tracked during a surgical procedure. The present disclosure thus contemplates tracking the position and orientation of the drill guide 850. In one embodiment, a bolt assembly 860 is provided that can be fixed within an unused one of the thru-holes 856, as shown in FIGS. 87A, 87B and 89A-89C. The assembly includes an upper portion 861, a threaded bolt 862a and a lower portion 863. The upper portion 861 includes a stem 861a that is sized to fit snugly within one of the thru-holes 856, and a hemispherical body 861b that is configured to contact the surface of the drill guide 850 around the thru-hole, as shown in FIG. 89B. The threaded bolt 862a includes an integral knob 862b for rotating the bolt 862a to thread it into the stem 863a of the lower portion 863. The lower portion includes the stem and a cylindrical body 863b. The cylindrical body is configured to contact the underside of the drill guide when the bolt assembly 860 is engaged thereto. It should be understood that the entire assembly is tightened onto the drill guide with the bolt 862a passing through the thru-hole 856 so that the position of the bolt assembly is fixed relative to the drill guide. The lower portion 864 includes wedge-shaped flanges 863c flanking the cylindrical body that are arranged to engage the sides of the drill guide, as shown in FIGS. 89A and 89C. The flanges prevent the bolt assembly, and particularly the lower portion 863 from rotating relative to the drill guide 850.

Figure 88A:
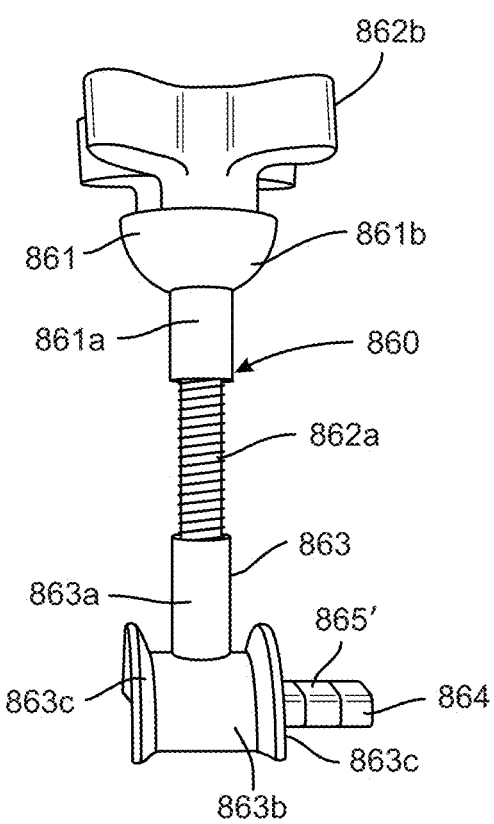
FIGS. 88A-88B are enlarged views of a bolt assembly used with the nail guide shown in FIGS. 87A-87B.
Figure 88B:
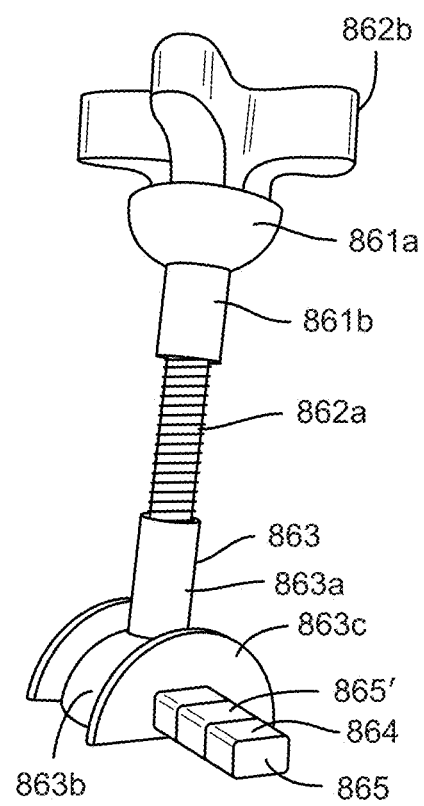

The lower portion includes a projection 864 that projects perpendicularly from the lower portion 863, and thus perpendicularly from the drill guide, as shown in FIGS. 88A and 89C. The projection can include a tracking marker 865 and/or 865' that can be integral with or affixed to the end of the projection 864, as shown in FIGS. 88B and 89C. The tracking marker 865 is disposed at the exposed end of the projection, while the tracking marker 865' is a band that encircles the projection. The tracking markers 865, 865' are configured to be detected by the tracking device 130 in the manner of the tracking elements described above. The image processing device 122 and software can determine the position of the tracking markers 865, 865' in system coordinates which means that the image processing software knows where the "knows" where the bolt assembly 860, and thus the drill guide 850 is relative to the patient's anatomy when visualized by X-ray. The geometry of the nail guide and of the intramedullary nail IM engaged thereto can be provided to the image processing software so that the position of the nail IM and its openings O are known. With all of this information known, the image processing software can guide the introduction of the bone screw through the nail guide, such as by using the concentric circles described above with respect to FIGS. 83A-83B.

In another embodiment, a tracking element 870 is provided that can be affixed to a surface of the nail guide 850. The tracking element 870 includes a removable portion 872 that includes a base 873 and a projection 874 extending outward from the base. Tracking markers 880, 880' can be integral with or affixed to the projection in the same manner as the tracking markers 865, 865'. The tracking element 870 further includes a mounting portion 875 with a base 876 having an adherent bottom surface that is configured to be adhered to the nail guide 850, as shown in FIG. 90A. The adherent surface can be covered with a removable tag 877 that is removed when it is desired to mount the tracking element 870 on a drill guide. The mounting portion includes a base 876 that defines at least two snap elements 878. The snap elements are configured to engage a like number of snap elements 879 on the underside of the removable portion 872, as shown in FIG. 90C. The snaps are configured to lock the position of the upper portion, and therefore the tracking markers 880, 880' relative to the nail guide 850. The tracking element 870 can be mounted anywhere on the nail guide that will not interfere with its proper use. The position of the tracking markers 880, 880' can be calibrated in a manner described above so that the position of the tracking marker relative to the nail guide and to the intramedullary nail IM mounted thereto is known. The snap elements 878, 879 allow the removable portion 872 to be removed at any time that instrument tracking is not needed. Then when tracking is required, the removable portion 872 can be snapped onto the mounting portion 875 so that the instrument can be tracked by the tracking device 130 and image processing device 122.

The present disclosure should be considered as illustrative and not restrictive in character. It is understood that only certain embodiments have been presented and that all changes, modifications and further applications that come within the spirit of the disclosure are desired to be protected.

What is claimed is:

1. A tracking element for a surgical tool or instrument having an elongated shaft and a working tip, the tracking element comprising:

a cylindrical body configured to clamp onto the elongated shaft of the tool or instrument;

at least one concentric band at least partially encircling the outside surface of the cylindrical body, the at least one concentric band adapted to be detected by an optical localizer or an optical detection device associated with an x-ray imaging system, wherein the at least one concentric band is an optical tape applied to the outside surface of the body.

2. The tracking element of claim 1 wherein the at least one concentric band has a band width that is indicative of the type of tool or instrument.

3. The tracking element of claim 1, further comprising an arm projecting outward from said cylindrical body and including a band on the outside surface of the arm adapted to be detected by an optical localizer or optical detection device.

4. The tracking element of claim 1, wherein said cylindrical body includes a resiliently deflectable body having an undeformed configuration defining a diameter less than the diameter of the tool or instrument and deformable to define a diameter larger than the diameter of the tool or instrument sufficient for said deflectable body to be mounted on the tool or instrument.

5. A tracking element for a surgical tool or instrument having an elongated shaft and a working tip, the tracking element comprising:

a cylindrical body configured to clamp onto the elongated shaft of the tool or instrument;

at least two concentric bands at least partially on the outside surface of the cylindrical body, the at least two concentric bands adapted to be detected by an optical localizer or an optical detection device associated with an x-ray imaging system, wherein the at least two concentric bands are positioned apart at a predetermined distance indicative of the type of tool or instrument.

6. A tracking element for a surgical tool or instrument having an elongated shaft and a working tip, the tracking element comprising a sticker configured to be mounted on and at least partially encircling the elongated shaft of the tool or instrument, the sticker including at least two concentric bands arranged to at least partially encircle the elongated shaft when the sticker is mounted thereon, the at least two concentric bands adapted to be detected by an optical localizer or an optical detection device associated with an x-ray imaging system, wherein the at least two concentric bands are positioned apart at a predetermined distance indicative of the type of tool or instrument.

7. A tracking element for a surgical tool or instrument having an elongated shaft having a longitudinal axis and a working tip, the tracking element comprising:

a mounting portion configured to be engaged to the elongated shaft of the tool or instrument;

an elongated arm extending from the mounting portion laterally relative to the elongated shaft when the mounting portion is engaged thereon;

at least one two marker supports at an end of the arm offset from the mounting portion and offset from the longitudinal axis of the tool or instrument, said two marker supports defining a marker axis therebetween that is offset from and non-colinear with the longitudinal axis of the tool or instrument when the tracking element is mounted thereon; and a marker mounted on each of said two marker supports, said marker formed of a material that is radio-transparent to x-rays but detectable by an optical detector.

8. The tracking element of claim 7, wherein the marker support includes a cylindrical arm and said marker is cylindrical and configured to be mounted on said cylindrical arm.

9. The tracking element of claim 7, wherein said mounting portion includes a cylindrical portion configured to receive a third cylindrical marker mounted thereon.

10. The tracking element of claim 7, wherein:

said two marker supports are on a plate defining at least two marker openings that are open on opposite sides of the plate; and said marker is a disc configured to be mounted in a corresponding marker opening and is detectable by the optical detector on said opposite sides of the plate.

11. The tracking element of claim 10, wherein said at least two marker openings define a line between the center of said openings that is at a non-parallel, non-perpendicular angle relative to a longitudinal axis of the elongated shaft of the tool or instrument on which the marker support is engaged.

12. The tracking element of claim 11, wherein said angle of said line between the center of said openings is configured to intersect a working tip of the tool or instrument when the marker support is engaged on the shaft of the tool or instrument.

13. A calibration tool for use with the tracking element of claim 12, comprising:

an elongated shaft having a tip for contacting a calibration surface adjacent the working tip of a tool or instrument contacting the same surface; and at least one platform projecting laterally from said elongated shaft at a predetermined distance from said tip, said platform configured to be contacted by the marker support of the tracking element when the marker support is engaged on the shaft of the tool or instrument, said distance corresponding to a height of the tracking element engaged on the tool or instrument so that the line between the center of said openings intersects the working tip of the tool or instrument.

* * * * *